United States Patent [19]

Yankee

[11] 4,026,909

[45] May 31, 1977

[54] CIS-13-PGF$_2$ ANALOGS

[75] Inventor: Ernest W. Yankee, Portage, Mich.

[73] Assignee: The Upjohn Company, Kalamazoo, Mich.

[22] Filed: July 14, 1975

[21] Appl. No.: 595,869

[52] U.S. Cl. ............................ 260/408; 260/240 R; 260/343.2 R; 260/343.3 R; 260/345.3; 260/345.8; 260/345.9; 260/346.2 R; 260/347.4; 260/347.8; 260/410; 260/410.5; 260/410.9 R; 260/413; 260/448.8 R; 260/418; 260/473 A; 260/473 G; 260/514 D; 260/520 B; 260/520 C; 424/305; 424/308; 424/317
[51] Int. Cl.$^2$ ....................................... C07C 177/00
[58] Field of Search .......... 260/468 D, 514 D, 408

[56] References Cited

UNITED STATES PATENTS 3,816,393  6/1974  Hayashi et al. .................... 260/209
3,932,479  1/1976  Bernady et al. .................... 260/448

Primary Examiner—Robert Gerstl
Attorney, Agent, or Firm—Robert A. Armitage

[57] ABSTRACT

This invention comprises certain analogs of the prostaglandins in which the double bond between C-13 and C-14 is of the cis configuration. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

36 Claims, No Drawings

CIS-13-PGF₂ ANALOGS

BACKGROUND OF THE INVENTION

This invention provides novel compositions of matter. This invention further provides novel processes for producing these compositions of matter. This invention further provides novel chemical intermediates useful in the above processes.

Particularly this invention provides novel analogs of some of the known prostaglandins which differ from corresponding known prostaglandins in that these prostaglandin analogs have a double bond between C-13 and C-14 of the cis configuration.

The known prostaglandins include the PGE compounds, e.g. prostaglandin $E_1$ ($PGE_1$), prostaglandin $E_2$ ($PGE_2$), prostaglandin $E_3$ ($PGE_3$), and dihydroprostaglandin $E_1$ (dihydro-$PGE_1$).

The known prostaglandins include $PGF_\alpha$ compounds, e.g. prostaglandin $F_{1\alpha}$ ($PGF_{1\alpha}$), prostaglandin $F_{2\alpha}$ ($PGF_{2\alpha}$), prostaglandin $F_{3\alpha}$ ($PGF_{3\alpha}$), and dihydroprostaglandin $F_{1\alpha}$ (dihydro-$PGF_{1\alpha}$).

The known prostaglandins include $PGF_\beta$ compounds, e.g. prostaglandin $F_{1\beta}$ ($PGF_{1\beta}$), prostaglandin $F_{2\beta}$ ($PGF_{2\beta}$), prostaglandin $F_{3\beta}$ ($PGF_{3\beta}$), and dihydroprostaglandin $F_{1\beta}$ (dihydro-$PGF_{1\beta}$).

The known prostaglandins include PGA compounds, e.g. prostaglandin $A_1$ ($PGA_1$), prostaglandin $A_2$ ($PGA_2$), prostaglandin $A_3$ ($PGA_3$), and dihydroprostaglandin $A_1$ (dihydro$PGA_1$).

The known prostaglandins include PGB compounds, e.g. prostaglandin $B_1$ ($PGB_1$), prostaglandin $B_2$ ($PGB_2$), prostaglandin $B_3$ ($PGB_3$), and dihydroprostaglandin $B_1$ (dihydro-$PGB_1$).

Each of the above mentioned known prostaglandins (PG's) is a derivative of prostanoic acid which has the following structure and carbon atom numbering

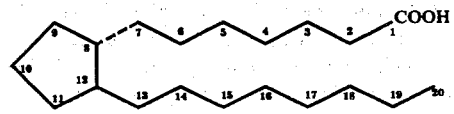

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

$PGE_1$ has the following structure:

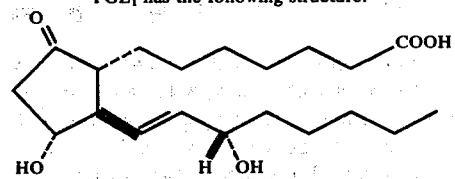

$PGE_2$ has the following structure:

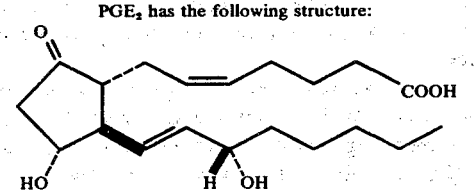

$PGE_3$ has the following structure:

-continued

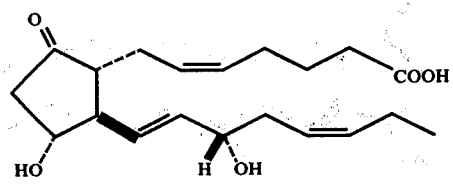

Dihydro-$PGE_1$ has the following structure:

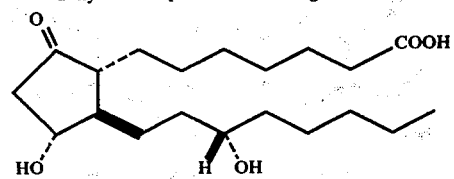

$PGF_{1\alpha}$ has the following structure:

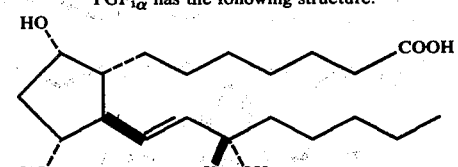

$PGF_{2\alpha}$ has the following structure:

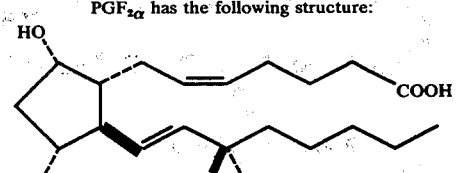

$PGF_{3\alpha}$ has the following structure:

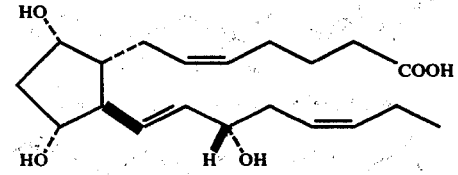

Dihydro-$PGF_{1\alpha}$ has the following structure:

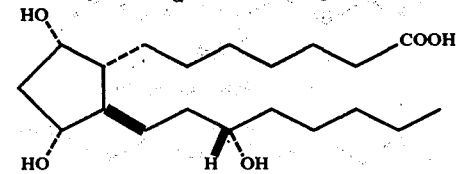

$PGF_{1\beta}$ has the following structure:

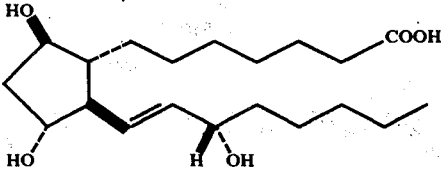

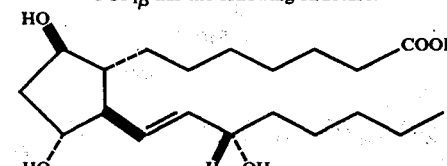

$PGF_{2\beta}$ has the following structure:

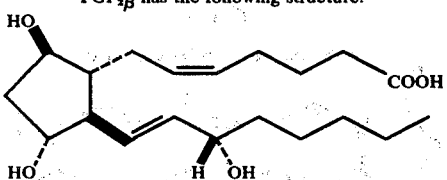

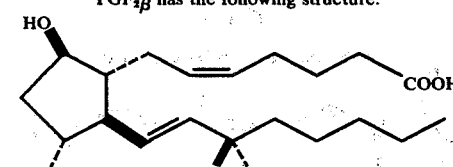

$PGF_{3\beta}$ has the following structure:

-continued

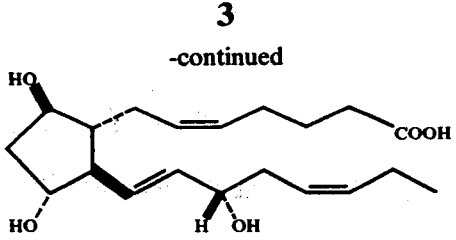

Dihydro-PGF$_{1\beta}$ has the following structure:

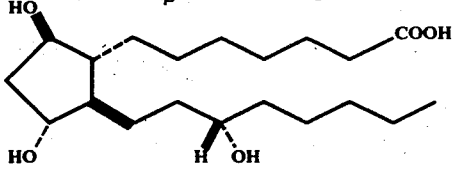

PGA$_1$ has the following structure:

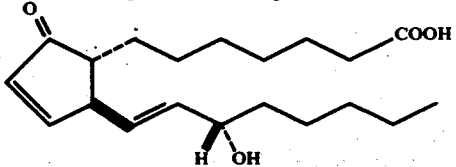

PGA$_2$ has the following structure:

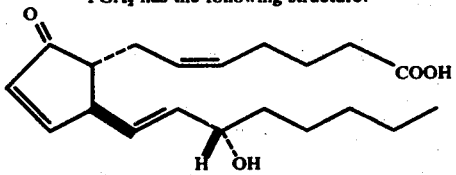

PGA$_3$ has the following structure:

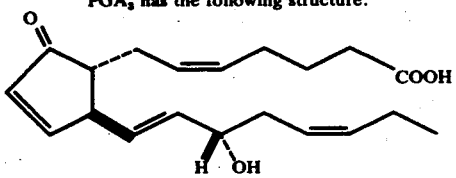

Dihydro-PGA$_1$ has the following structure:

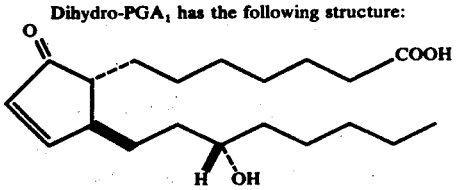

PGB$_1$ has the following structure:

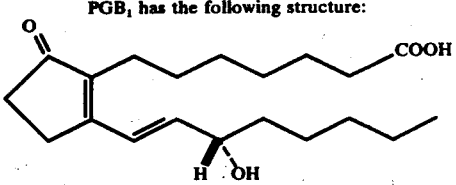

PGB$_2$ has the following structure:

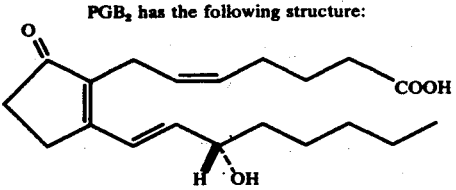

PGB$_3$ has the following structure:

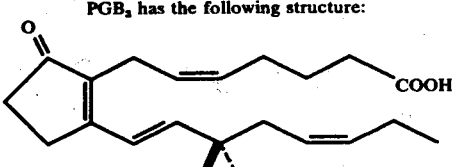

-continued

Dihydro-PGB$_1$ has the following structure:

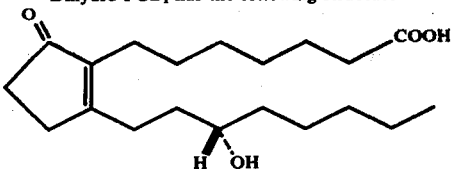

In the above formulas, as well as in the formulas hereinafter given, broken line attachments to the cyclopentane ring indicate substituents in alpha configuration i.e., below the plane of the cyclopetane ring. Heavy solid line attachments to the cyclopentane ring indicate substituents in beta configuration, i.e., above the plane of the cyclopentane ring. The use of wavy lines (~) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins. Expressions such as C-13, C-14, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammalian tissues, for example, sheep vasicular glands, swine lung, or human seminal plasma, from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the term, prostaglandin or PG will mean the optically active form of that prostaglandin thereby referred to with the same absolute configuration as PGE$_1$ obtained from mammalian tissues. When reference to the racemic form of one of those prostaglandins is intended, the word racemic or dl will precede the prostaglandin name.

The various PG's named above, their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein.

For the PGE compounds these biological responses include:

(a) decreasing blood pressure (as measured, for example, in anesthetized, pentolinium-treated rats);

(b) stimulating smooth muscle (as shown by tests, for example, on guinea pig ileum, rabbit duodenum, or gerbil colon);

(c) effecting lipolytic activity (as shown by antagonism of epinephrine induced release of glycerol from isolated rat fat pads);

(d) inhibiting gastric secretion and reducting undesirable gastrointestinal effects from systematic administration of prostaglandin synthetase inhibitors;

(e) controlling spasm and facilitaing breathing in asthmatic conditions;

(f) decongesting nasal passages;

(g) decreasing bood platelet adhesion (as shown by platelet to glass adhesiveness) and inhibiting blood platelet aggregation and thrombus formation induced by various physical stimuli (e.g., arterial injery) or chemical stimuli (e.g., ATP, ADP, serotinin, thrombin, and collagen);

(h) affecting the reproductive organs of mammals as labor inducers, abortifacients, cervical dilators, regulators of the estrus, and regulators of the menstrual cycle; and (j) accelerating growth of epidermal cells and keratin in animals.

For the PGF$_\alpha$ compound these biological responses include:

(a) increasing blood pressure (as measured, for example, in anesthetized, pentolinium-treated rats);

(b) stimulating smooth muscle (as shown by tests on guinea pig ileum, rabbit duodenum, or gerbil colon);

(c) inhibiting gastric secretion and reducing undesirable gastrointestinal effects from systematic administration of prostaglandin synthetase inhibitors;

(d) controlling spasm and facilitating breathing in asthmatic conditions;

(e) decongesting nasal passages;

(f) decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and (g) affecting the reproductive organs of mammals as labor inducers, abortifacients, cervical dilators, regulators of the estrus, and regulators of the menstral cycle.

For the PGF$_\beta$ compounds these biological responses include:

(a) decreasing blood pressure (as measured, for example, in anesthetized, pentolinium-treated rats);

(b) stimulating smooth muscle (as shown by tests on guinea pig ileum, rabbit duodenum, or gerbil colon);

(c) inhibiting gastric secretion and reducing undesirable gastrointestinal effects from systematic administration of prostaglandin synthetase inhibitors;

(d) controlling spasm and facilitating breathing in asthmatic conditions;

(e) decongesting nasal passages;

(f) decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and (g) affecting the reproductive organs of mammals as labor inducers, abortifacients, cervical dilators, regulators of the estrus, and regulators of the menstrual cycle.

For the PGA compounds these biological responses include:

(a) decreasing blood pressure (as measured, for example, in anesthetized, pentolinium-treated rats);

(b) stimulating smooth muscle (as shown by tests on guinea pig ileum, rabbit duodenum, or gerbil colon);

(c) inhibiting gastric secretion and reducting undesirable gastrointestinal effects from systematic administration of prostaglandin synthetase inhibitors;

(d) controlling spasm and facilitating breathing in asthmatic conditions;

(e) decongesting nasal passages; and (f) increasing kidney blood flow.

For the PGB compounds these biological responses include:

(a) stimulating smooth muscle (as shown by tests on guinea pig ileum, rabbit duodenum, or gerbil colon); and (b) accelerating growth of epidermal cells and keratin in animals.

Because of these biological responses these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The prostaglandins so cited above as hypotensive agents are useful to reduce blood pressure in mammals, including man. For this purpose, the compounds are administered by intravenous infusion at the rate about 0.01 to about 50 $\mu$g. per kg. of body weight per minute or in single or multiple doses or about 25 to 500 $\mu$g. per kg. of body weight total per day.

The PGF$_\alpha$ compounds are useful in increasing blood pressure in mammals, including man. Accordingly, these compounds are useful in the treatment of shock (hemorrhagic shock, endotoxin shock, cardiogenic shock, surgical shock, or toxic shock). Shock is marked by pallor and clamminess of the skin, decreased blood pressure, feeble and rapid pulse, decreased respiration, restlessness, anxiety, and sometimes unconsciousness. Shock usually follows cases of injury and trauma. Expert and fast emergency measures are required to successfully manage such shock conditions. Accordingly, prostaglandins, combined with a pharmaceutical carrier which adapts the prostaglandin for intramuscular, intravenous, or subcutaneous use, are useful, especially in the early stages of shock where the need to increase blood pressure is a critical problem, for aiding and maintaining adequate blood flow, perfusing the vital organs, and exerting a pressor response by constricting veins and raising blood pressure to normal levels. Accordingly, these prostaglandins are useful in preventing irreversible shock which is characterized by a profound fall in blood pressure, dilation of veins, and venus blood pooling. In the treatment of shock, the prostaglandin is infused at a dose of 0.1–25 mcg./kg./min. The prostaglandin may advantageously be combined with known vasoconstrictors; such as phenoxy-benzamine, norepinephrine, and the like. Further, when used in the treatment of shock the prostaglandin is advantageously combined with steroids (such as, hydrocortisone or methylprednisolone), tranquilizers, and antibiotics (such as, lincomycin or clindamycin).

The compounds so cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptons of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, sympton alleviation, and cure of diseases involving abnormal lipid mobilization and high free fatty acid levels, e.g., diabetes mellitus, vascular diseases, and hyperthyroidism.

The prostaglandins so cited above as useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the antiinflammatory prostaglandin synthetase inhibitor. See Partridge et al., U.S. Pat. No. 3,781,429, for a disclusre that the ulcerogenic effect induced by certain non-steroidal anti-inflammatory agents in rats is inhibited by concomitant oral administration of certan prostaglandins of the E and A series, including $PGE_1$, $PGE_2$, $PGE_3$, 13,14-dihydro-$PGE_1$, and the corresponding 11-deoxy-PGE and PGA compounds. Prostaglandins are useful, for example, in reducing the undesirable gastrointestinal effects resulting form systemic administration of indomethacin, phenylbutazone, and aspirin. These adre substances specifically mentioned in Partridge et. al. as non-steroidal, anti-inflammatory agents. These are also known to be prostaglandin synthetase inhibitors.

The anti-inflammatory synthetase inhibitors, for example, indomethacin, aspirin, or phenylbutazone is administered in any of the ways known in the art to alleviate an inflammatory condition, for example, in any dosage regimen and by any of the known routes of systemic administation.

The prostaglandin is administered along with the antiinflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, Further, the prostaglandin can be conveniently administered orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the antiinflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergency situations; by inhalation in the form of aerosols or solutions for nebulizers; or by insufflation in the form of powder. Doeses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The prostaglandins so cited above as useful in mammals, including man, as nasal decongestants are used for this purpose, in a dose range of about 10 μg. to about 10 mg. per ml. of a pharmacologically suitable liquid vehicle or as an aerosol spray, both for topical application.

The prostaglandins so cited above as useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to reat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intrasmuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkets, and rats, for these purposes in order to develop new methods and techniques for organ and limb transplants.

The prostaglandins so cited above as useful in place of oxytocin to induce labor are used in pregnant female aminals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but not so old that regular menstruation has ceased. For that purpose the prostaglandin is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively the prostaglandin is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1–100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The compounds so cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 µg. per ml. of the prostaglandin. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

Several cis-13-prostaglandin analogs are known in the art. See for reference Kluge, A. F., et al., *Journal of the American Chemical Society* 94, 9256 (1972), which discloses cis-13- and 11-deoxy-cis-13PGE$_1$ compounds. See also Bernady, K. F., et al., *Prostaglandins III*, 505 (1973), which discloses racemic 11-deoxy-cis-13-PGE$_1$ compounds. See also U.S. Pat. No. 3,873,607, issued Mar. 25, 1975, which discloses certain 11-deoxy compounds related to those of the instant invention. Finally, see Kluge, A. F., et al., U.S. Pat. No. 3,867,377, *Method of Making* 13-cis *Prostaglandin Derivatives*, issued Feb. 18, 1975.

SUMMARY OF THE INVENTION

This invention provides novel prostaglandin analogs, esters of these analogs, and pharmacologically acceptable salts of these analogs.

This invention further provides lower alkanoates of these analogs.

This invention further provides novel processes for preparing these analogs.

This invention further provides novel chemical intermediates useful in the preparation of these analogs.

In particular, this invention comprises:
(a) a compound of the formula

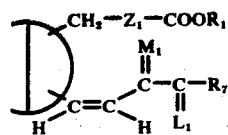

or a mixture comprising that compound and the enantiomer thereof;
wherein D is

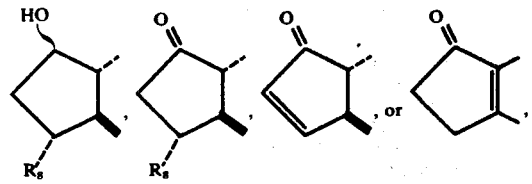

wherein $R_8$ is hydrogen or hydroxy;
wherein $Z_1$ is
1. cis—CH═CH—(CH$_2$)$_g$—C(R$_2$)$_2$—,
2. cis—CH$_2$—CH═CH—(CH$_2$)$_h$—CH$_2$—,
3. —(CH$_2$)$_q$—C(R$_2$)$_2$—,
4. —CH$_2$—O—(CH$_2$)$_g$—CH$_2$—,
5. —(CH$_2$)$_2$—O—(CH$_2$)$_h$—CH$_2$, or
6. —(CH$_2$)$_3$—O—(CH$_2$)$_h$—
wherein $g$ is 2, 3, or 4, $h$ is one, 2, or 3; $q$ is 4, 5, or 6; and $R_2$ is hydrogen or fluoro;
wherein $M_1$ is

or

wherein $R_5$ and $R_6$ are hydrogen or methyl, with the proviso that one of $R_5$ and $R_6$ is methyl only when the other is hydrogen;

wherein $L_1$ is

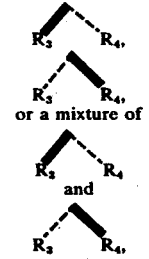

wherein $R_3$ and $R_4$ are hydrogen, methyl, or fluoro, being the same or different, with the proviso that one of $R_3$ and $R_4$ is or fluoro only when the other is hydrogen or fluoro; wherein $R_7$ is
1. —(CH$_2$)$_m$—CH$_3$,

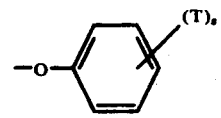

-continued (3)

4. cis—CH=CH—CH$_2$—CH$_3$, wherein $m$ is one to 5, inclusive, T is chloro, fluoro, trifluoromethyl, alkyl of one to 3 carbon atoms, inclusive, or alkoxy of one to 3 carbon atoms, inclusive, and $s$ is zero, one, 2, or 3, the various T's being the same or different, with the proviso that not more than two T's are other than alkyl, with the further proviso that R$_7$ is wherein T and $s$ are as defined above, only when R$_3$ and R$_4$ are hydrogen or methyl, being the same or different;

wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation;

with the further provisos that:

1. R$_7$ is —(CH$_2$)$_m$—CH$_3$ and Z$_1$ is cis—CH=CH—(CH$_2$)$_g$—CH$_2$— or —(CH$_2$)$_q$—CH$_2$—, wherein $m$, $g$, and $q$ are as defined above, only when at least one of R$_3$ and R$_4$ is methyl or fluoro or R$_6$ is methyl; and 2. Z$_1$ is —(CH$_2$)$_q$—CH$_2$—, —(CH$_2$)$_3$—O—CH$_2$—, or cis—CH$_2$—CH=CH—(CH$_2$)$_h$—CH$_2$—, R$_7$ is —(CH$_2$)$_m$—CH$_3$, or cis—CH=CH—CH$_2$CH$_3$, D is wherein W is $\overset{O}{\underset{\|}{}}$, H⟋OH or H⟍OH, and R$_3$ and R$_4$ are hydrogen or methyl, being the same or different, wherein $q$, $h$, and $m$ are as defined above, only when R$_6$ is methyl;

b. a compound of the formula

II or a mixture comprising that compound and the enantiomer thereof, wherein $g$, $m$, R$_1$, and W are as defined above.

The above formulas I and II can be depicted in several alternate ways, and such representations affect the name assigned the configuration of the C-15 hydroxy or methoxy when using the alpha and beta nomenclature. Thus, for the description of the present invention, all formulas drawn herein are patterned after cis-13-PGE$_1$, depicted as follows:

III

Accordingly, the cis-13 prostaglandin analogs herein which are of the same relative configuration at C-15 as the PGE$_1$ obtained from mammalian tissues (e.g., the S configuration, as discussed above), are of the 15β-hydroxy configuration. Likewise the corresponding 15-epimers are of the 15α-hydroxy configuration.

Within the scope of the novel prostaglandin analogs of this invention, there are represented above:

(a) PGE-type compounds when the cyclopentane moiety is:

(b) PGF$_\alpha$-type compounds when the cyclopentane moiety is:

(c) PGF$_\beta$-type compounds when the cyclopentane moiety is:

(d) PGA-type compounds when the cyclopentane moiety is:

(e) PGB-type compounds when the cyclopentane moiety is:

(f) 11-deoxy-PGE-type compounds when the cyclopentane moiety is:

(g) 11-deoxy-PGF$_\alpha$-type compounds when the cyclopentane moiety is:

-continued

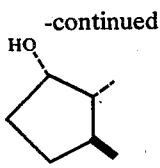

and (h) 11-deoxy-PGF$_\beta$-type compounds when the cyclopentane moiety is:

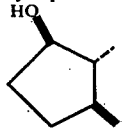

Those prostaglandin analogs herein wherein $Z_1$ is cis—CH=CH—(CH$_2$)$_g$—C—(R$_5$)$_2$— are named as PG$_2$ compounds. When R$_5$ is fluoro these compounds are further characterized as 2,2-difluoro PG-type compounds. When $g$ is 3 or 4, the prostaglandin analogs so described are 2a-homo or 2a,2b-dihomo compounds, since in this event the carboxy terminated side chain contains 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are referred to as C-2a and C-2b, counting from the C-2 to the C-3 position.

Further when $Z_1$ is —(CH$_2$)$_q$—C(R$_2$)—, wherein $q$ is as defined above, the compounds so described are PG$_1$ compounds. When $q$ is 5 or 6, the 2a-homo and 2a,2b-dihomo compounds are described as is discussed in the preceding paragraph.

When $Z_1$ is —CH$_2$—O—(CH$_2$)$_g$—CH$_2$— the compounds so described are named as 5-oxa-PG$_1$ compounds. When $g$ is 3 or 4, the compounds so described are 2a-homo or 2a,2b-dihomo compounds, respectively, as discussed above.

When $Z_1$ is —(CH$_2$)$_2$—O—(CH$_2$)$_h$—CH$_2$—, wherein $h$ is as defined above, the compounds so described are named as 4-oxa-PG$_1$ compounds. When $h$ is 2 or 3, the compounds so described are additionally characterized as 2a-homo or 2a,2b-dihomo compounds, respectively, as is discussed above.

When $Z_1$ is —(CH$_2$)$_3$—O—(CH$_2$)$_h$—, wherein $h$ is as defined above, the compounds so described are named as 3-oxa-PG$_1$ compounds. When $h$ is 2 or 3, the compounds so described are further characterized as 2a-homo or 2a,2b-dihomo compounds, respectively, as is discussed above.

When $Z_1$ is cis—CH$_2$—CH=CH—(CH$_2$)$_h$—CH$_2$—, wherein $h$ is as defined above, the compounds so described are named cis-4,5-didehydro-PG$_1$ compounds. When $h$ is 2 or 3, the compounds so described are further characterized as 2a-homo or 2a,2b-dihomo compounds, respectively, as discussed above.

All the novel prostaglandin analogs of this invention contain a cis—CH=CH— moiety at the C-13 to C-14 position. Accordingly, the novel prostaglandin type compounds of this invention are referred to as cis-13 compounds.

When R$_7$ is —(CH$_2$)$_m$—CH$_3$, wherein $m$ is as defined above, the compounds so described are named as 19,20-dinor, 20-nor, 20-methyl, or 20-ethyl compounds when $m$ is one, 2, 4, or 5, respectively.

When R$_7$ is

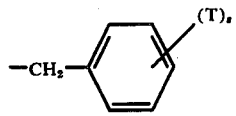

wherein T and $s$ are as defined above, the compounds so described are named as 17-phenyl-18,19,20-trinor compounds, when $s$ is 0. When $s$ is one, 2, or 3, the corresponding compounds are named as 17-(substituted phenyl)-18,19,20-trinor compounds.

When R$_7$ is

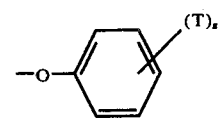

wherein T and $s$ are as defined above, and neither R$_3$ nor R$_4$ is methyl, the compounds so described are named as 16-phenoxy-17,18,19,20-tetranor compounds, when $s$ is zero. When $s$ is one, 2, or 3, the corresponding compounds are named as 16-(substituted phenoxy)-17,18,19,20-tetranor compounds. When one and only one of R$_3$ and R$_4$ is methyl or both R$_3$ and R$_4$ are methyl, then the corresponding compounds wherein R$_7$ is as defined in this paragraph are named as 16-phenoxy or 16-(substituted phenoxy)-18,19,20-trinor compounds or 16-methyl-16-phenoxy or 16-(substituted phenoxy)-18,19,20-trinor compounds, respectively.

When R$_7$ is cis—CH=CH—CH$_2$—CH$_3$, the compounds so described are PG$_3$ or 17,18-didehydro-PG$_1$ compounds depending on whether $Z_1$ is cis—CH=λ CH—(CH$_2$)$_g$—C(R$_2$)$_2$ or another moiety, respectively.

When at least one of R$_3$ and R$_4$ is not hydrogen then (except for the 16-phenoxy compounds discussed above) there are described the 16-methyl (one and only one of R$_3$ and R$_4$ is methyl), 16,16-dimethyl (R$_3$ and R$_4$ are both methyl), 16-fluoro (one and only one of R$_3$ and R$_4$ is fluoro), 16,16-difluoro (R$_3$ and R$_4$ are fluoro) compounds. For those compounds wherein R$_3$ and R$_4$ are different, the prostaglandin analogs so represented contain an asymmetric carbon atom at C-16. Accordingly, two epimeric configurations are possible: (16S) and (16R). Further, there is described by this invention the C-16 epimeric mixture: (16RS).

When R$_5$ is methyl, the compounds so described are named as 15-methyl compounds. When R$_6$ is methyl, the compounds so described are named as 15-methyl ether compounds.

Some formulas of 13-cis-cyclopentane derivatives described hereinafter contain a moiety of the formula:

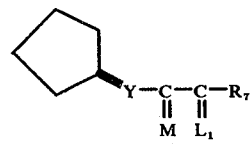

wherein the cyclopentane ring is variously substituted, wherein M is variously defined according to the subscripts provided herein; wherein L$_1$ and R$_7$ is as defined above; and wherein Y is cis—CH=CH—. Optionally the above formula is depicted with one or both of L$_1$ and M above the carbon atom to which it is attached, e.g., as follows:

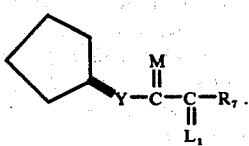

When either of the above representations is employed, it is hereby defined to indicate the following convention with respect to the representation of the cis-13 double bond:

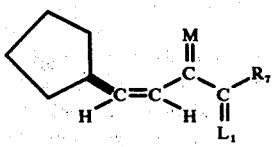

Further in employing this convention when M is, for example,

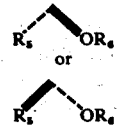

then the corresponding representations:

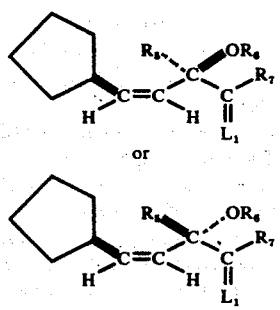

are intended, respectively. Accordingly all the formulas herein which represent 13-cis cyclopentane derivatives are depicted by the same convention as that for the cis-13-PGE$_1$ when drawn as follows:

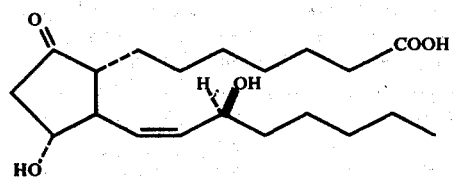

Thus, by this convention the (15S)-hydroxy of cis-13-PGE$_1$ is in the beta configuration.

cis-13-PG-type compounds as drawn herein which have an hydroxy or methoxy at C-15 in the alpha configuration are of the opposite relative stereochemical configuration at C-15 as that of cis-13-PGE$_1$, and are therefore named as 15-epi compounds. When the beta hydroxy or methoxy configuration is present, no special designation of this stereochemistry is provided.

Accordingly, 15-epi-16,16-difluoro-cis-13-PGF$_2$ $\alpha$ is depicted herein as follows:

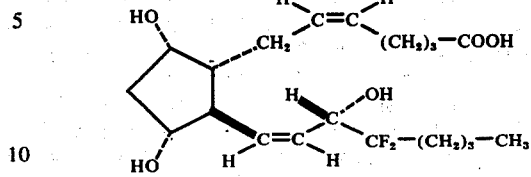

Alternate representations of cis-13-PGE$_1$ affect the depiction of C-15 as an alpha or beta hydroxy. Thus, by a representation contrary to the instant convention, cis-13-PGE$_1$ appears as follows:

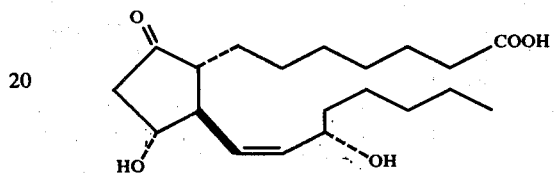

Accordingly, care must be taken to consistently draw the formulas herein such that the C-15 carbon atom is properly represented, i.e., all 15-epi-PG's are 15α-OH.

Further, the 15-epi compounds are distinguished from the other C-15 epimer by conventional techniques of determining absolute configuration about an assymetric carbon atom. For example, 15-epi-16,16-dimethyl-cis-13-PGE$_2$, methyl ester and 15-epi-16,16-difluoro-cis-13-PGE$_2$, methyl ester are distinguished from the respective 15β-hydroxy epimers in that the 15-epi compounds are more polar as shown by silica gel thin layer chromatographic analysis.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 1-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexnyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of

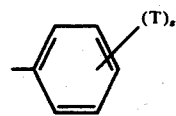

wherein T is alkyl of one to 3 carbon atoms, inclusive, fluoro, chloro, trifluoromethyl, or alkoxy of one to 3 carbon atoms, inclusive; and s is zero, 1, 2, or 3, with the proviso that not more than two T's are other than alkyl, are phenyl, (o-, m-, or p-(tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloroo-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, o-, m-, or p-trifluoromethylphenyl, (o-, m-, or p-)methoxyphenyl, (o-, m-, or p-)ethoxyphenyl, (4- or 5-)chloro-2-methoxyphenyl, and 2,4-dichloro(5- or 6-)methoxyphenyl.

The novel prostaglandin analogs of this invention correspond to the prostaglandins described above, in that the novel prostaglandin analogs exhibit prostaglandin-like activity.

Specifically the PGE- and 11-deoxy-PGE-type compounds of this invention correspond to the PGE compounds described above, in that these novel PGE- and 11-deoxy-PGE-type compounds are useful for each of the above-described purposes for which the PGE compounds are used, and are used in the same manner as the PGE compounds, as described above.

The $PGF_\alpha$ - and 11deoxy-$PGF_\alpha$ -type compounds of this invention correspond to the $PGF_\alpha$ compounds described above, in that these novel $PGF_\alpha$ - and 11-deoxy-$PGF_\alpha$ -type compounds are useful for each of the above described purposes for which the $PGF_\alpha$ compounds are used, and are used in the same manner as the $PGF_\alpha$ compounds, as described above.

The $PGF_\beta$ - and 11-deoxy-$PGF_\beta$ -type compounds of this invention correspond to the $PGF_\beta$ compounds described above, in that these novel $PGF_\beta$ - and 11-deoxy-$PGF_\beta$ -type compounds are useful for each of the above-described purposes for which the $PGF_\beta$ compounds are used, and are used in the same manner as the $PGF_\beta$ compounds, as described above.

The PGA-type compounds of this invention correspond to the PGA compounds described above, in that these novel PGA-type compounds are useful for each of the above described purposes for which the PGA compounds are used, and are used in the same manner as the PGA compounds, as described above.

The PGB-type compounds of this invention correspond to the PGB compounds described above, in that these PGB-type compounds are useful for each of the above described purposes for which the PGB compounds are used, and are used in the same manner as the PGB compounds, as described above.

The prostaglandins described above, ae all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, buccally, or rectally in those cases wherein the corresponding prostaglandin is effective only by the intravenous, intramuscular, or subcutaneous injection or injusion methods of administration indicated above as uses of these prostaglandins. These alternate routes of administration are advantageous because they facilitate maintaining uniform levels of these compounds in the body with fewer, shorter, or smaller doses, and make possible self-administration by the patient.

Accordingly, the novel prostaglandin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injection or infusion, sterile aqueous isotonic solutions are preferred. For that purpose it is preferred because of increased water solubility that $R_1$ in the novel compounds of this invention by hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art ae used. For tissue implants, a sterile tablet or silicone rubber capsule or other object containing or impregnated with the substance is used.

The chemical structure of the novel 11-deoxy-13-cis-PGE-type compounds of this invention renders them less sensitive to dehydration and rearrangement than the corresponding prostaglandins, and these compounds accordingly exhibit a surprising and unexpected stability and duration of shelf life.

The novel PG analogs of this invention are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, n-(p-tert-amylphenyl)-diethanolamine, galactamine, N-methylgycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel PG analogs of this invention used for the purposes described above in free hydroxy form or also in the form wherein the hydroxy moieties are transformed to lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

To obtain the optimum combination of biological response specificity, potency, and duration of activity, certain compounds within the scope of this invention are preferred.

CHART A

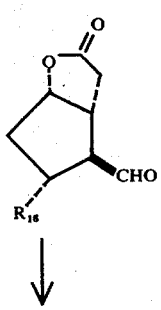   XXI

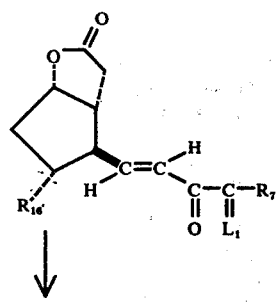   XXII

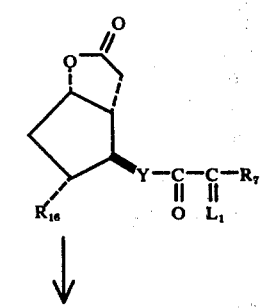   XXIII

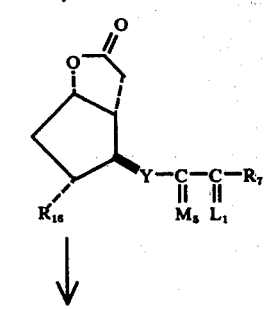   XXIV

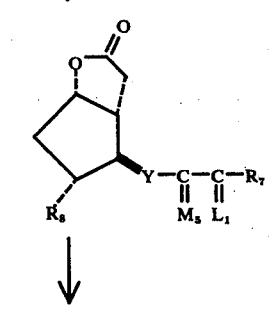   XXV

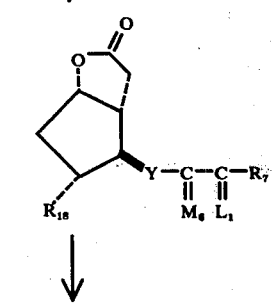   XXVI

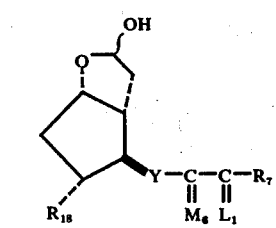   XXVII

CHART B

XXXI

XXXII

XXXIII

XXXIV

XXXV

CHART C

XLI

XLII

XLIII

CHART D

LI

LII

LIII

LIV

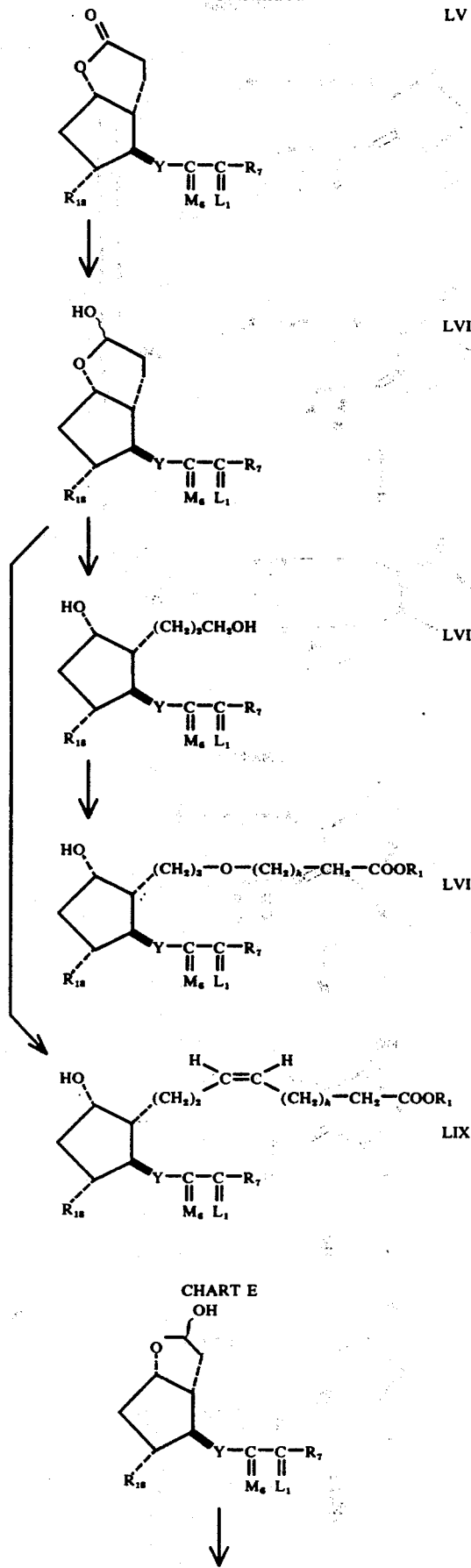
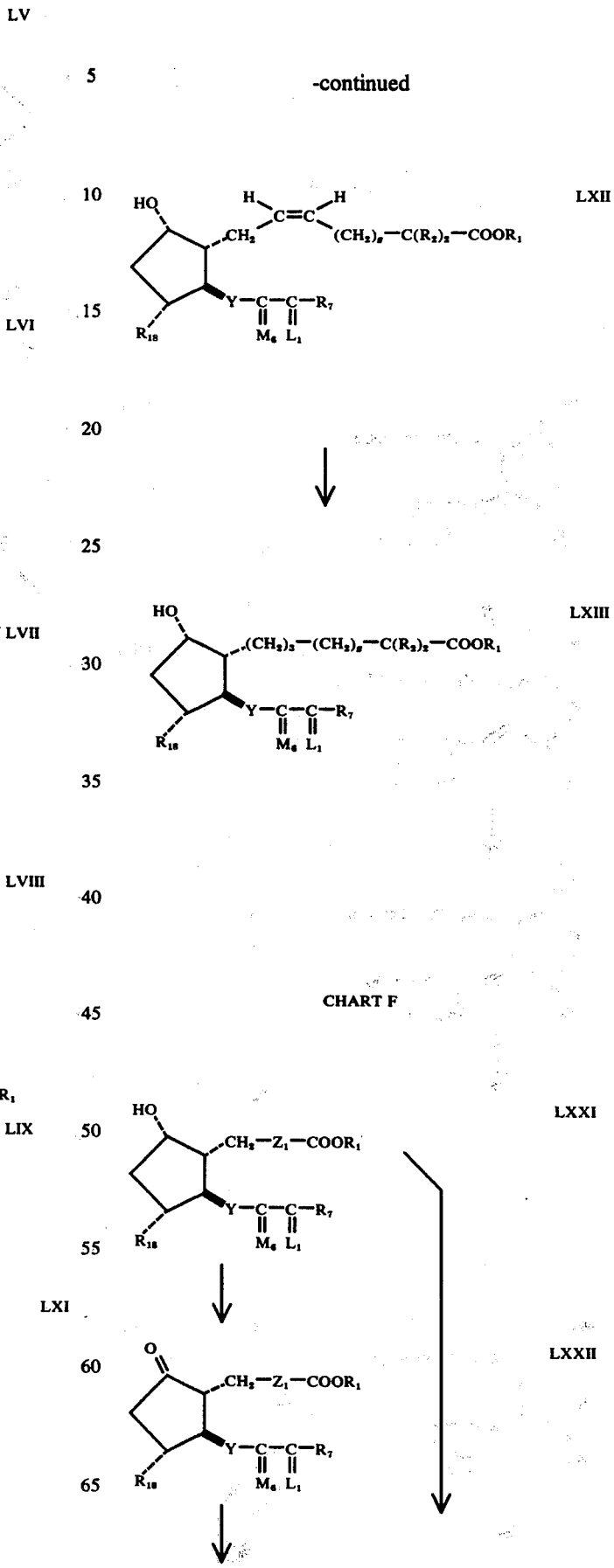
CHART F

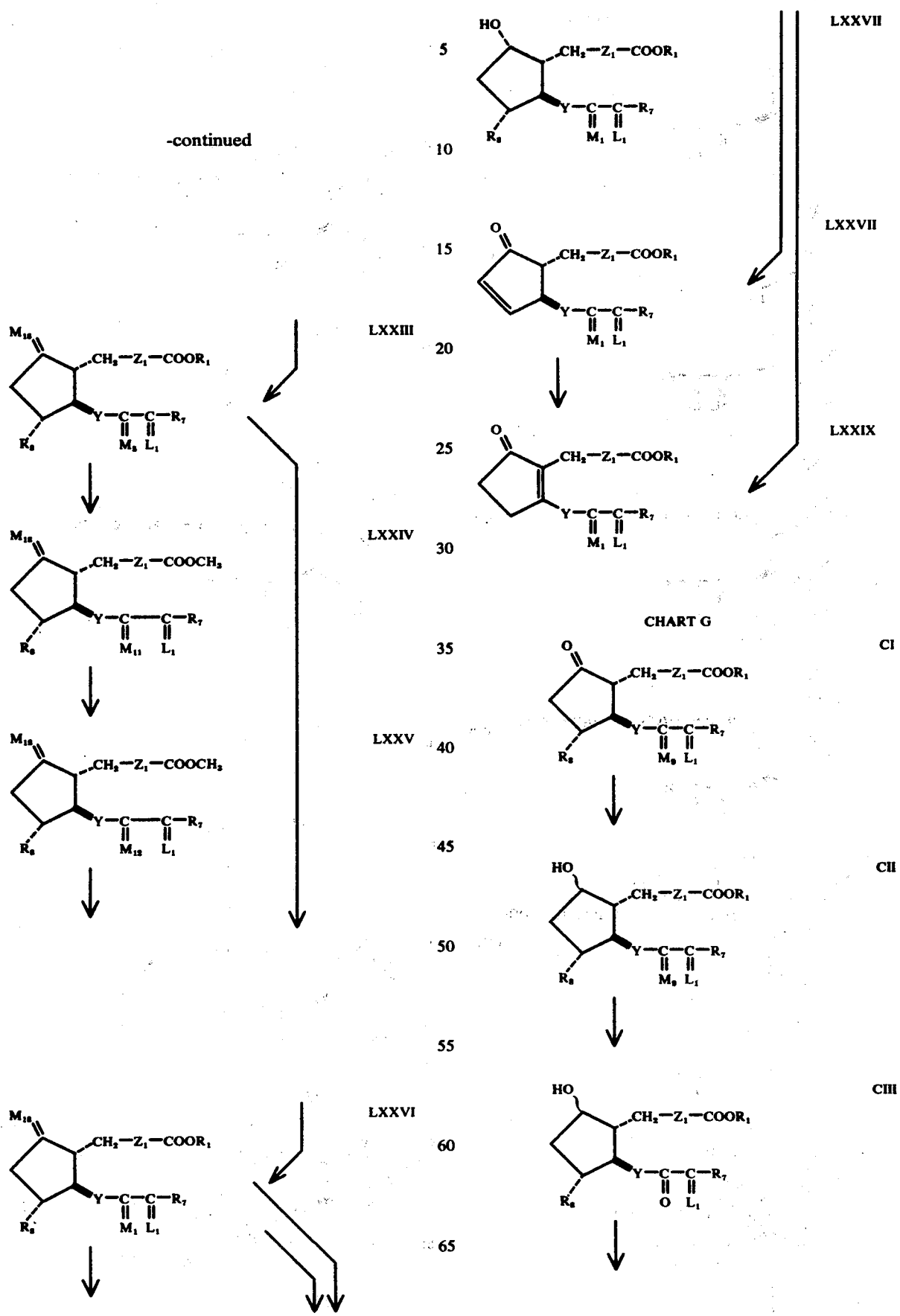

CIV
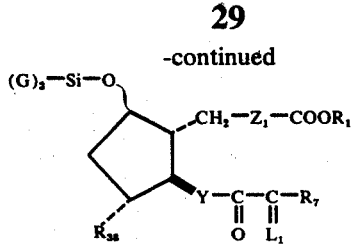
CV
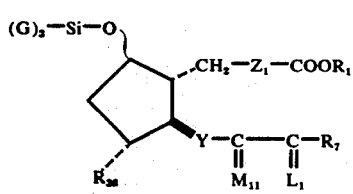
CVI
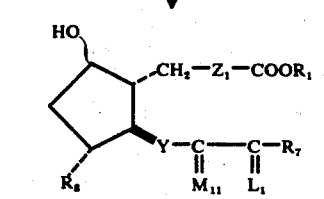
CVII
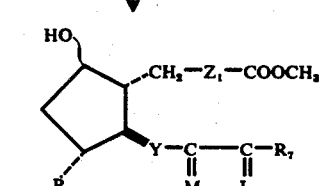
CVIII
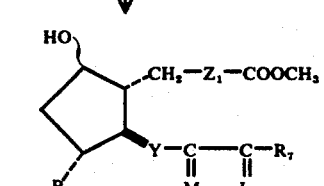
CIX
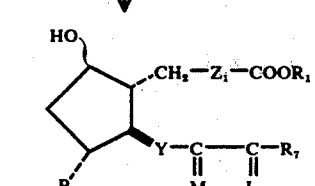
CXXI
CHART H
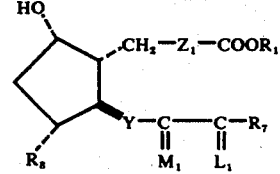
CXXII
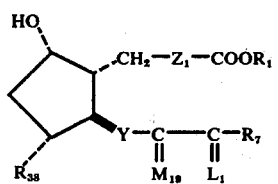
CXXIII
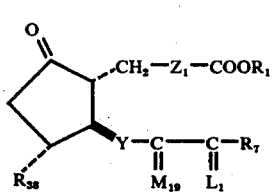
CXXIV
CHART I
CXXXI
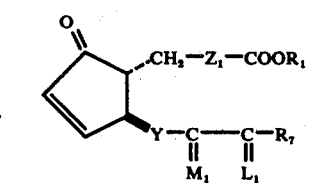
CXXXII
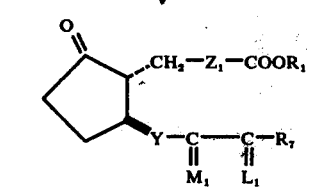
CXXXIII
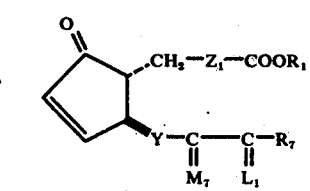

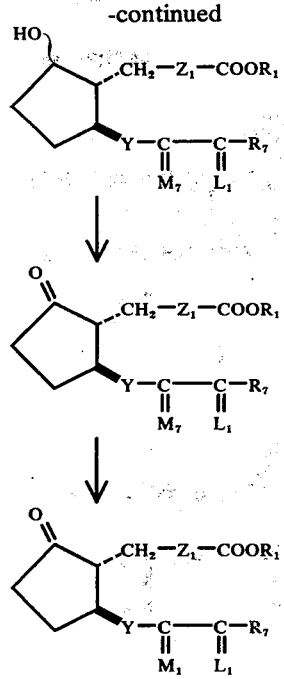

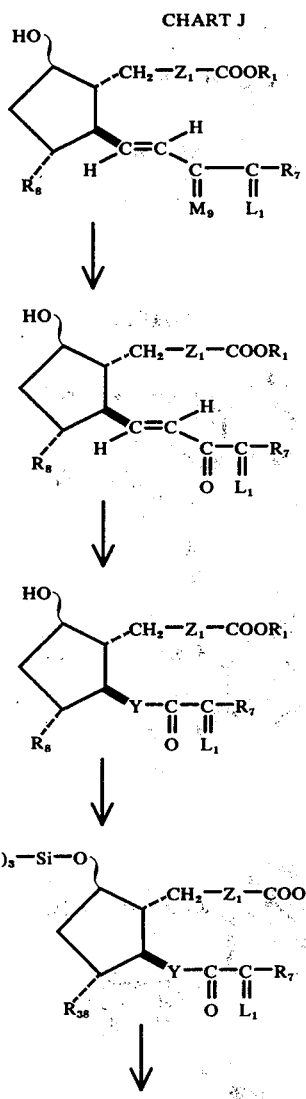

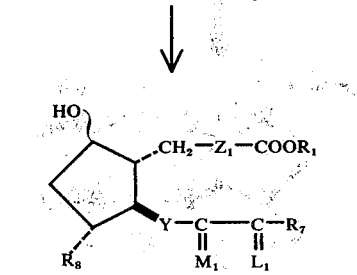

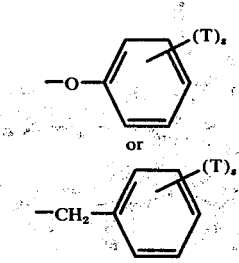

It is preferred that the carboxy-terminated side chain contain either 7 or 9 carbon (or carbon and oxygen) atoms, especially preferred that it contain 7, i.e., the natural chain length of the prostaglandins. Further when the other side chain contains $-(CH_2)_m-CH_3$, it is preferred that $m$ be 3. For these compounds wherein $R_7$ is

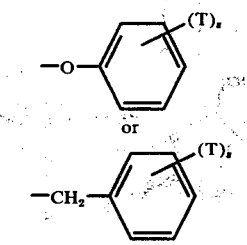

it is preferred that $s$ be zero or one and T be chloro, fluoro, or trifluoromethyl.

For those compounds wherein at least one of $R_3$ and $R_4$ is methyl or fluoro, it is preferred tht $R_5$ and $R_6$ both be hydrogen. For those compounds wherein at least one of $R_5$ and $R_6$ is methyl, it is preferred that $R_3$ and $R_4$ both be hydrogen. For those compounds wherein $R_7$ is it is preferred tht $R_3$, $R_4$, $R_5$, and $R_6$ all be hydrogen.

For those compounds wherein an oxa is substituted for a methylene (i.e., —O— for —$CH_2$—), it is preferred that such substitution occur at C-5.

It is further preferred that the 15-hydroxy or 15-methoxy be of the 15-epi configuration, i.e. that the hydroxy be in the alpha configuration when the formulas of the novel cis-13-PG analogs are as drawn herein.

The Charts herein describe methods whereby the novel prostaglandin analogs of this invention are prepared.

With respect to the Charts $R_1$, $R_2$, $R_7$, $M_1$, $L_1$, $Z_1$, $h$, and $g$ are as defined above; Y is cis—CH=CH—. $M_5$ is

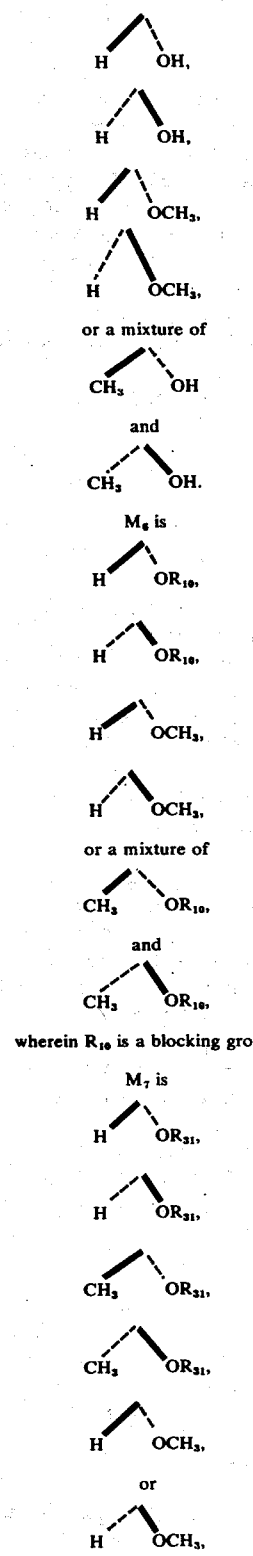

wherein $R_{10}$ is a blocking group.

$M_7$ is wherein $R_{31}$ is a blocking group as defined hereinbelow in the text accompanying Chart 1.

$M_9$ is

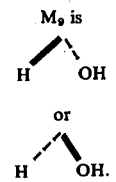

or

$M_{11}$ is a mixture of and $M_{12}$ is or

$M_{18}$ is $\overset{O}{\|}$ or

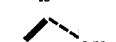

$M_{19}$ is or when $R_6$ is methyl, and

or when $R_6$ is hydrogen, wherein $R_{39}$ is hydrogen or methyl, being the same as $R_5$. $R_8$ is hydrogen or hydroxy.

$R_{16}$ is hydrogen or —$OR_9$, wherein $R_9$ is an acyl protecting group. $R_{18}$ is hydrogen or —$OR_{10}$, wherein $R_{10}$ is as defined above. $R_{22}$ is methyl or ethyl. $R_{26}$ is hydrocarbyl, including alkyl, aralkyl, cycloalkyl, and the like. Examples of these hydrocarbyl groups include 2-methylbutyl, isopentyl, heptyl, octyl, nonyl, tridecyl, octadecyl, benzyl, phenethyl, p-methylphenethyl, 1-methyl-3-phenylpropyl, cyclohexyl, phenyl, and p-methylphenyl.

G is alkyl or one to 4 carbon atoms, aralkyl of 7 to 12 carbon atoms, phenyl, or phenyl substituted with one or 2 fluoro, chloro, or alkyl of one to 4 carbon atoms, with the proviso that in the —Si—$(G)_3$ moiety the various G's are the same or different. $R_{38}$ is hydrogen or —O—Si—$(G)_3$, wherein G is as defined above.

$R_9$ is an acyl protecting group. Acyl protecting groups according to $R_9$, include:
(a) Benzoyl;
(b) Benzoyl substituted with one, to 5 alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;

(c) Benzoyl substituted with alkoxycarbonyl of 2 to 5 carbon atoms, inclusive;

(d) Naphthoyl;

(e) Naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused aromatic rings does not exceed 10 carbon atoms, with the further proviso that the various substituents are the same or different; or (f) Alkanoyl of 2 to 12 carbon atoms, inclusive.

In preparing these acyl derivatives of a hydroxy-containing bicyclic lactone herein, methods generally known in the art are employed. Thus, for example, an aromatic acid of the formula $R_9OH$, wherein $R_9$ is as defined above (e.g, benzoic acid), is reacted with the hydroxy-containing bicyclic lactone in the presence of a dehydrating agent, e.g. sulfuric acid, zinc chloride, or phosphoryl chloride; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxyl-containing bicyclic lactone in the presence of a hydrogen chloride scavenger, e.g. a tertiary amine such as pyridine triethylamine of the like. The reaction is carried out under a variety of conditions, using procedures generally known in the art. Generally mild conditions are employed: 20°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9OH$), anhydrides (($R_9)_2O$), or acyl chlorides ($R_3Cl$): benzoyl; substituted benzoyl, e.g., 2-, 3-, or 4-)-methylbenzoyl, (2-, 3-, or 4-)-ethylbenzoyl, (2-, 3-, or 4-)-isopropylbenzoyl, (2-,3-, or 4-)-tert-butylbenzoyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching cite.

The acyl protecting groups, according to $R_9$, are removed by deacylation. Alkali metal carbonates are employed effectively at ambient temperature for this purpose. For example, potassium carbonate in methanol at about 25° C. is advantageously employed.

Those blocking groups within the scope of $R_{10}$ are any group which replaces a hydroxy hydrogen and is neither attacked nor as reactive to the reagents used in the transformations used herein as an hydroxy is and which is subsequently replaceable with hydrogen in the preparation of the prostaglandin-type compounds. Several blocking groups are known in the art, e.g. tetrahydropyranyl and substituted tetrahydropyranyl. See for reference E. J. Corey, *Proceedings of the Robert A. Welch Foundation Conferences on Chemical Research*, 12, *Organic Synthesis*, pgs. 51–79 (1969). Those blocking groups which have been found useful include a. Tetrahydropyranyl;

b. Tetrahydrofuranyl; and c. A group of the formula $$-C(OR_{11})(R_{12})-CH(R_{13})(R_{14}),$$

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$or$-(CH_2)_b-O-(CH_2)_c$, wherein $a$ is 3, 4, or 5, $b$ is one, 2, or 3, and $c$ is one, 2, or 3, with the proviso that $b$ plus $c$ is 2, 3 or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as p-toluenesulfonic acid or pyridine hydrochloride. The dihydropyran is used in large stoichoimetric excess, preferably 4 to 10 times the stoichoimetric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula $$-C(OR_{11})(R_{12})-CH(R_{13})(R_{14}),$$

wherein $R_{11}$, $R_{12}$, $R_{13}$, and $R_{14}$ are as defined above, the appropriate reagent is a vinyl ether, e.g. isobutyl vinyl ether or any vinyl ether of the formula $$C(OR_{11})(R_{12})=C(R_{13})(R_{14}),$$

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., *Journal of the Chemical Society* 89, 3366 (1967). The reaction conditions for such vinyl ethers and unsaturated compounds are similar to those for dihydropyran above.

The blocking groups according to $R_{10}$ are removed by mild acidic hydroylsis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

With respect to Chart A the formula XXI compound is known in the art. This compound is available in either optically active or racemic form. The formula XXI compound in racemic form may be transformed into corresponding optically active compound by methods known in the art.

The formula XXII compound is prepared from the formula XXI compound by a Wittig alkylation. Reagents known in the art or prepared by methods known in the art are employed. The transenone lactone is obtained stereospecifically. See for reference D. H. Wadsworth, et al., *Journal of Organic Chemistry* 30, 680 (1965).

In the preparation of the formula XXII compound, certain phosphonates are employed in the Wittig reaction. These phosphonates are of the general formula

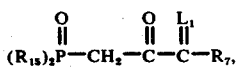

wherein $L_1$ and $R_7$ are as defined above and $R_{15}$ is alkyl of 1 to 8 carbon atoms, inclusive.

Phosphonates of the above general formula are prepared by methods known in the art. See Wadsworth, et al. as cited above.

Conveniently the appropriate aliphatic acid ester is condensed with the anion of the dimethyl methylphosphonate as produced using n-butyllithium. For this purpose, acids of the general formula

are employed in the form of their lower alkyl esters, preferably methyl or ethyl. The methyl esters for example are readily obtained by reaction of the corresponding acids with diazomethane.

For example, when $R_7$ is

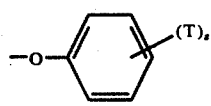

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-, (o-, m-, or p-)chlorophenoxy-, (2,3-, 2,4-, 2,5-, 2,6-, 3,4-, or 3,5-)dichlorophenoxy-, (4- or 6-chloro-o-tolyloxy-, phenoxy-, (o-, m-, or p-)tolyloxy, 3,5-xylyloxy-, or m-trifluoromethylphenoxy-.

Finally there are available many 2-methyl-2-phenoxy- or (2-substituted)phenoxypropionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_1$ is: phenoxy-, (o-, m-, or p-)chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the (T)$_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is benzyl or substituted benzyl.

For example, when $R_3$ and $R_4$ of the $L_1$ moiety are both hydrogen there are available the following phenyl or substituted phenyl propionic acids: (o-, m-, or p-)-chlorophenyl-, p-fluorophenyl-, m-trifluoromethyphenyl-, (o-, m-, or p-)methylphenyl-, (o-, m-, or p-)methoxyphenyl-, (2,4-, 2,5-, or 3,4-)dichlorophenyl-, (2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl there are available, for example, the following 2-methyl-3-phenyl or substituted phenyl propionic acids: phenyl, o-chlorophenyl-, (o-, or p-)methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both $R_3$ and $R_4$ are methyl there are available for example, the following 2,2-dimethyl-3-phenyl or substituted phenyl propionic acids: phenyl- and p-methylphenyl.

When one and only one of $R_3$ and $R_4$ is fluoro, there is available, for example, 2-fluoro-3-phenyl propionic acid.

Phenyl substituted acids (as above wherein $R_7$ is benzyl) are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran) with the appropriately substituted benzyl chloride. Thus, the above acid is obtained by the following reaction:

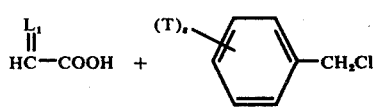

-continued

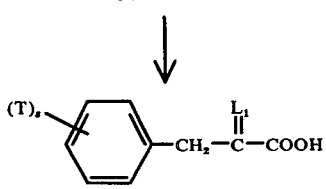

The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available the following 2-methyl alkanoic acids: butyric, pentanoic, hexanoic, heptanoic, and octanoic.

For example, when both $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxo-alkanoic acids, i.e. butyric, pentanoic, hexanoic, heptanoic, and octanoic. The transformation of these 2-oxo-alkanoic acids to the corresponding 2,2-difluoro alkanoic acids proceeds by methods known in the art, using known ketonic fluorinating reagents. For example, $MoF_6 \cdot BF_3$ is advantageously employed in the fluorination.

Many acids of the above general formula wherein $R_7$ is butenyl are readily available in the art. For example, cis-3-hexenoic acid and 2-methyl-cis-3-hexenoic acid are available. The various cis-3-hexenoic acids within the scope of the general formula are alternatively prepared by methods known in the art.

For example, when $R_3$ and $R_4$ of the $L_1$ moiety are both fluoro, the 2,2-difluoro-cis-3-hexenoic acid is prepared from the corresponding 2-oxo-cis-3-hexenoic acid by reaction of the 2-oxo acid with known ketonic fluorination agents (e.g., $MoF_6 \cdot BF_3$).

The above alkenoic acids are prepared by reaction of a mixture of the appropriate 2-methyl or 2-fluoro substituted acetic or propionic acid, a secondary amine (e.g., diisopropyl amine), n-butyllithium, and a suitable organic diluent (tetrahydrofuran) with 1-bromo-cis-3-pentene. This reaction proceeds smoothly at about 0° C., and the product is recovered using conventional methods.

The formula XXIII compound is prepared from the formula XXII compound by photoisomerization, followed by separating the resulting trans-cis mixture of isomers. The photoisomerization proceeds by use of a conventional photon generating source which is capable of producing photons whose wavelength is between about 2800 to 4000 Angstroms. It is preferred to use a conventional photon generating source which is capable of producing photons whose wave length is about 3500 Angstroms. Irradiation continues until a equilibrium mixture of cis and trans isomers is obtained. The progress of the photoisomerization is conveniently monitored by conventional methods, e.g. silica gel thin layer chromatography (TLC). The resulting equilibrium mixture is then separated using convention methods. For example, silica gel chromatography is advantageously employed.

The formula XXIV compound is prepared from the formula XXIII 3-oxo bicyclic lactone by transformation of the 3-oxo-moiety to the $M_5$ moiety.

The above 3-oxo bicyclic lactone is transformed to the corresponding 3α- or 3β-hydroxy bicyclic lactone, wherein $M_5$ is

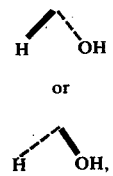

by reduction of the 3-oxo-moiety, followed by separation of the 3α- and 3β-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium(tri-tert-butoxy)-aluminum hydride, metal trialkyl borohydrides, e.g. sodium trimethoxy borohydride, lithium borohydride, and the like. In those cases in which carbon-carbon double bond reduction need not be avoided, the boranes, e.g. disiamylborane (bis-3-methyl-2-butyl borane) are alternatively employed.

For the production of C-15 epimerically pure prostaglandins, the 15-epi compound is separated from the mixture by methods known in the art. For example, silica gel chromatography is advantageously employed.

For the transformation of the 3-oxo-bicyclic lactone to the corresponding 3-methoxy bicyclic lactone, the 3-hydroxy moiety of the 3-hydroxy bicyclic lactone prepared above is alkylated, employing methods known in the art.

The alkylation described in the above paragraph proceeds, for example, by reaction of the 3-hydroxy bicyclic lactone with diazomethane, preferably in the presence of a Lewis acid (e.g., boron trifluoride etherate, aluminum chloride, or fluoboric acid). See for reference Fieser, et al., "Reagents for Organic Synthesis," John Wiley and Sons, New York, N. Y., (1967), especially page 191. The reaction is carried out by mixing a solution of the diazomethane in a suitable inert diluent, preferably diethyl ether, with the 3-hydroxy bicyclic lactone prepared above. This reaction proceeds at about 25° C.

An alternate method for the alkylation of the 3-hydroxy compound is by reaction with methanol in the presence of boron trifluoride etherate. Thus, the methanol and boron trifluoride etherate are reacted with the 3-hydroxy compound at 25° C., the reaction being monitored conveniently by thin layer chromatography (TLC).

The 3-oxo bicyclic lactone is transformed into the corresponding (3RS)-3-methyl bicyclic lactone wherein $M_5$ is a mixture of

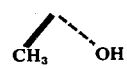

-continued
and

by reaction of the 3-oxo bicyclic lactone with a Grignard reagent, $CH_3MgHal$, wherein Hal is chloro, bromo, or iodo. The Grignard complex is thereafter hydrolyzed, for example, using saturated aqueous ammonium chloride as is known in the art. An alternate method for transforming the 3-oxo compound to a 3(RS)-3-methyl compound is by reaction of the 3-oxo bicyclic lactone with trimethylaluminum.

The preferred method for separation of these (3RS)-3-methyl epimers is by separation of the corresponding C-15 epimers of the PG-type, methyl esters using silica gel chromatography or high pressure liquid chromatography (HPLC). The formula XXV compound is prepared from the formula XXIV compound by deacylation, as described above. The formula XXVI compound is then prepared from the formula XXV compound by replacing any free hydroxy moieties with blocking groups according to $R_{10}$ by the procedure described above. The formula XXVII compound is then prepared from the formula XXVI compound by reduction of the formula XXVI lactone to a lactol. Methods known in the art are employed. For example, diisobutylaluminum hydride is employed at $-60°$ to $-70°$ C.

Chart B provides a method whereby the formula XXXI lactol, prepared according to Chart A, is transformed into a corresponding formula XXXV 3-oxa-$PGF_{1\alpha}$ -type compound.

The formula XXXII compound is obtained from the formula XXXI lactol by the Wittig reaction, with an (alkoxymethylene)triphenyl phosphorane, $R_{22}OO-C-CH=P(C_6H_5)_3$, wherein $R_{22}$ is as defined above. The reaction is conveniently carried out at 25° C. using methods and reactants known in the art.

The formula XXXIII compound is then obtained by reduction of the ethylenic group in the carboxyl-containing side chain. For this purpose a reducing agent is used which does not reduce the Y group, for example hydrogen in the presence of a catalyst such as tris)triphenylphosphine)rhodium (1) chloride. Mild conditions are sufficient such as a pressure of 1-3 atmospheres and temperatures of 0° to 40° C.

The formula XXXIV alcohol is obtained from the formula XXXIII compound by reduction, for example with lithium aluminum hydride or lithium trimethoxy aluminum hydride. A solvent such as diethyl ether or tetrahydrofuran is conveniently used.

The formula XXXV compound is obtained by a Williamson synthesis, condensing the formula XXXIV alcohol with a haloalkanoate, $Hal-(CH_2)_h-COOR_1$, wherein Hal is chloro, bromo, or iodo and $h$ and $R_1$ as above defined, in the presence of a base. For the base, there is used, for example, n-butyllithium, phenyllithium, triphenylmethyllithium, sodium hydride, or potassium t-butoxide. It is preferred that only one molecular equivalent of the base be used. The alkanoate is employed in about 100% stoichoimetric excess. Instead of a haloalkanoic acid ester, a salt, for example lithium chloroacetate is useful. After the condensation, the salt is transformed to the XXXV compound by methods known in the art. The condensation is conveniently run in a solvent such as dimethyl formamide, tetrahydrofuran, dimethyl sulfoxide, or hexamethylphosphoramide.

With respct to Chart C a method is provided whereby the formula XLI lactol is transformed into the correponding formula LXIII 5-ox -$PGF_{1\alpha}$ -type compound. The formula XLII alcohol is obtained upon reduction of the formula LXI lactol, for example, with aqueous methanolic or ethanolic sodium borohydride. Alternatively, and preferably, the formula XLII compound is obtained by a one step reduction of the formula XLI lactone, for example, with lithium aluminum hydride or diisobutyl aluminum hydride at a temperature ranging from 0° to 35° C. For preparing the formula XLIII compound a Williams synthesis is employed. For example, the formula XLII compound is condensed with a haloalkanoate within the scope of

wherein Hal is chloro, bromo, or iodo and g is as defined above. Normally the reaction is done in the presence of a base such as n-butyllithium, phenyllithium, trimethyllithium, sodium hydride, or potassium t-butoxide.

Alternatively and preferably, an ortho-4-bromoalkanoate is employed. Such reagents are available or are prepared by methods known in the art, for example, from the appropriate haloitryl by way of the corresponding imino ester hydrohalide as illustrated hereinafter.

The condensation is conveniently run in a solvent, such as tetrahydrofuran or dimethyl sulfoxide or especially if an organolithium compound is employed, preferably in dimethylformamide or hexamethylphosphoramide. The reaction proceeds smoothly at $-20°$ to 50° C., but is preferably performed at ambient temperature. Following the condensation the formula XLIII compound is obtained by methods known in the art, for example, by hydrolysis in cold dilute mineral acid.

Chart D provides a method whereby the formula LI compound is transformed into the corresponding formula LVIII 4-oxo-$PGF_{1\alpha}$ -type compound or formula LIX cis-4,5-didehydro-$PGF_{1\alpha}$ -type compound.

The formula LI compound undergoes condensation to form the formula LII enol. For this purpose a hydrocarbyloxy, and preferably an alkoxymethylenetriphenylphosphorane is useful. See for reference, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below $-10°$ C. The formula LI lactol is mixed with the above reagent and the condensation proceeds smoothly within the temperature range of $-30°$ C. $+30°$ C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy-, isobutoxy-, s-butoxy-, and t-butoxymethylenetriphenylphosphorane. Various hydrocarbyloxymethylenetriphenylphosphoranes which are optionally substituted for the alkoxymethylenetriphenylphosphoranes and are accordingly useful for preparing the formula LII intermediates wherein $R_{26}$ is hydrocarbyl, include alkoxy-, aralkoxy-, cycloalkoxy-, and aryloxymethylenetriphenylphosphoranes. Examples of these hydrocarbyloxytriphenylphosphoranes are 2-methyl butyloxy-, isopentyloxy-, heptyloxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and p-methylphenoxy-, phenoxymethylenetriphenylphosphorane. See for reference, *Organic Reactions*, Vol. 14, pg. 346–348, John Wiley and Sons, New York, New York, (1965). The formula LII enol intermediates are then hydrolyzed to the formula LIII lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula LIV compound is then prepared from the formula LIII compound by oxidation of the formula LIII lactol to a lactone. This transformation is carried out, using for example, silver oxide as an oxidizing reagent, followed by treatment with pyridine hydrochloride.

The formula LIV lactone may then be converted to the formula LV ether by transformation of any free hydroxy moieties to blocking groups, according to $R_{10}$, following the procedures herein described for these transformations.

Thereafter the formula LVI compound is prepared from the formula LV compound by reduction of the formula LV lactone to a lactol. For example, diisobutylaluminum hydride is employed as is described above for the reduction of lactones to lactols. The formula LVI lactols so prepared are then used alternatively for the preparation of the formula LVIII or LIX compound.

In the preparation of the formula LVIII compound, the formula LVI lactol is first transformed into the formula LVII compound by reduction of the formula LVI lactol. The formula LVII compound is then transformed into the corresponding formula LVIII compound by a Williamson synthesis. Methods and corresponding reagents employed in the transformation of the formula LVI compound to the formula LVII and thereafter the transformation of the formula LVII compound to the formula LVIII compound are analogous to methods described hereinabove for the transformation of the formula XLI compound to the formula XLII compound and thereafter the transformation of the formula XLII compound to the formula XLIII compound.

Accordingly, the formula LVIII 4-oxo-PGF$_{1\alpha}$-type compound is prepared.

The formula LIX compound is prepared from the formula LVIII compound by a Wittig alkylation, using the appropriate ($\omega$-carboxyalkyl)triphenylphosphonium bromide, $HOOC-CH_2-(CH_2)_hC-H_2-P-(C_6H_5)_3$, wherein $h$ is as defined above. The reation proceeds as is generally known in the art, by first mixing the appropriate ($\omega$-carboxyalkyl)triphenylphosphonium bromide with sodio dimethyl sulfinylcarbanide, at ambient temperature, and adding the formula LVI lactol to this mixture. Thereafter the carboxy hydrogen of the compound so formed is transformed to an $R_1$ moiety by the methods and procedures hereinbelow described. Accordingly, there is prepared the formula LIX cis-4,5-didehydro-PGF$_1$-type compound.

Chart E provides a method whereby the formula LXI compound is transformed to the corresponding formula LXII PGF$_{2\alpha}$- or 11-deoxy-PGF$_{2\alpha}$-type compound or formula LXIII PGF$_{1\alpha}$- or 11-deoxy-PGF$_{1\alpha}$-type compound.

The formula LXII compound is prepared from the formula LXI compound using the appropriate ($\omega$-carboxyalkyl)triphenylphosphonium bromide, $HOOC-(CH_2)_g-CH_2-P-(C_6H_5)_3Br$, as is described above followed by transformation of the carboxy hydrogen to an $R_1$ moiety as described below. The formula LXIII compound is then prepared from the formula LXII compound by catalytic hydrogenation of the cis-5,6-double bond. Hydrogenation methods known in the art are employed, e.g., the use of metal catalysts under a hydrogen atmosphere. The reaction here is terminated when one equivalent of hydrogen is absorbed per equivalent of prostaglandin-type compound. Mixtures of compounds thereby produced are conveniently separated by silica gel chromatography.

Chart F provides a method whereby the prostaglandin-type intermediates of Charts B, C, D, and E are transformed to the corresponding PGF, 11-deoxy-PGF, PGE, 11-deoxy-PGE, PGA, or PGB analogs.

The formula LXXI compound is as prepared above. The formula LXXII PGE-type compound is prepared from the formula LXXI compound by oxidation methods known in the art. For example, the Jones reagent is advantageously employed herein. The formula LXXIII compound is then prepared from the formula LXXI compound or the formula LXXII compound by hydrolysis of any blocking groups. Such hydrolysis proceeds by mixing the reactant with, for example, water, tetrahydrofuran, and acetic acid as described above.

The formula LXXIV compound is then prepared from the formula LXXIII compound by transformation of the $R_1$ moiety of the formula LXXXIII compound to its methyl ester. Methods hereinbelow described are employed. The C-15 epimers are then separated, thereby preparing the formula LXXV compound.

The formula LXXVI compound, which is represented by formula LXXIII when the $M_5$ moiety consists of separated C-15 epimers, is prepared optionally from the formula LXXV compound by transformation of the carboxy methyl ester of formula LXXV compound to a $R_1$ moiety as described above.

The formula LXXVII compound is prepared from the formula LXXVI compound wherein $M_{18}$ is =O by a ring carbonyl reduction. Methods hereinbelow described are employed. The formula LXXVIII and formula LXXIX compounds are prepared from the formula LXXVII wherein $M_{18}$ is O employing an acidic or basic dehydration respectively. Methods described below for these acidic or basic dehydrations are employed.

The formula LXXVIII compound is optionally prepared from the formula LXXVI compound wherein $R_8$ is hydroxy by acetylation with acetic anhydride, thereby preparing a highly unstable corresponding PGE-type 11,15-diacetate, followed by silica gel chromatography. The PGE-type 11,15-diacetate thereby spontaneously decomposes to the corresponding PGA-type 15-acetate, which is hydrolysed to yield the formula LXXVIII PGA-type product. Optionally, however, the 11,15-diacetate may be allowed to stand at room temperature whereby spontaneous decomposition will ordinarily be effected within one to five days.

The above acidic dehydrations are carried out by methods known in the art for acidic dehydrations of known prostanoic acid derivatives. See for reference Pike, et al., *Proceedings of the Nobel Symposium* II, Stockholm (1966), Interscience Publishers, New York, pg. 162–163 (1967); and British Specification No. 1,097,533. Alkanoic acids of 2 to 6 carbon atoms, inclusive, preferentially acetic acid, are employed in this acidic dehydration. Dilute aqueous solutions of mineral acids e.g. hydrochloric acid, especially in the presence of a solubilizing diluent, e.g. tetrahydrofuran, are also useful as reagents for this acidic dehydration. Use, however, of mineral acids as described above may cause partial hydrolysis of the carboxyl ester of the formula CXI PGE reactant.

The above basic hydrations or double bond migrations (i.e., conversion of the PGA-type compound to the PGB-type compound are carried out by methods known in the art for dehydration or double bond migration of known prostanoic acid derivatives. See for reference Bergstrom, et al., *Journal of Biological Chemistry* 238, 3555 (1963). Bases employed are any of those whose aqueous solution has pH greater than 10. Preferred bases are the alkali metal hydroxides. A mixture of water and sufficient quantity of a water miscible alkanol to yield a homogeneous reaction mixture is suitable as a reaction medium. The reactant is then maintained in such reaction medium until the starting material is completely reacted, as shown by the characteristic ultraviolet absorption of the PGB-type compound at 278 mμ.

In the employment of the processes above when C-15 tertiary alcohols are to be prepared ($R_5$ is methyl) the use of blocking groups is not required. Accordingly, in the steps of the above charts the introduction and hydrolysis of blocking groups are thereby omitted by the preferred process.

Certain (3RS)-3-methyl lactones of chart A may be separated into their respective (3S) or (3R)-epimers by silica gel chromatographic separation techniques. Where such separation is possible, this route is preferred. Accordingly, in these cases the separation is effected and $M_5$ is

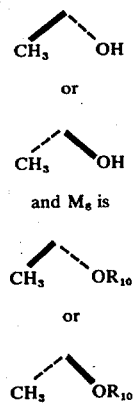

wherein $R_{10}$ is a blocking group. Accordingly, the separation procedure described in Chart F (formula LXIII – LXXV) is omitted when the optical lactone separation is employed.

When a cis-4,5-didehydro-cis-13-$PGF_{1\alpha}$ or cis-4,5-didehydro-11-deoxy-cis-13-$PGF_{1\alpha}$ -type compound is to be prepared by the procedure of Chart D, the Wittig alkylation step LVI to LIX may be performed on the formula LIII lactol, instead of the formula LVI lactol, thereby eliminating the oxidation, etherification, and reduction steps of Chart D (LIII through LVI).

Chart G provides an alternate whereby the 15-metyl-PG-type compounds are prepared from formula CI starting material.

The formula CI compound is prepared above. The formula CII compound is prepared by a ring carbonyl reduction of the formula CI compound, employing methods known in the art.

Prostaglandin cyclopentane ring carbonyl reductions are carried out using those methods known in the art for ring carbonyl reductions of known prostanoic acid derivatives. See, for example, Bergstrom, et al., Arkiv. Kemi. 19,563 (1963), Acta. Chem. Scand. 16, 969 (1962), and British Specification No. 1,097,533. Any reducing agent is used which does not react with carbon-carbon double bonds or ester groups. Preferred reagents are lithium (tri-tert-butoxy) aluminum hydride; the metal borohydrides especially sodium, potassium, and zinc borohydrides; the metal trialkoxy borohydrides, e.g. sodium trimethoxy borohydride.

When desired, the mixtures of alpha and beta hydroxy isomers at the C-9 position are separated into individual alpha or beta isomers by methods known in the art for separation of analogous pairs of known isomeric prostanoic acid derivatives. See, for example, Bergstrom, et al., cited in the preceding paragraph, Granstrom, et al., *Journal of Biological Chemistry* 240, 457 (1965), and Green et al., *Journal of Lipid Research* 5, 117 (1964). Especially preferred separation methods are partition chromatographic procedures (both normal and reversed phase), preparative thin layer chromatography, and counter current distribution procedures.

The formula CIII compound is prepared from the formula CII compound by oxidation of the C-15 hydroxy to a C-15 oxo group. Reagents known in the art which selectively effect this oxidation are employed. Accordingly, 2,3-dichloro-5,6-dicyano-1,4-benzoquinone, activated manganese dioxide, or nickel peroxide (see Fieser, et al., "Reagents or Organic Synthesis" John Wiley and Sons, New York, N. Y., pgs. 215, 637, and 731) are advantageously employed.

The formula CIV compound is then prepared from the formula CIII compound by transforming free hydroxy hydrogens into silyl derivatives. Procedures known in the art employed. See for reference Pierce, "Silylation of Organic Compounds", Pierce Chemical Co., Rockford, Ill. (1968). In employing this silylation, all carboxy and hydroxy hydrogen atoms are transformed to $-Si(G)_3$ moieties. Accordingly, sufficient silylating agents must be used so that the reaction proceeds to completion. In the case that a carboxy hydrogen is present (wherein $R_1$ is hydrogen), the use of a large stoichoimetric excess of silylating agents and prolonged treatment with the silylating agent is desirable. The necessary silylating reagents for these transformations are known in the art or are prepared by methods known in the art. See, for reference Post, "Silicones and Other Silicon Compounds," Reinhold Publishing Corp., New York, N. Y. (1949).

The formula CV compound is prepared from the formula CIV compound by first reacting the formula CIV compound with the Grignard reagent of the formula $CH_3MGHal$, wherein Hal is chloro, bromo, or iodo, and then hydrolyzing the Grignard complex, for example using saturated aqueous ammonium chloride.

The formula CVI compound is then prepared from the formula CV compound by hydrolyzing with water or with dilute aqueous acetic acid the silyl groups of the formula CV compound. A dilute of water or dilute aqueous acetic acid and a sufficient quantity of a water miscible solvent e.g., ethanol, so as to yield a homogeneous reaction mixture is advantageously employed. The hydrolysis is usually complete within 2 to 12 hours at 25° C. Preferably the reaction is carried out in an inert atmosphere, e.g. nitrogen or argon.

The formula CVII compound is prepared from the formula CVI compound by transforming the $R_1$ moiety to a methyl group. This transformation is effected by the methods and procedures hereinbelow described.

The formula CVIII compound is then prepared from the formula CVII compound by separation of the C-15 epimers. Methods known in the art for the separation of C-15 mixtures of prostanoic acid isomers, for example by chromatography on neutral silica gel, or high pressure liquid chromatographic methods are used.

The formula CIX compound is then prepared from the formula CVIII compound by transformation of the carboxy methyl ester to an $R_1$ moiety. Methods and procedures known in the art and hereinbelow described are employed.

Chart H provides a method whereby the formula CXXI PGF$_\alpha$ or 11-deoxy-PGF$_\alpha$ -type starting material, as prepared herein, is transformed into the corresponding PGE$_2$-type compound by selective silylation of all hydroxy hydrogens of the formula CXXI compound, other than the C-9 hydroxy.

The formula CXXII compound is prepared from the formula CXXI compound by selective silylation of the various hydroxy groups of the formula CXXI compound over the C-9 hydroxy. Silyl groups with the scope —Si(G)$_3$, wherein G is alkyl of 1 to 4 carbon atoms, inclusive, aralkyl of 7 to 12 carbon atoms, inclusive, phenyl, phenyl substituted with one or 2 chloro, fluoro, or alkyl of one to 4 carbon atoms, inclusive, with the proviso that the various G's of the —Si(G)$_3$ moiety are the same or different, are employed. These reagents are known in the art and their use is known in the art.

For the selective silylation procedure of Chart H procedures known in the art for selective silylation of known prostanoic acid derivatives are employed. See for reference U.S. Pat. No. 3,822,303 (issued July 2, 1974), German Offenlegungsschrift 2,259,195 (Derwent Farmdoc CPI 36457U-B), and Netherlands Pat. No. 7,214,142 (Derwent Farmdoc CPI 26221U-B).

Examples of the —Si(G)$_3$ moiety are trimethylsilyl, dimethyl(tert-butyl)silyl, dimethyl phenyl silyl, and methylphenylsilyl. Examples of alkyl of 1 to 4 carbon atoms, inclusive, aralkyl of 7 to 12 carbon atoms, inclusive, and phenyl or substituted phenyl moieties are provided hereinabove.

The formula CXXIII compound is prepared from the formula CXXII compound by oxidation of the C-9 hydroxy to a C-9 oxo. Oxidation reagents and methods known in the art are employed. For example, the Jones reagent is advantageously employed as discussed above.

The formula CXXIV compound is prepared from the formula CXXIII compound by hydrolysis of the silyl groups. Hydrolysis proceeds by methods known in the art, e.g. the use of water or dilute aqueous acetic acid in a diluent of water and a quantity of a water miscible solvent sufficient to yield a homogeneous reaction mixture. This hydrolysis is ordinarily complete within 2 to 12 hr. at 25° C., and is preferably carried in an atmosphere of an inert gas such as nitrogen or argon.

Chart I provides a method whereby PGA-type compounds are transformed into corresponding 11-deoxy PGE-type compounds, according to formula CXXXII or CXXXVI.

The formula CXXXII compound is prepared from the formula CXXXI compound by selective catalytic hydrogenation of the cyclopentene ring olefinic unsaturation. This transformation is selectively effected without affecting side-chain unsaturation. For this purpose a 5 to 10 percent palladium or rhodium catalyst on carbon, alumina or other suitable support is employed. The reaction is carried out in any suitable organic solvent, e.g. ethyl acetate, methanol, ethanol, or diethyl ether at temperatures of −30° to +50° C. and pressures greater than or equal to the atmospheric pressure, but less than several atmospheres.

The formula CXXXIII compound is prepared from the formula CXXXI compound by replacing any free hydroxy hydrogen with a blocking group, according to $R_{31}$.

This blocking group function prevents attack on the hydroxy by subsequent reagents, especially the reagent employed herein for the transformation of the C-9 hydroxy to a C-9 oxo group. This blocking group further functions so as to be replaced by hydrogen at a later stage in the preparation of the prostaglandin-type products. Blocking groups, according to $R_{31}$, which are useful for these purposes include alkanoyl of 2 to 12 carbon atoms, inclusive, tetrahydropyranyl, tetrahydrofuranyl, a group of the formula $$-C(R_{11})(OR_{12})-CH(R_{13})(R_{14}),$$

wherein $R_{11}$, $R_{12}$, $R_{13}$, and $R_{14}$ are as defined above, and a silyl group of the formula —Si(G)$_3$, wherein G is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive.

The transformations of Chart I which involve replacing any hydroxy hydrogen with a blocking group according to $R_{31}$ employ methods known in the art. Further subsequent hydrolysis of these blocking groups according to $R_{31}$ proceeds by methods known in the art.

When the blocking group is of the formula $$-C(R_{11})(OR_{12})-CH(R_{13})(R_{14}),$$

wherein $R_{11}$, $R_{12}$, $R_{13}$, and $R_{14}$ are as defined above, the appropriate reagent is a vinyl ether, e.g. isobutyl vinyl ether or any vinyl ether of the formula $$C(R_{11})(OR_{12})=C(R_{13})(R_{14}),$$

wherein $R_{11}$, $R_{12}$, $R_{13}$, and $R_{14}$ are as defined above; or an unsaturated cyclic or heterocyclic compound, e.g. 1-cyclohexen-1-yl methyl ether or 5,6-dihydro-4-methoxy-2H-pyran. See C. B. Reese, et al., *Journal of the American Chemical Society* 89, 3366 (1967). The reaction conditions for such vinyl ethers and unsaturates are similar to those for dihydropyran above.

The subsequent hydrolysis of these blocking groups according to $R_{31}$ proceeds by methods known in the art. Silyl groups are readily removed by prior art procedures known to be useful for transforming silyl ethers and silyl esters to alcohols and carboxylic acids, respectively. For reference see Pierce, cited above, especially page 447 thereof. A mixture of water and a sufficient quantity of a water miscible organic diluent to yield the homogeneous reaction mixture represents a suitable reaction medium. Addition of a catalytic amount of an organic or inorganic acid hastens the hydrolysis. The length of time require for hydrolysis is determined in part by temperature. With a mixture of water and methanol at 25° C. several hr. is usually sufficient for hydrolysis. At 0° C., several days are required.

For the hydrolysis of the various other blocking groups according to $R_{31}$ mild acidic conditions are employed.

The formula CXXIV compound is prepared from the formula CXXXIII compound by reduction of the formula CXXXIII compound with reducing agent which selectively effects reduction of the ring unsaturation and reduction of the C-9 oxo group to a C-9 hydroxy group, without reducing side chain unsaturation. For this purpose an alkali metal borohydride, e.g. sodium, potassium, or lithium borohydride is effectively employed in aqueous solution. The reaction is carried at about −20° C. and is complete within a few minutes.

The formula CXXXV compound is prepared by oxidation of the formula CXXXIV compound using a oxidizing reagent, such as the Jones reagent (acidified chromic acid). See for reference *Journal of the Chemical Society* 39 (1946). A slight stoichoimetric excess beyond the amount necessary to oxidize a single hydroxy group is employed. Acetone is a useful diluent for this purpose. Reaction temperatures at least as low as about 0° C. should be used. Preferred reaction temperatures are in the range of −10° to −50° C. An especially useful reagent for this purpose is the Collins reagent (chromium trioxide in pyridine). See for reference J. C. Collins, et al., Tetrahedron Letters 3363, (1968). Dichloromethane is a suitable diluent for this purpose. Reaction temperatures below 30° C. are preferred. Reaction temperatures in the range of −10° to +10° C. are especially preferred. This oxidation proceeds rapidly and is complete within several minutes. The formula CXXXV compound may then be isolated by conventional methods, e.g. silica gel chromatography.

Examples of other oxidation reagents useful for this transformation are silver carbonate on celite (*Chemical Communications* 1102 (1969)), mixtures of chromium trioxide in pyridine (*Journal of the American Chemical Society* 75, 422 (1953)), and Tetrahedron Letters, 18, 1351 (1962)), tert-butyl chromate in pyridine (*Biological Chemical Journal*, 84, 195 (1962)), mixtures of sulfur trioxide in pyridine and dimethyl sulfoxide (*Journal of the American Chemical Society* 89, 5505 (1967)), and mixtures of dicyclohexylcarbodiimide and dimethylsulfoxide (*Journal of the American Chemical Society* 87, 5661 (1965)).

The formula CXXXVI compound is then prepared from the formula CXXXV compound by hydrolysis of the blocking groups, according to $R_{31}$, as described above.

Chart J provides a method whereby 15-hydroxy-13-trans PG-type compounds are transformed into 13-cis-PG-type compounds.

The formula CLI 13-trans PG-type compound is known in the art or is prepared by methods known in the art. For example, the methods of the preceding charts herein are useful in the preparation of the formula CLI compound when the photoisomerization of the 3-oxo-bicyclic lactone is omitted.

The formula CLII compound is prepared from the formula CLI compound by a selective oxidation of the C-15 hydroxy to a C-15 oxo group. Methods described hereinabove (CHART G) are employed.

The formula CLIII compound is then prepared from the formula CLII compound by photoisomerization of the 13-trans bond of the formula CLII compound to a 13-cis bond. Methods described hereinabove for the photoisomerization of 3-oxo bicyclic lactones are employed.

The formula CLIV compound is prepared from the formula CLIII compound by silylation of the free hydroxy moieties of the formula CLIV compound. Silylation reagents as described above, for example, in Chart N are employed. Procedures known in the art are used. See for reference those citations hereinabove provided.

The formula CLV compound is prepared from the formula CLIV compound by methods described herein for the transformation of an oxo moiety to the $M_5$ moiety, and thereafter the transformation of the $M_5$ moiety to an $M_1$ moiety. Accordingly, reduction methods hereinabove described are employed in the transformation of the formula CLIV 15-oxo compound to the formula CLV 15-hydroxy compound, hydroxy alkylation techniques are employed in the transformation of the 15-hydroxy compound to a 15-methoxy compound, and side chain oxo alkylation techniques are employed in the transformation of the formula CLIV compound to the formula CLV 15-methyl compound (e.g., use of a Grignard reagent or trimethylaluminum).

The formula CLVI compound is prepared from the formula CLV compound by hydrolysis of the silyl groups. Methods as described in CHART H are employed.

Optically active PG-type products are obtained from optically active intermediates, according to the process steps of the above charts. Likewise optically active PG-type compounds are obtained from corresponding optically active PG-type compounds following the procedures in the above charts. When racemic intermediates are used in the reactions above, racemic products are obtained. These products may be used in their racemic form or if preferred they may be resolved as optically active enantiomers following procedures known in the art. For example, when a PG-type free acid is obtained, the racemic form thereof is resolved into d and l forms by reacting said free acid by known procedures with an optically active base (e.g., brucine or strychnine) thereby yielding a mixture of 2 diastereomers which are separable by procedures known in the art (fractional crystallization to yield the separate diastereomeric salts). The optically active acid may then be prepared from the salt by general procedures known to the art.

In all of the above described reactions, the products are separated by conventional means from starting material and impurities. For example, by use of silica gel chromatography monitored by thin layer chromatography the products of the various steps of the above charts are separated from the corresponding starting materials and impurities.

As discussed above, the processes herein described lead variously to acids ($R_1$ is hydrogen) or to esters.

When the alkyl ester has been obtained and an acid is desired, saponification procedures, as known in the art for PGF-type compounds are employed.

For alkyl esters of PGE-type compounds enzymatic processes for transformation of esters to their acid forms may be used by methods known in the art when saponification procedures would cause dehydration of the prostaglandin analog. See for reference E. G. Daniels, *Process for Producing An Esterase*, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, *Organic Reactions*, John Wiley and Sons, Inc., New York, N.Y., Vol 8, pp. 389–394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tertbutyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichoimetric amount of silver nitrate.

Various methods are available for preparing phenyl or substituted phenyl esters within the scope of the invention from corresponding aromatic alcohols and the free acid PG-type compounds, differing as to yield and purity of product.

Thus by one method, the PG-type compound is converted to a teritary amine salt, reacted with pivaloyl halide to give the mixed acid anhydride and then reacted with the aromatic alcohol. Alternatively, instead of pivaloyl halide, an alkyl or arylsulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "*Reagents for Organic Synthesis*", pp. 231–236, John Wiley and Sons, Inc., New York, (1967). The PG-type compound is contacted with one to ten molar equivalents of the aromatic alcohol in the presence of 2–10 molar equivalents of dicyclohexylcarbodiimide in pyridine as a solvent.

One preferred novel process for the preparation of these esters, however, comprises the steps:

(a) forming a mixed anhydride with the PG-type compound and isobutylchloroformate in the presence of a tertiary amine and (b) reacting the anhydride with an appropriate aromatic alcohol.

The mixed anhydride described above is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of the PG-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the coformed amine hydrochloride usually crystallizes out, but need not be removed for the next step.

The aromatic alcohol is preferably used in equivalent amounts or in substantial stoichoimetric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible nonsolvent such as diethyl ether, hexane, or water. The crystals are then collected by conventional techniques, e.g. filtration or centrifugation, washed with a small amount of solvent, and dried under reduced pressure. They mahy also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the prepraration of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichoimetric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of a free hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, or hexanoic anhydride gives the corresponding carboxyacylate.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent.

An inert organic diluent, (eq., dioxane) can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24 hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer on deuterochloroform solutions with tetramethylsilane as an internal standard (downfield).

Mass spectra are recorded on an CEG model 110B Double Focusing High Resolution Mass Spectrometer on an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

Brine, herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas Hoover melting point apparatus.

DDQ refers to 2,3-dichloro-5,6-dicyano-1,4-benzoquinone.

THF refers to tetrahydrofuran.

Specific Rotations, [a], are determined for solutions of a compound in the specified solvent at ambient temperature with a Perkin-Elmer Model 141 Automatic Polarimeter.

EXAMPLE 1

Dimethyl 3,3-dimethyl-2-oxo-4-phenylbutylphosphonate,

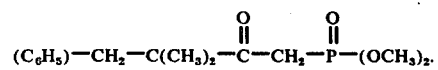

A. To a solution of 101.2 g. of diisopropylamine in 125 ml. of tetrahydrofuran under nitrogen at 0° C. is added dropwise with cooling (using an ice-methanol bath) 625 ml. of n-butyllithium in hexane. To the resulting solution is added dropwise with cooling 46.5 ml. of isobutyric acid. This mixture is then stirred at 0° C. for 90 min. and thereafter cooled to −15° C. Benzyl chloride (60 ml.) is added with stirring at such a rate as to maintain the reaction temperature below −5° C. The resulting mixture is thereafter stirred at ambient temperature for 4 hr. This stirred mixture is then diluted with diethyl ether and excess cold dilute hydrochloric acid. The organic layer is washed with saline and thereafter dried, concentrated, and the residue distilled under vacuum. Accordingly, there is prepared 2,2-dimethyl-3-phenyl propionic acid.

B. A mixture of 48 g. of the product of part A of this example and 82 g. of thionyl chloride are heated with stirring on a steam bath for 2 hr. The mixture is then concentrated uner vacuum. Thereafter dry benzene is added and the resulting mixture is concentrated again, removing all traces of thionyl chloride. Distillaton of this residue yields 48.2 g. of 2,2-dimethyl-3-phenylpropionyl chloride.

C. To a solution of 63 g. of dimethylmethylphosphonate in 600 ml. of tetrahydrofuran under nitrogen at −75° C. is added with stirring 312 ml. of 1,6molar n-butyllithium in hexane. The additon rate is adjusted so that the reaction temperature remains below 55° C. Ten minutes after the addtion is complete, 48.2 g. of the reaction product of part B of this example and 50 ml. of tetrahydrofuran are added dropwise at such rate as to maintain the reaction temperature below −60° C. The resulting mixture is then stirred at −75° C. for 2 hr. and then ambient temperature overnight. Acetic acid (20 ml.) is thereafter added and the resulting mixture distilled under vacuum, thereby removing most of the tetrahydrofuran. The residue is then shaken with diethyl ether in methylene chloride (3:1 by volume) and a cold dilute sodium bicarbonarte solution. The organic layer is then washed with brine, dried, and concentrated. The residue was crystallized from diethyl ether, yielding 54 g. of dimethyl 3,3-dimethyl-2-oxo-4-phenylbutylphosphonate (8.0 g.), the title compound. The melting point is 48°–50° C.

Following the procedure of Example 1, but using in place of benzyl chloride substituted benzyl chlorides of the formula

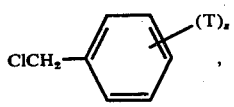

wherein T is fluoro, chloro, trifluoromethyl, alkyl of one to 3 carbon atoms, inclusive, or alkoxy of one to 3 carbon atoms, inclusive, and wherein s zero, one, 2, or 3, with the proviso that not more than two T's are other than alkyl, and with the further proviso that the various T's may be the same or different, there are prepared the corresponding dimethyl-3,3-dimethyl-2-oxo-4-(substituted phenyl)butylphosphonates. For example, there is prepared by this procedure dimethyl 3,3-dimethyl-2-oxo-4-(p-fluorophenyl)butylphosphonate.

Further, following the procedure of Example 1, but using in place of the isobutyric acid of Example 1, part A, propionic acid, there is prepared dimethyl 3-methyl-2-oxo-4-phenylbutylphosphonate. Following the procedure of Example 1, but using the substituted benzyl chlorides described above in place of benzyl chloride and propionic acid in place of isobutyric acid there are prepared the various dimethyl 3-methyl-2-oxo-4-(substituted phenyl)-butylphosphonates wherein the phenyl substitution is as described above.

Further, following the procedure of Example 1, but using acetic acid in place of isobutyric acid as used in Example 1, part A, there is prepared dimethyl-2-oxo-4-phenylbutylphosphonate. Using acetic acid in combination with the various substituted benzyl chlorides described above according to the procedure of Example 1, there are prepared the various dimethyl 2-oxo-4-(substituted phenyl)butyl phosphonates, wherein the phenyl substitution is as described above.

Following the procedure of Example 1, but using 2,2-difluoroacetic acid in place of isobutyric acid as used in part A of Example 1, there is prepared dimethyl 3,3-difluoro-2-oxo-4-phenylbutylphosphonate. Further, following the procedure of Example 1, but using 2,2-difluoro acetic acid in combination with substituted benzyl chlorides described above, there are prepared the corresponding dimethyl 3,3-difluoro-2-oxo-4-substituted phenylbutylphosphonate, wherein the phenyl substitution is as described above.

Further, following the procedure of Example 1, but using 2-fluoro acetic acid in place of isobutyric acid there is prepared dimethyl 3-fluoro-2-oxo-4-phenylbutylphosphonate.

Using 2-fluoro acetic acid and the various substituted benzyl chlorides described above according to the procedure of Example 1, there are prepared the various dimethyl 3-fluoro-2-oxo-(substituted phenyl)butyl phosphonates, wherein the phenyl substitution is as described above.

Further, following the procedure of Example 1, but using any of the alkanoic, branched alkanoic, or fluoro-substituted alkanoic acids described above in place of isobutyric acid and cis-1-butenyl chloride in place of benzyl chloride, there are prepared the corresponding dimethyl-2-oxo-cis-4-heptenylphosphonates: dimethyl 3,3-dimethyl-2oxo-cis-3-heptenylphosphonate, dimethyl 3-methyl-2-oxo-cis-4-heptenylphosphonate, dimethyl 3-fluoro-2-oxo-cis-4-heptenylphosphonate, dimethyl 3,3-difluoro-2-oxo-cis-4-heptenylphosphonate, and dimethyl 2-oxo-cis-4-heptenylphosphonate,

EXAMPLE 2

Triphenylphosphonium salt of 2,2-difluoro-5-bromopentanolic acid, $Br(C_6H_5)_3P—(CH_2)_3—CF_2—COOH$.

A. Methyl furoate is dissolved in 180 ml. of methanol. Thereafter 1 g. of 5 percent palladium-on-charcoal is added. This mixture is then hydrogenated at 1 to 3 atmospheres. After 45 hr. 0.79 moles of hydrogen are consumed. The black mixture is then filtered through Celite using 50 ml. of methanol to wash the reaction flask and filter. Evaporation of the filtrate under reduced pressure at 40°–45° C. bath temperature yields 51 g. of a yellow oil which is thereafter distilled, collecting that fraction boiling at 32°–35° C. Thereby, methyl tetrahydrofuroate (46.7 g.) is prepared.

B. Anhydrous hydrobromic acid is bubbled through 50 ml. of acetic anhydride with cooling until a specific gravity of 1.3 is obtained. This reagent is then added to 25 g. of the reaction product fo step A of this example, with exclusion of moisture while cooling and stirring. Stirring in the ice water bath is continued for 15 min.; thereafter, the mixture is allowed to stand at room temperature overnight. The reaction mixture is then poured into 600 g. of crushed ice and water with stirring and extracted with diethyl ether. The ether extract is washed with aqueous sodium hydroxide, dried over sodium sulfate, filtered, and thereafter evaporated under reduced pressure to yield 38 g. of a pale yellow oil, which is thereafter distilled under high vacuum, yielding 31.6 g. of methyl 2-acetoxy-5-bromo-pentanoate.

C. To a solution of 60 g. of the reaction product of part B of this example in 200 ml. of methanol is added 100 ml. of methanol, which is saturated with hydrobromic acid at 0° C. and 1.3 specific gravity before the addition. The reaction mixture is then allowed to stand at room temperature overnight. The solvent is thereafter evaporated under reduced pressure at 35° C. bath temperature and 400 ml. of toluene is thereafter added. The solvent is again evaporated. This residue is then dissolved in 2 l. of ethyl acetate, washed with 5 percent aqueous sodium hydroxide solution and sodium chloride solution before being dried over sodium sulfate. Filtration and evaporation of the solvent under reduced pressure at 45° C. yields 42 g. of oil which is distilled under high vacuum, yielding 28.8 g. of methyl 2-hydroxy-5-bromopentanoate.

D. To a solution of 34.4 g. of the reaction product of part C of this example and 400 ml. of acetone is added with stirring and cooling 75 ml. of Jones reagent (26.73 G. of $CrO_3$ in 23 ml. of concentrated sulfuric acid, diluted to 100 ml. with water) at such a rate that the reaction temperature is maintained between 30° and 40° C. The reaction is complete in approximately 20 min. Thereafter the reaction mixture is stirred for 1.5 hr. Thereafter 150 ml. of isopropyl alcohol are slowly added with stirring during 30 min. The reaction mixture is then diluted with 1.8 l. of water and extracted with 2.4 l. of methylene chloride. These extracts are washed with brine and dried with sodium sulfate. Filtration and evaporation of the solvent under reduced pressure yields 30.8 g. of a pale yellow oil, containing methyl 2-oxo-5-bromopentanoate. This oil is used in the following steps of this example without further purification.

E. With the exclusion of moisture under a nitrogen atmosphere 195 ml. of $MoF_6 \cdot BF_3$ is cooled in a dry-ice acetone bath. A solution of 30.8 g. of the reaction product of step D of this example and 40 ml. of methylene chloride is added dropwise with stirring over a period of 15 min. The reaction temperature is maintained between −35° and −45° C. Stirring the dry ice acetone bath is continued for one hr., the cooling bath thereafter is removed, and the reaction mixture thereafter diluted with 200 ml. of methylene chloride and 400 ml. of water. The organic and aqueous layers are separated, the aqueous layer being extracted with methylene chloride and the combined methylene chloride extracts washed with 250 ml. of water, 250 ml. of 5 percent aqueous potassium bicarbonate, 250 ml. of brine, and thereafter dried over sodium sulfate. Filtration and evaporation of the solvent yields 31.1 g. of a dark brown oil, which when distilled under high vacuum yields methyl 2,2-difluoro-5-bromopentanoate (14 g.).

F. The reaction product of part E of this example (28 g.) is stirred in 175 ml. of aqueous hydrobromic acid (specific gravity 1.71) for 3 hr. at room temperature. The reaction mixture is then cooled in an ice bath, and diluted with 1300 ml. of diethyl ether. The organic and aqueous layers are separated and the aqueous layer is extracted with diethyl ether. The combined ethereal solutions are washed with water and the ethereal loss solutions are backwashed with 400 ml. of ether and the combined ethereal solutions is then dried over sodium sulfate. Filtration and evaporation of the solvent yields 27.7 g. of a pale yellow oil, 2,2-difluoro-5-bromopentanoic acid, which is used in the following step of this example without further purification.

G. A mixture of 15.2 g. of the reaction product of part F of this example, 80 ml. of acetonitrile and 22 g. of triphenylphosphine are heated to reflux with stirring for 30 hr. The reaction mixture is then heated to 110° C., diluted with 160 ml. of toluene, and the mixture is allowed to cool slowly at room temperature for 12 hr. with stirring. The reaction mixture is then stored at 5° C. for 24 hr. A precipitate is collected, washed with 50 ml. of toluene, and dried under vacuum at room temperature. 20.9 g. of the title compound of this example is thereby obtained.

EXAMPLE 3

(6-Carboxyhexyltriphenylphosphonium bromide).

A mixture of 63.6 g. of 7-bromoheptanoic acid, 80 g. of triphenylphosphine, and 30 ml. of acetonitrile, is refluxed for 68 hr. Thereafter 200 ml. of acetonitrile is removed by distillation. After the remaining solution is cooled to room temperature, 30 ml. of benzene is added with stirring. The mixture is then allowed to stand for 12 hr. A solid separates which is collected by filtration, yielding 134.1 g. of product, melting point 185°–187° C.

Following the procedure of Example 3, but using 3-bromopropionic acid, 4-bromobutanoic acid, 5-bromopentanoic acid, or 6-bromohexanoic acid, in place of 7-brmoheptanoic acid, there are prepared the corresponding ($\omega$-carboxyalkyl)triphenylphosphonium bromides.

EXAMPLE 4

3$\alpha$-Benzoyloxy-5$\alpha$-hydroxy-2$\beta$-(3-oxo-4,4-difluoro-1-cis-octenyl)-1$\alpha$-cyclopentaneacetic acid, $\gamma$ lactone (Formula XXIII: $R_7$ is n-butyl, $R_{16}$ is benzoyloxy, $R_3$ and $R_4$ of the $L_1$ moiety are fluoro, and Y is cis-CH=CH-).

Refer to Chart A.

A. A solution of 24.3 g. of thallous ethoxide in 125 ml. of dry benzene is cooled in an ice bath, and thereafter a solution of 25.3 g. of methyl 3,3-difluoro-2-oxoheptylphosphonate in 75 ml. of benzene is added and thereafter rinsed with 50 ml. of benzene. The solution is stirred for 30 min. at 5° C. and therefter 22.1 g. of crystalline 3$\alpha$-benzoyloxy-5$\alpha$-hydroxy-2$\beta$-carboxaldehyde-1$\alpha$-cyclopentaneacetic acid, Γ lactone is added rapidly. The reaction mixture is then stirred for 13 hr. at ambient temperature yielding a brown solution of pH 9–10. Acetic acid (6 ml.) is added and the mixture is transferred to a beaker with 600 ml. of diethyl ether. Celite and 500 ml. of water is added, followed by the addition of 30 ml. (about 33 g.) of saturated potassium iodide. The mixture (containing a bright yellow preicipitate of thallous iodide) is stirred for about 45 min., and thereafter filtered through a bed of Celite. The organic layer is then washed with water, aqueous potassium bicarbonate, and brine. Thereafter the resulting mixture is dried over magnesium sulfate and evaporated at reduced pressure, yielding 33.6 g. of an oil, which is then chromatographed on 600 g. of silica gel packed in 20 percent ethyl acetate in cyclohexane. Elution, collecting 500 ml. fractions, with 2 l. of 20 percent, 2 l. of 25 percent, and 4 l. of 30 percent ethyl acetate in cyclohexane yields 20.3 g. of crude product, which upon recrystallization from 240 ml. of diethyl ether in pentane (2:1) yields 13.3 g. of 3$\alpha$-benzoyloxy-5$\alpha$-hydroxy-2$\beta$-(3-oxo-4,4-difluoro-trans-1-octenyl)-1$\alpha$-cyclopentaneacitic acid, $\gamma$ lactone.

Alternatively this product is prepared by adding 3α-benzoyloxy-2β-carboxaldehyde-5α-hydroxy-1α-cyclopentaneacetic acid γ lactone (3 g.) in 30 ml. of dichloromethane to a solution of dimethyl 2-oxo-3,3-difluoroheptylphosphonate (6.69 g.) and sodium hydride (1.35 g.) in 15 ml. of tetrahydrofuran. The resulting reaction mixture is then stirred for 2 hr. at about 25° C., acidified with acetic acid, and concentrated under reduced pressure. The residue is partitioned between dichloromethane and water, and the organic phase is concentrated. The residue is chromatographed on silica gel, eluting with ethyl acetate in Skellysolve B (1:1).

B. A solution of 16.3 g. of the reaction product of step A of this example in one l. of acetone (agitated by bubbling nitrogen through the solution) is irradiated for 3 hr. in a Rayonot Photochemical Reactor (RPR-208, using 8 lamps) wherein the photo emission spectrum shows substantial intensity at a wave length at or around 3500 Angstroms. The solvent is then evaporated and the residue chromatographed on 1.5 kg. of silica gel packed in 10 percent ethyl acetate in cyclohexane. Elution, collecting 1.5 l. fractions, with 4.5 l. each of 10 percent, 15 percent, 20 percent, 25 percent, 30 percent, 35 percent, and 40 percent ethyl acetate in cyclohexane yields 12.5 g. of starting material and 4.2 g. of crude 3α-benzoyloxy-5α-2β-(3-oxo-4,4-difluoro-cis-1-octentyl)-1α-cyclopentaneacetic acid γ lactone. Further chromatographic purification yields 3.85 g. of the pure cis isomer as a slightly yellow oil. Rf equals 0.17 (33 percent ethyl acetate in cyclohexane). The ultraviolet absorption spectrum show $\lambda_{max}$ at 231 nm. with ε of 2100. The infrared spectrum shows absorptions in cm.$^{-1}$ at 1775, 1720, 1620, 1600, 1585, 1495, 1450, 1315, 1275, 1225, 1175, 1115, 1075, 1045, 1025, 1000, and 715. The NMR spectrum for a deuteriochloroform solution shows absorption at 7.79, 74.5, 6.63, 6.29, 5.32, 5.07, and 3.97 δ.

Following the procedure of Example 4, but using in place of 3α-benzoyloxy-5α-hydroxy-2β-carboxaldehyde-1α-cyclopentaneacetic acid γ lactone, 5α-hydroxy-2β-carboxaldehyde-1α-cyclopentaneacetic acid γ lactone, there is obtained 5α--hydroxy-2β-(3-oxo-4,4-difluoro-cis-1-octenyl)-1α-cyclopentaneacetic acid γ lactone.

Further, following the procedure of Example 4, but using in place of dimethyl 2-oxo-3,3-difluoroheptylphosphonate, any of the various dimethyl phosphonates described hereinabove there are prepared the corresponding 3α-benzoyloxy-5α-hydroxy-1α-cyclopentaneacetic acid γ lactones with a 2β-(3-oxo-cis-1-alkenyl)-substituent, optionally substituted, as follows:

4,4-difluoro-hexenyl; 4,4-difluoroheptenyl; 4,4-difluorononenyl; 4,4-difluorodecenyl; 4-fluorohexenyl; 4-fluoroheptenyl, 4-fluorooctenyl; 4-fluorononenyl; 4-fluorodecenyl; 4,4-dimethylhexenyl; 4,4-dimethylheptenyl, 4,4-dimethyloctenyl; 4,4-dimethylnonenyl; 4,4-dimethyldecenyl; 4-methylhexenyl; 4-methylheptenyl, 4-methyloctenyl, 4-methylnonenyl; 4-methyldecenyl; hexenyl; heptenyl; octenyl; nonenyl; decenyl; 5-phenylpentenyl; 5-(m-trifluoromethylphenyl)-pentenyl; 5-(m-fluorophenyl)-pentenyl; 5-(m-chlorophenyl)-pentenyl; 5-(p-trifluoromethylphenyl)-pentenyl; 5-(p-fluorophenyl)pentenyl; 5-(p-chlorophenyl)-pentenyl; 4-methyl-5-phenylpentenyl; 4-methyl-5-(m-trifluoromethylphenyl)pentenyl; 4-methyl-5-(m-fluorophenyl)-pentenyl; 4-methyl-5-(p-trifluoromethylphenyl)-pentenyl; 4-methyl-5-(p-fluorophenyl)-pentenyl; 4-methyl-5-(p-chlorophenyl)-pentenyl; 4,4-dimethyl-5-(m-trifluoromethylphenyl)-pentenyl; 4,4-dimethyl-5-(m-fluorophenyl)-pentenyl; 4,4-difluoro-5-(m-chlorophenyl)pentenyl; 4,4-dimethyl-5-(p-trifluoromethylphenyl)pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)pentenyl; 4-fluoro-5-(m-fluorophenyl)-pentenyl; 4-fluoro-5-(m-chlorophenyl)-pentenyl; 4-fluoro-5-(p-trifluoromethylphenyl)-pentenyl; 4-fluoro-5-(p-fluorophenyl)-pentenyl; 4-fluoro-5-(p-chlorophenyl)-pentenyl; 4,4-difluoro-5-phenylpentenyl; 4,4-difluoro-5-(m-trifluoromethylphenyl)-pentenyl; 4,4-difluoro-5-(m-fluorophenyl)-pentenyl; 4,4-difluoro-5-(m-chlorophenyl)-pentenyl; 4,4-difluoro-5-(p-trifluoromethylphenyl)-pentenyl; 4,4-difluoro-5-(p-fluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4-(p-fluorophenoxy)-butenyl; 4-(p-chlorophenoxy)-butenyl; 4-methyl-4-phenoxybutenyl; 4-methyl-4-(m-trifluoromethylphenoxy)-butenyl; 4-methyl-4-(m-fluorophenoxy)-butenyl; 4-methyl-4-(m-chlorophenoxy)-butenyl; 4-methyl-4-(p-trifluoromethylphenoxy)butenyl; 4-methyl-4-(p-fluorophenoxy)-butenyl; 4-methyl-4-(p-chlorophenoxy-butenyl; 4,4-dimethyl-4-phenoxybutenyl; 4,4-dimethyl-4-(trifluoromethylphenoxy)-butenyl; 4,4-dimethyl-4-(m-fluorophenoxy)-butenyl; 4,4-dimethyl-4-(m-chlorophenoxy)-butenyl; 4,4-dimethyl-4-(p-trifluoromethylphenoxy)-butenyl; 4,4-dimethyl-4-(p-fluorophenoxy)butenyl; 4,4-dimethyl-4-(p-chlorophenoxy)-butenyl; and the like.

Following the procedure of Example 4, but using dimethyl 2-oxo-3,3-difluoro-cis-4-heptenylphosphonate in place of dimethyl 2-oxo-3,3-difluoroheptylphosphonate there is prepared 3α-benzoyloxy-5α-hydroxy-2β-(3-oxo-4,4-difluoro-cis-1,5-octadienyl)-1α-cyclopentaneacetic acid γ lactone. This is cis-1,5-octadienyl compound is separated from the mixture of cis-1,5, cis-1 -trans-5-, trans-1-cis-5-, and trans-1,5-geometric isomers produced by the photoisomerization described in Example 4, part B, by the chromatographic separation method described therein. The various other 3α-benzoyloxy-5α-hydroxy-1α-cyclopentaneacetic acid γ lactones with 2β-(3-oxo-cis-1,5-transoctadienyl)substituents are likewise prepared, e.g. 4-fluoro-4-methyl-4,4-dimethyl- and the unsubstituted 2β-(3-oxo-cis-1,5-octenyl)- compound.

For example, 3α-benzoyloxy-5α-hydroxy-2β-[3-oxo-4-(p-fluorophenoxy)-cis-1-butenyl]-1α-cyclopentaneacetic acid γ lactone exhibits NMR absorptions at (CDCl$_3$ solutions) 3.75-4.25, 4.53, 4.8-5.5, 6.11, 6.57, 6.6-7.2, and 8.15 δ PGF , PGE, PGF , PGA, and PGB analogs described herein are prepared from the formula XXIII compound wherein the C-3 position of the cyclopentane ring is substituted by a benzoyloxy moiety at C-3, as described above (Example 4).

Likewise, intermediates useful in preparing 11-deoxy-PGF , 11-deoxy-PGE, and 11-deoxy-PGF -type compounds of this invention are prepared as described above in and following Example 4 except the starting material employed is a 3-unsubstituted; that is 5α-hydroxy-2β-carboxaldehyde-1α-cyclopentaneacetic acid γ lactone. Accordingly there are prepared 5α-hydroxy-1α-cyclopentaneacetic acid γ lactones with the various 2β-side chains described following Example 4 which are useful in the same manner as the 3α-benzoyloxy compounds in the procedures of succeeding examples for preparing the 11-deoxy-PGF , PGE-, or PGF -type compounds corresponding to the PGF -, PGE-, and PGF -type compounds therein prepared.

EXAMPLE 5

3α-Benzoyloxy-5α-hydroxy-2β-[(3S)-3-hydroxy-cis-1-octenyl]-1α-cyclopentaneacetic acid γ lactone (Formula XXIV: $R_3$ and $R_4$ of the $L_1$ moiety are hydrogen, $R_5$ and $R_6$ of the $M_5$ moiety are hydrogen, $R_7$ is n-pentyl, $R_{16}$ is benzoyloxy, and Y is cis—CH=CH—) or its (3R)-hydroxy epimer.

Sodium borohydride (2.86 g.) is slowly added to a stirred suspension of 12.6 g. of anhydrous zinc chloride in 78 ml. of dimethyl ether in ethylene glycol (glyme) with ice bath cooling. The mixture is stirred for 20 hr. at ambient temperature and thereafter cooled to −20° C. A solution of 8.0 g. of 3α-benzoyloxy-5α-hydroxy-2β-(3-oxo-cis-1-ocetnyl)-1α-cyclopentaneacetic acid γ lactone (prepared according to Example 4) in 80 ml. of glyme is added over a period of 15 min. Stirring is continued for 24 hour at −20° C. and thereafter 60 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield an oil, which when chromatographed on 900 g. of silica gel packed in one percent acetone and methylene chloride, eluting with one to 15 percent acetone in methylene chloride yields the epimerically pure title product (2.17 g. of the 3S epimer and 5.1 g. of the 3R epimer).

The 3S epimer exhibits ultraviolet absorptions at $\lambda_{max}$. equals 230 nm. (ε 1300, 580). Infrared absorptions (cm$^{-1}$) are observed at 3530, 3460, 1755, 1715, 1705, 1600, 1585, 1495, 1315, 1280, 1235, 1170, 1125, 1075, 1035, 975, 910, and 710. NMR absorptions in $CDCl_3$ are observed at 4.2, 4.7, 4.86–5.82, 7.18–7.63, and 7.8–8.15 δ.

The 3R epimer exhibits ultraviolet absorption at $\lambda_{max}$. of 230 nm. (ε 12,560). NMR absorptions in $CDCl_3$ are observed 4.2–4.7, 4.86–5.82, 7.18–7.63, and 7.8 8.15.

Following the procedure of Example 5, but preparing 3α-benzoyloxy-5α-hydroxy-2β-[(3R)-3-hydroxy-4-(p-fluorophenoxy)-cis-1-butenyl]-1α-cyclopentaneacetic acid γ lactone and its 3S epimer from the corresponding 3-oxo-starting material, there are observed the following physical constants: for the 3S epimer $R_f$ equals 0.52 (ethyl acetate and Skellysolve B 3:1) and for the 3R epimer $R_f$ is 0.29 (ethyl acetate and Skellysolve B, 3:1). For each epimer, NMR absorptions are observed at ($CDCl_3$) 3.8–4.0, 4.5–6.0, 6.65–7.15, 7.2–7.6, and 7.85–8.1 δ.

Following the procedure of Example 5, but using in place of the 3α-benzoyloxy-5α-hydroxy-2β-(3-oxo-cis-1-octenyl)-1α-cyclopentaneacetic acid γ lactone starting material employed therein, the various 3α-benzoyloxy-5α-hydroxy-2β-(3-oxo-cis-1-alkenyl, alkadienyl, or substituted alkenyl or alkadienyl)-1α-cyclopentaneacetic acid γ lactones there are prepared the corresponding 3R or 3S hydroxy products.

Following the procedure of Example 5, but using in place of the 3α-benzoyloxy-5α-hydroxy-2β-(3-oxo-cis-1-octenyl)-1α-cyclopentaneacetic acid γ lactone used therein, 5α-hydroxy-2β-(3-oxo-cis-1-alkenyl, alkadienyl, or substituted alkenyl or alkadienyl)-1α-cyclopentaneacetic acid γ lactones described following Example 4, there are prepared the corresponding 3R or 3S-hydroxy products. For example, there are obtained the above 3α-benzoyloxy-5α-hydroxy- or 5α-hydroxy-1α-cyclopentaneacetic acid γ lactones wherein the 2β-side chain in either the 3R or 3S form consists of 3-hydroxy-cis-1-hexenyl; 3-hydroxy-cis-1-heptenyl; 3-hydroxy-cis-1-nonenyl; 3-hydroxy-cis-1-decenyl; 3-hydroxy-cis-1,5-octadienyl; 3-hydroxy-4-methyl-cis-1-octenyl; 3-hydroxy-4,4-dimethyl-cis-1-octenyl; 3-hydroxy-4-fluoro-cis-1-octenyl; 3-hydroxy-4,4-difluoro-cis-1-octenyl; 3-hydroxy-5-phenyl-cis-1-pentenyl; 3-hydroxy-5-(p-fluorophenyl)-cis-1-pentenyl; 3-hydroxy-5-(m-chlorophenyl)-cis-1-pentenyl; 3-hydroxy-5-(m-trifluoromethylphenyl)-cis-1-pentenyl; 3-hydroxy-4,4-dimethyl-5-phenyl-cis-1-pentenyl; 3-hydroxy-4,4-dimethyl-5-(p-fluorophenyl)-cis-1-pentenyl; 3-hydroxy-4,4-dimethyl-5-(m-chlorophenyl)-cis-1-pentenyl; 3-hydroxy-4,4-dimethyl-5-(m-trifluoromethylphenyl)-cis-1-pentenyl; 3-hydroxy-4,4-difluoro-5-phenyl-cis-1-pentenyl; 3-hydroxy-4,4-difluoro-5-(p-fluorophenyl)-cis-1-pentenyl; 3-hydroxy-4,4-difluoro-5-(m-chlorophenyl)-cis-1-pentenyl; 3-hydroxy-4,4-difluoro-5-(m-trifluoromethylphenyl)-cis-1-pentenyl; 3-hydroxy-4-phenoxy-cis-1-butenyl; 3-hydroxy-4-(p-fluorophenoxy)-cis-11 -butenyl; 3-hydroxy-4-(m-chlorophenoxy)-cis-1-butenyl; 3-hydroxy-4-(m-trifluoromethylphenoxy)-cis-1-butenyl; 3-hydroxy-4,4-dimethyl-4-phenoxy-cis-1-butenyl; 3-hydroxy-4,4-dimethyl-4-(p-fluorophenoxy)-cis-1-butenyl; 3-hydroxy-4,4-dimethyl-4-(m-chlorophenoxy)-cis-1-butenyl; 3-hydroxy-4,4-dimethyl-4-(m-trifluoromethylphenoxy)-cis-1-butenyl; and the like.

EXAMPLE 6

3α-Benzoyloxy-5α-hydroxy-2β-[(3R)-3-methoxy-cis-1-octenyl]-1α-cyclopentaneacetic acid γ lactone (Formula XXIV: $R_3$ and $R_4$ of the $L_1$ moiety are hydrogen, $M_5$ is

$R_7$ is n-pentyl, $R_{16}$ is benzoyloxy, and Y is cis—CH3=λ CH—) or its 3(S) epimer.

Refer to Chart A. A mixture of the (3R) or (3S) reaction product of Example 5 (3.6 g.), silver oxide (4.0 g.) in 50 ml. of methyl iodide and 150 ml. of benzene is stirred and heated at reflux for 18 hr. The resulting mixture is then cooled and filtered and the filtrate concentrated. The resulting concentrate is then subjected to silica gel chromatography, and those fractions as shown by thin layer chromatography to contain pure title compound are combined, yielding respectively the 3R or 3S epimer.

For 3R epimer NMR absorptions are observed at 3.21, 3.8–4.2, 4.9–5.6, 7.25–7.7, and 7.9–8.2 δ.

Following the procedure of Example 6, but using in place of the lactone starting material therein, the various 3-hydroxy lactones described following Example 5, there are prepared the corresponding 3-methoxy products.

EXAMPLE 7

3α-Benzoyloxy-5α-hydroxy-2β-[3R)-3-hydroxy-3-methyl-cis-1-octenyl]-1α-cyclopentaneacetic acid γ lactone.

Refer to Chart A.

A solution of 18 g. of 3α-benzoyloxy-5α-hydroxy-2β-(3-oxo-cis-1-octenyl)-1α-cyclopentaneacetic acid γ lactone in 890 ml. of dry benzene is cooled to 9° C. under a nitrogen atmosphere. A toluene solution of trimethylaluminum (60 ml.) is added over a period of 4 min. to the resulting mixture. This mixture is then stirred for 1.5 hr. at 20–25° C. then cooled to 10° C. Thereupon 370 ml. of saturated ammonium chloride is slowly added at such a rate so as to maintain the reaction mixture at ambient temperature. After 0.5 hr. the reaction mixture is diluted with ethyl acetate and water and filtered, the filter cake being washed with the ethyl acetate-water solvent. The aqueous layer is extracted with ethyl acetate and the combined organic extracts are washed with brine, dried over magnesium sulfate, and evaporated to yield 20 g. of an oil, which is chromatographed on one kg. of silica gel packed in 10 percent ethyl acetate and Skellysolve B. Elution with 10 to 16 percent ethyl acetate in Skellysolve B (18 l.), 28 percent ethyl acetate in Skellysolve B (8 l.) yields title compound. Fractions as shown by thin layer chromatography to contain pure product are combined. 5.3 g. of essentially pure 3S-epimer are obtained. Rechromatography, in the fashion described above, yields 3.9 g. of essentially pure 3R-epimer.

Omitting the chromatographic separation described above, the 3RS-epimeric mixture obtained on trimethylaluminum alkylation are separated in high yield as prostaglandin-type products.

Following the procedure of Example 7, but using in place of the 3 -oxo lactone starting material therein, the various lactones described following Example 4, there are obtained 3-hydroxy-3-methyl products corresponding to the 3-hydroxy products of Example 5.

EXAMPLE 8

3α,5α-Dihydroxy-2β-[(3R)-3-hydroxy-cis-1-octenyl]1α-cyclopentaneacetaldehyde, γ lactol, bis-tetrahydropyranyl ether (Formula XXVII: R₃ and R₄ of the L₁ moiety are hydrogen, M₆ is

R₇ is n-butyl, R₁₈ is tetrahydropyran-2-yloxy, and Y is cis—CH=CH—) and its 3S epimer.

Refer to Chart A.

A. A solution of 5 g. of the reaction product of Example 5 in 150 ml. of methanol is purged with nitrogen. Thereafter, potassium carbonate (2.02 g.) is added and the resulting mixture is stirred at ambient temperature until thin layer chromatographic analysis shows the solvolysis to be complete (about 1.5 hr.). The methanol is then evaporated under reduced pressure. The residue is then shaken with ethyl acetate (250 ml.), brine )250 ml.), and 8 g. of potassium bisulfate. The aqueous layer is then extracted twice with 125 ml. of ethyl acetate and the organic extracts are dried over magnesium sulfate, and evaporated to yield an oil. This oil is then dissolved in chloroform and a few crystals of p-toluenesulfonic acid are added. When thin layer chromatography indicates the action is complete (about 2 hr.), the reaction mixture is then washed with aqueous potassium bicarbonate, dried, and evaporated to yield an oil which is then chromatographed using silica gel packed in one percent ethanol in methylene chloride for purification. Accordingly, 3 g. of the deacylated lactone are prepared.

B. A solution of 1.57 g. of the reaction product of part A above, in 38 ml. of methylene chloride (containing 2.5 ml. of dihydropyran and 100 mg. of pyridine hydrochloride) is allowed to stand for 23 hr. at ambient temperature. The reaction mixture is then washed with water, aqueous potassium bicarbonate, dried over magnesium sulfate, and evaporated, yielding an oil which is thereafter chromatographed on 200 g. of silica gel packed in one percent acetone in methylene chloride. Elution with from one to ten percent acetone in methylene chloride yields 1.7 g. of the bis-tetrahydropyranyl lactone corresponding to the lactone reaction product of part A above.

C. A solution of the reaction product of part B above in 20 ml. of toluene is cooled to −70° C. and thereafter 10 ml. of 10 percent diisobutylaluminum hydride in toluene is slowly added. The reaction mixture is then stirred at −70° C. until thin layer chromatographic analysis indicates that the reduction is complete (about 30 min.). Thereafter the cooling bath is removed and 9 ml. of a mixture of tetrahydrofuran and water (2:1) is added slowly. The reaction mixture is then stirred and allowed to warm to room temperature, and is then filtered throgh Gelite. The filter cake is rinsed with benzene, combined organic extracts are then dried over magnesium sulfate and evaporated to yield 1.57 g. of the title compound. Rf equals 0.27 (ethyl acetate in cyclohexane, 1:1).

Following the procedure of Example 8, but using as starting material 3α-benzoyloxy-5α-hydroxy-2β-[(3R) or (3S)-3-hydroxy-3-methyl-cis-1-octenyl]-1α-cyclopentaneacetic acid γ lactone, there is obtained the corresponding bis-tetrahydropyranyl ether.

Following the procedure of Example 8, but using as starting material 3α-benzoyloxy-5α-hydroxy-2β-[4-(p-fluorophenoxy)-(3S)-hydroxy-cis-1-butenyl]-1α-cyclopentaneacetic acid γ lactone (1.47 g.) there is obtained the corresponding bis-tetrahydropyranyl ether (0.64 g.).

Following the procedure of Example 8, the 3α-benzoyloxy-5-hydroxy or 5- hydroxy lactones described in and following Example 5, 6, and 7 are transformed into corresponding lactols.

Following the procedure of Example 5, but using the title compound of Example 4 as starting material, there is prepared 3α-benzoyloxy-5α-hydroxy-2β-[(3S)-4,4-difluoro-3-hydroxy-cis-1-octenyl]-1α-cyclopentaneacetic acid γ lactone and its (3R) epimer.

Following the procedure of Example 8 there is prepared 3α,5α-dihydroxy-2β-[(3S)-3-hydroxy-4,4-difluoro-cis-1-octenyl]-1α-cyclopentane acetaldehyde γ lactol, bis-tetrahydropyranyl ether from the corresponding acylated lactone.

Following the procedure of Example 8, but using the reaction product of Example 6, there is prepared:

(a) 3α,5α-dihydroxy-2β-[(3R)-3-methoxy-cis-1-octenyl]-1α-cyclopentaneacetic acid γ lactone, 2.36 gm., from 3.95 gm. of starting material (NMR absorptions are observed at 3.31, 3.7–4.25, 4.81–5.15, and 5.15–5.75 δ);

(b) 5α-dihydroxy-2β-[(3R)-3-methoxy-cis-1-octenyl]-1α-cyclopentaneacetic acid γ lactone, tetrahydropyranyl ether 2.98 gm., from the 2.36 g. of the product of (a) above; and (c) 3α,5α-dihydroxy-2β-[(3R)- 3-methoxy-cis-1-octenyl]-1α-cyclopentaneacetaldehyde γ lactol, tetrahydropyranyl ether, 3.12 gm., from the 2.98 gm. of the product of (b) above.

EXAMPLE 9

3-Oxa-cis-13-PGF$_{1\alpha}$, 11,15-bis-(tetrahydropyranyl)ether, methyl ester (Formula XXXV: $h$ is one, R$_3$ and R$_4$ of the L$_1$ moiety are hydrogen, M$_6$ is

R$_7$ is n-butyl, R$_{18}$ is tetrahydropyranyloxy, and Y is cis—CH=CH—) or its 15-epimer.

Refer to Chart B.

A. The title compound of Example 8, (10.0 g.) is dissolved in 150 ml. of absolute ethanol (containing 3 drops of acetic acid). To this solution is added carbethoxymethylene-triphenylphosphorane (10 g.) and the mixture is stirred at ambient temperature for 72 hr. The resulting mixture is concentrated under reduced pressure to a volume of about 35 ml., mixed with ice, and dilute sodium bicarbonate solution, and shaken with ethyl acetate. The organic phase is washed with brine, dried over magnesium sulfate, and concentrated to yield a residue. The residue is slurried in 100 ml. of diethyl ether and filtered. The filtrate is concentrated to a residue which is subjected to silica gel chromatography, eluting with 20 to 40 percent ethyl acetate in Skellysolve B. There is obtained 2,3,4-trinor-cis-13-PGF$_{2\alpha}$, ethyl ester, bis(tetrahydropyranyl)ether.

B. The reaction product of step A above is mixed with the 5 percent palladium-on-charcoal catalyst (0.3 g.) in 30 ml. of ethyl acetate and hydrogenated at atmospheric pressure. When about 41 ml. of hydrogen is consumed, the catalyst is filtered off and the filtrate concentrated under reduced pressure to yield 2,3,4-trinor-cis-13-PGF$_{1\alpha}$, ethyl ester, bis(tetrahydropyranyl)ether.

C. The reaction product of step B above (1.1 g.) in 30 ml. of diethyl ether is added with stirring to a mixture of lithium aluminum hydride (0.3 g.) in 60 ml. of diethyl ether. The addition continues over a 10 min. period. The mixture is heated at reflux for 2 hr. then cooled, and treated with .035 ml. of water cautiously added. Thereafter 0.35 ml. of 15 percent aqueous sodium hydroxide solution is added, and thereafter one ml. of water. The solids are removed by filtration the filtrate is concentrated under reduced pressure to yield 2-decarboxy-2-hydroxymethyl-2,3,4-trinor-cis-13-PGF$_{1\alpha}$, bis-tetrahydropyranyl ether.

D. The reaction product of part C above (1.7 g.) together with 15 ml. of dimethyl sulfoxide and 5 ml. of tetrahydrofuran is treated with 2.28 ml. of 1.6 molar m-butyllithium in hexane, with stirring and cooling. After 5 min. there is added 5 ml. of dimethylformamide. The resulting solution is then stirred and cooled to 0° C. Thereafter lithium chloroacetate (0.7 g.) is added. The mixture is then stirred at 0° C. for 2 hr. and at about 25° C. for 22 hr. Thereafter the resulting solution is diluted with 200 ml. of ice-water, acidified with a cold solution of 3 ml. of concentrated hydrochloric acid in 50 ml. of water, and immediately extracted with dichloromethane. The organic phase is washed with cold water nd brine and dried over magnesium sulfate. Accordingly, there is prepared 3-oxa-cis-13-PGF$_{1\alpha}$, 11,15-bis-tetrahydropyranyl ether.

E. To the above solution is added excess ethereal diazomethane and after a few min. the excess reagent is destroyed with acetic acid. The mixture is then washed with a mixture of sodium bicarbonate solution and brine and thereafter with brine. The resulting solution is then dried and concentrated under reduced pressure. The residue so obtained is subjected to silica gel chromatography eluting with ethyl acetate and Skellysolve B to yield the title compounds.

Following the procedure of Example 9, but using the (3S) starting material there is obtained the corresponding 15-epi product.

Following the procedure of Example 9, but using the various lactols described following Example 8, there are obtained the corresponding products. For those lactols described following Example 8, wherein the C-3 position of the cyclopentane ring is unsubstituted, there are obtained the corresponding 11-deoxy products wherein the C-11 position is not etherified. When the 3-methoxy lactones described following Example 8 are employed there are obtained the corresponding prostaglandin-type products wherein the C-15 position is methoxy-substituted.

Following the procedure of Example 9, but omitting the etherification step (part E) there are obtained the above compounds in free acid form.

Following the procedure of Example 9, but replacing lithium chloroacetate used in part D of Example 9 with lithium chloropropionate or lithium chlorobutyrate, there are obtained the corresponding 3-oxa-PGF$_{1\alpha}$-type products wherein $h$ is 2 or 3. Further, using the various lactols described following Example 8, there are obtained the corresponding 3-oxa-cis-13-PGF$_{1\alpha}$-type products wherein $h$ is 2 or 3 when the above chloroalkanoates are substituted for lithium chloroacetate.

EXAMPLE 10

5-Oxa-cis-13PGF$_{1\alpha}$, methyl ester, 11,15-bis(tetrahydropyranyl) ether (Formula XLIII: g is two, R$_3$ and R$_4$ of the L$_1$ moiety are hydrogen, M$_6$ is

R$_1$ is methyl, R$_7$ is n-butyl, R$_{18}$ is tetrahydropyranyloxy, and Y is cis—CH=CH—) or its 15-epimer.

Refer to Chart C.

A. A mixture of the title product of Example 8 (6.3 g.) and 50 ml. of 95 percent ethanol is treated at 0° C. with stirring with a solution of sodium borohydride in 10 ml. of water (added over a period of one min.). The resulting mixture is then stirred at 0° C. for 10 min. and then shaken with 10 ml. of water, 250 ml. of ethyl acetate, and 150 ml. of brine. The organic phase is then washed with brine, dried, and concentrated under reduced pressure to yield 2-decarboxy-2-hydroxymethyl-2,3,4,5,6-pentanor-cis-13-PGF$_{1\alpha}$, 11,15-bis-tetrahydropyranyl ether.

B. A solution of potassium tert-butoxide (1.77 g.) in 30 ml. of tetrahydrofuran is mixed at 0° C., with stirring, with a solution of the reaction product of part A (5.8 g.) in 30 ml. of tetrahydrofuran. The resulting mixture is then stirred at 0° C. for 5 min. and thereafter 5 ml. of trimethyl ortho-4-bromobutyrate is added. Stirring is continued at 0° C. for 2 hr. and at about 25° C. for 16 hr. To this mixture is added 30 ml. of dimethylformamide and 0.5 g. of potassium-t-butoxide. The resulting mixture is then stirred for 20 hr. Some of the solvent is then removed under reduced pressure and the residue is then shaken with water and diethyl ether and difluoromethane (3:1). The organic phase is then washed with water and brine, dried, and and concentrated. The residue, containing the ortho ester, is dissolved in 6 ml. of methanol at 0° C. and treated with 15 ml. of cold water containing 2 drops of concentrated hydrochloric acid. The resulting mixture is then stirred at 0° C. for 5 min., shaken with 200 ml. of diethyl ether, 50 ml. of dichloromethane, and 200 ml. of brine. The organic phase is then washed with brine, dried, and concentrated under reduced pressure. The residue is subjected to silica gel chromatography, yielding the title compounds.

C. Trimethylortho-4-butyrate is prepared as follows:

Refer to S. M. McEldian, et al., *Juornal of the American Chemical Society* 64, 1825 (1942). A mixture of 4-bromobutyronitrile (74 g.), 21 ml. of methanol, and 150 ml. of diethyl ether is treated at 0° C. with stirring, with hydrogen bromide (40 g.). The mixture is then stirred for an additional 4 hr. at 0° C. and 100 ml. of hexane is added. The precipitated imino ester hydrobromide is separated from the liquid by filtration and washed with 400 ml. of diethyl ether in hexane (1:1). The imino ester salt is treated in 250 ml. of diethyl ether with 150 ml. of methanol and 25 ml. of methyl orthoformate, with stirring, at about 25° C. for 24 hr. The resulting mixture is then cooled to about 10° C. and the organic solution is separated from the ammonium bromide thereby formed. Diethyl ether (100 ml.) is then added. The resulting solution is then immediately and quickly washed with an ice cold solution prepared from potassium carbonate (20 g.) and 300 ml. of brine. The organic phase is washed with brine, treated with 3 drops of pyridine, and dried over anhydrous magnesium sulfate. The solution is then concentrated under reduced pressure, diluted with 150 ml. of benzene, and again concentrated. The residue is then distilled to yield the title ortho-4-bromobutyrate.

Following the procedure of part C of Example 10, but using 5-bromo pentanonitrile or 6- bromo hexanonitrile there is prepared trimethylortho-5-bromo pentanoate or trimethylortho-6-bromo hexanoate.

Following the procedure of Example 10, but using the corresponding (3R) lactone, there is obtained the corresponding 15-epi-PGF$_{1\alpha}$ -type product.

Following the procedure of Example 10, but using any of the various lactols described following Example 8, there is prepared the corresponding 5-oxa-cis-13-PGF$_{1\alpha}$ -type product. For those lactols wherein the C-3 position of the cyclopentane ring is unsubstituted, the corresponding PGF$_{1\alpha}$ type product is not etherified at the C-11 position. For those lactols described following Example 8, wherein the C-3 position of the side chain contains a methoxy group, the corresponding 3-oxa-cis-13-PGF$_{1\alpha}$ -type product contains no tetrahydropyranyl ether at the C-15 position.

Further, following the procedure of Example 10, but using trimethylortho-5-bromopentanoate or trimethylortho-6-bromohexanoate there is prepared the corresponding -5-oxa-cis-13-PGF$_{1\alpha}$ -type product wherein $g$ is 3 or 4.

EXAMPLE 11

4-Oxa-cis-13-PGF$_{1\alpha}$ $_{11,15}$ -bis(tetrahydropyranyl)ether (Formula LVIII: $h$ is one, $R_3$ and $R_4$ of the $L_1$ moiety are hydrogen, $M_6$ is

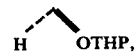

$R_1$ is hydrogen, $R_7$ is n-butyl, $R_{18}$ is tetrahydropyranyloxy, and Y is cis—CH=CH—).

Refer to Chart D.

A. A suspension of methoxymethyl-triphenylphosphonium chloride (32.4 g.) in 150 ml. of tetrahydrofuran is cooled to −15° C. To the suspension is added 69.4 ml. of n-butyl-lithium in hexane (1.6 molar) in 45 ml. of tetrahydrofuran. After 30 min. there is added a solution of 3α, 5α-dihydroxy-2β-[(3R)-hydroxy-cis-1-octenyl]-1α-cyclopentaneacetaldehyde γ lactol bis-(tetrahydropyranyl)ether, Example 8 (10 g.), in 90 ml. of tetrahydrofuran. The mixture is stirred for 1.5 hr. while warming to 25° C. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula LII product are combined.

B. The reaction product of part A above in 20 ml. of tetrahydrofuran is hydrolyzed with 50 ml. of 66 percent aqueous acetic acid at about 57° C. for 2.5 hr. The resulting mixture is then concentrated under reduced pressure. Toluene is added to the residue and the solution is again concentrated. Finally the residue is subjected to chromatography on silica gel, eluting with chloroform and methanol (6:1). The title compound is thereby obtained by combining and concentrating fractions as shown by thin layer chromatography to contain pure product. Accordingly, there is obtained the corresponding formula LIII δ-lactol.

C. Silver oxide is prepared by the addition of silver nitrate (1.14 g.) in water (3 ml.) dropwise to a 2 normal sodium hydroxide solution (6.8 ml.). A precipitate is formed. Added to the precipitate in ice water bath is the δ lactol of part B above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol), (9:1), pure product is removed by filtration. The filtrate is then extracted with diethyl ether. The aqueous layer is then chilled in an ice bath and acidified with 10 percent potassium bisulfate solution to pH less than 2. This aqueous mixture is then extracted with diethyl ether. The ethereal extracts are then combined, washed with brine, dried over magnesium sulfate, filtered, and evaporated under reduced pressure to yield the formula LIV lactone.

D. The formula LIV lactone prepared in part C above is then transformed to its bis-tetrahydropyranyl ether derivative following the procedure described in Example 8, part B.

E. The formula LV compound prepared in part D above is then reduced to the corresponding δ lactol bis-tetrahydropyranyl ether by the procedure described in Example b 8, part C.

F. The formula LVI lactol prepared in part E above is then transformed to the corresponding formula LVII primary alcohol by the procedure described in Example 10, part A.

G. The formula LVIII compound is prepared from the formula LVII compound by etherification of the primary alcohol moiety following the procedure described in Example 10, part B, but by substituting trimethylortho-3-bromopropionate in place of trimethylortho-4-bromobutyrate.

Following the procedure of Example 11, but using the corresponding (3R) starting material in place of the (3S) starting material there is obtained the corresponding 15-epi-PGF$_{1\alpha}$ -type product.

Following the procedure of Example 11, but using in step G, ortho-4-bromobutyrate or ortho-5-bromopentanoate in place of ortho-3-bromopropionate, there are obtained the corresponding formula LVIII compound wherein $h$ is 2 or 3.

Following the procedure of Example 11, but using in place of the formula LVI lactol, the various formula XXVII lactols described following Example 8, there are obtained the corresponding 4-oxa-cis-13-PGF$_{1\alpha}$ -type products.

EXAMPLE 12 cis-4,5-Didehydro-cis-13-PGF$_{1\alpha}$ , 11,15-bis-(tetrahydropyranyl)ether (formula LIX: $h$ is one, R$_3$ and R$_4$ of the L$_1$ moiety are hydrogen, M$_6$ is

R$_1$ is hydrogen, R$_7$ is n-butyl, R$_{18}$is tetrahydropyranyloxy, and Y is cis—CH=CH—) and its 15-epimer.

Refer to Chart D.

A. Following the procedure of Example 11, parts A, B. C, D, and E there is prepared the formula LVI lactol wherein L$_1$, M$_6$, R$_7$, R$_{18}$, and Y are as defined for the title compound.

B. 3-Carboxypropyltriphenylphosphonium bromide (prepared by heating 4-bromobutyric acid and triphenylphosphine in benzene at reflux for 18 hr., and thereafter purifying), 106 g., is added to sodiomethylsulfinylcarbanide prepared from sodium hydride (2.08 g., 57 percent) and 30 ml. of dimethylsulfoxide. The resulting Wittig reagent is combined with the formula LVI lactol of part A above and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate and isomeric hexanes (3:1). Those fractions as shown to contain the desired compound by thin layer chromatography are combined to yield pure product.

Following the procedure of Example 12, but using in place of the (3S) starting material the corresponding (3R) starting material there is obtained the corresponding 15-epi-cis-13-PGF$_{1\alpha}$ -type compound.

Following the procedure of Example 12, but using in place of the 3-carboxypropyltriphenylphosphonium bromide, 4-carboxybutyltriphenylphosphonium bromide, or 5-carboxypentyltriphenylphosphonium bromide, there are prepared the corresponding formula LIX compounds wherein $h$ is 2 or 3.

Further, following the procedure of Example 12, but using in place of the formula LI starting material the various formula XXVII lactols described following Example 8, there are prepared the corresponding cis-4,5-didehydro-13-cis-PGF$_{1\alpha}$ -type products.

EXAMPLE 13

Cis-13-PGF$_{2\alpha}$, methyl ester, 11,15-bis-tetrahydropyranyl ether (Formula LXIII: $g$ is 2, R$_3$ and R$_4$ of the L$_1$ moiety are hydrogen, M$_6$ is

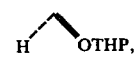

R$_1$ is methyl, R$_2$is hydrogen, R$_7$ is n-butyl, R$_{18}$ is tetrahydropyranyloxy, and Y is cis—CH=CH—) and its 15-epimer.

Refer to Chart E.

A. Sodium hydride (0.57 g., 57 percent in mineral oil) in 25 ml. of dimethylsulfoxide, is added to 3 g. of 4-carboxybutyltriphenylphosphonium bromide. The reaction mixture is maintained at 20° C. with stirring for 30 min. A solution of the title compound of Example 8 (1.57 g.) in 10 ml. of dimethylsulfoxide is added. The reaction mixture is stirred at ambient temperature for 2 hr. and diluted with 50 ml. of benzene. Potassium bisulfate (2.7 g. in 30 ml. of water) is slowly added, maintaining the reaction temperature at less than or equal to 10° C. The aqueous layer is extracted with 50 ml. of benzene and the organic extracts are washed successfully with 50 ml. of water and 50 ml. of brine before combining, drying, and evaporating. Evaporation yields an oil which is chromatographed on 100 g. of acid washed silica gel packed in 20 percent ethyl acetate and Skellysolve B. Elution with 20–75 percent ethyl acetate and Skellysolve B yields 1.68 g. of crude 13-cis-PGF$_{2\alpha}$ 11,15-bis-tetrahydropyranyl ether.

B. A solution of the crude reaction product of part A above and 15 ml. of diethyl ether is esterified with diazomethane, used in stoichiometric excess. The crude methyl ester is chromatographed on 100 g. of silica el packed in 2 percent acetone methylene chloride. Elution with 2–12 percnt acetone in methylene chloride yields 1.2 g. of the title compound.

Following the procedure of Example 13, but using the (3R) lactol there is obtained the corresponding 15-epi-cis-13-PGF$_{2\alpha}$ , methyl ester, 11,15-bis-tetrahydropyranyl ether.

Following the procedure of Example 13, but using 5-carboxypentyltriphenylphosphonium bromide or 6-carboxyhexyltriphenylphosphonium bromide in place of 4-carboxybutyltriphenylphosphonium bromide there is obtained the corresponding 2a-homo or 2a,2b-dihomo-cis-13-PGF$_{2\alpha}$ -type compound or its 15-epimer.

Further, following the procedure of Example 13, but bromide, 4,4-difluoro-4-carboxybutyltriphenylphosphonium bromide 3,3-difluoro-4-carboxybutyltriphenylphosphonium bromide there is obtained the corresponding 2,2-difluoro-cis-13-PGF$_{2\alpha}$ -type tetrahydropyranyl ether or its 15-epimer.

Further, following the procedure of Example 13, but using 3α,5α-dihydroxy-2β-[(3R)-3-methoxy-cis-1-octenyl]-1α-cyclopentaneacetaldehyde δ lactol tetrahydropyranyl ether (3.12 gm), there is prepared 3.515 gms. of 15-epi-cis-13-PGF$_{2\alpha}$ , 11-tetrahydropyranyl ether, 15-methyl ether, which is optionally methyl esterified to yield 15-epi-cis-13-PGF$_{2\alpha}$ , 11-tetrahydropyranyl ether, 15-methyl ether, methyl ester, 3.134 gms. (NMR absorptions are observed at 3.35 g 3.67, 3.2–4.4, 4.6–4.8, and 5.15–5.8 δ.)

Further, following the procedure of Example 13, but using in place of the formula VIII lactol starting material therein one of the various lactols described following Example 8, there are prepared the corresponding cis-13- or 11-deoxy-cis-13-PGF$_{2\alpha}$ -type products.

For example, 0.28 g. of 15-epi-16-(p-fluorophenoxy)17,18,19,20-tetranor-cis-13-PGF$_{2\alpha}$ , methyl eter, 13,15-bis-tetrahydropyranyl ether is obtained from 0.64 g. of corresponding lactol.

EXAMPLE 14

15-Methyl-cis-13-PGF$_{2\alpha}$ , methyl ester (Formula LXXVI: R$_3$ and R$_4$ of the L$_1$ moiety are hydrogen, M$_1$ is

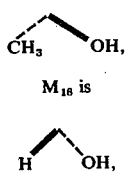

M$_{18}$ is

R$_1$ is methyl, R$_7$ is n-butyl, R$_8$ is hydrogen, Y is cis—CH=CH—, and Z$_1$ is cis—CH=CH(CH$_2$)$_3$-) or its 15-epimer.

A. A solution of 5.7 g. of the reaction product of Example 7, 3α-benzoyloxy-5α-hydroxy-2β-[(3S)-3-hydroxy-3-methyl-cis-1-octenyl]-1α-cyclopentaneacetic acid γ lactone in 150 ml. of methanol is deacylated according to the procedure of Example 8, part A, yielding 3.7 g. of 3α,5α-dihydroxy-2β-[(3S)-3-hydroxy-3-methyl-cis-1-octenyl]-1α-cyclopentaneacetic acid γ lactone.

A 3.9 g. sample of the corresponding (3R) starting material is deacylated in a similar fashion, yielding 2.6 g. of the coresponding (3R) product.

B. A solution of 3.65 g. of the reaction product of part A in 150 m. of tetrahydrofuran is cooled to −60° C. Diisobutylaluminum hydride and toluene (85 ml.) is added over a period of 23 min. at a temperature of −70° C. The reaction mixture is stirred for an additional 24 min. Thereafter 100 ml. of saturated aqueous ammonium chloride solution is slowly added at a temperature of −60° C. The resulting mixture is then stirred and allowed to warm to room temperature, yielding a gelatin as precipitate. This mixture is then diluted with 70 ml. of water and 150 ml. of ethyl acetate, mixed thoroughly and filtered. The filter cake is washed with water and ethyl acetate. The aqueous layer is extracted with ethyl acetate. The combined organic extracts are washed with brine, dried over sodium sulfate, and evaporated to yield 3.9 g. of the lactol corresponding to lactone starting material as a cloudy oil.

C. Following the procedure of Example 13, sodium hydride in dimethylsulfoxide is combined with 4-carboxybutyltriphenylphosphonium bromide to yield the title compound in free acid form.

The reaction product of part C above is esterified with diazomethane following the procedure described above, yielding 2.65 g. of the title compound as a yellow oil. The mass spectrum shows base peak absorption at 598.3913 and other peaks at 583, 527, 508, 593, 477, 418, and 317. Infrared absorptions (cm.$^{-1}$) are observed at 3360, 3000, 2940, 2860, 1740, 1725, 1655, 1460, 1435, 1365, 1315, 1245, 1220, 1165, 1150 1125, 1085, and 1035. NMR absorptions (CDCl$_3$ solutions) are observed at 1.31, 3.66, and 4.85–5.8 δ.

Following the procedure of steps B-D above, but using the deacylated (3R)-lactone (2.6 g.) there is obtained 1.25 g. of 15-epi-15-methyl-cis-13-PGF$_{2\alpha}$ , methyl ester. The mass spectrum shows base peak absorption at 598.3907 and other peaks at 585, 567, 527, 508, 493, 477, 418, 328, and 317. Infrared absorptions are observed (cm.$^{-1}$) 3340, 3000, 1740, 1650, 1350, 1300, 1285, 1240, 1175, 1140, 1125, 1055, 1030, 995, 935, and 745. NMR absorptions (CDCl$_3$ solutions) are observed at 1.35, 3.68, and 4.95–5.8.

The preparation of the above title compound or its 15-epimer is optionally accomplished following the procedure of Chart F. Accordingly, the 3(RS)-3-methyl lactone corresponding to Example 7 is prepared by omitting the chromatographic separation step therein. Thereafter, by the procedure of Example 8 the corresponding 3(RS)-3-methyl lactol is prepared. Thereafter, following the procedure of Example 13, the (15RS)-15-methyl-cis-13-PGF$_{2\alpha}$ -bis-tetrahydropyranyl ether, methyl ester is prepared by methyl esterification of the free acid so formed. The tetrahydropyranyl ether moieties may then be hydrolyzed and the C-15 epimers separated by chromatographic techniques.

Following the procedure of Example 14, or the optional procedure discussed above, there are prepared 15-epi-15-methyl or 15-methyl-cis-13-PGF$_{2\alpha}$ -type compounds from the corresponding lactols described following Example 8.

Further, using the compounds described in or following Examples 9, 10, 11, 12, or 13 there are prepared the corresponding 3-oxa-, 4-oxa-, 5-oxa- or cis-4,5-dedehydro-15-methyl- or 15-epi-15-methyl-cis-13-PGF$_{2\alpha}$ -type products.

EXAMPLE 15

15-Methyl-cis-13-PGF$_{2\alpha}$ (Formula LXXVI: R$_3$ and R$_4$ of the L$_1$ moiety are hydrogen, M$_1$ is

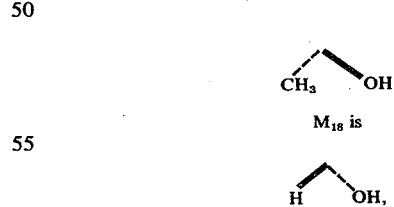

R$_1$ is hydrogen, R$_7$ is n-butyl, R$_8$ is hydroxy, Y is cis—CH=CH—, and Z is cis—CH=CH—(CH$_2$)$_3$—) or its 15-epimer.

A solution of 2.0 g. of the reaction product of Example 14, or its 15-epimer, in 20 ml. of methanol is cooled to 0° C. The resulting mixture is thereafter treated dropwise under a nitrogen atmosphere with 12 ml. of 10 percent aqueous sodium hydroxide solution. The mixture is then allowed to warm to room temperature and stirred for 2 hr. After removal of the methanol by evaporation under reduced pressure the residue is diluted with water and extracted with methylene chloride. The aqueous layer is then cooled with ice, treated with 24 ml. of 2 molar aqueous sodium bisulfate solution and extracted immediately with ethyl acetate. The combined organic extracts are washed with brine, dried over anhydrous sodium sulfate, and concentrated. Crude product may then be chromatographed on 150 g. of silica gel, yielding the title compound or its 15-epimer.

Following the procedure of Example 15, but using any of the 15-methyl-cis-13-$PGF_{2\alpha}$ or 11-deoxy-15-methyl-cis-13-$PGF_{2\alpha}$-type methyl esters, there are prepared the corresponding free acid products.

EXAMPLE 16

Cis-13-$PGF_{2\alpha}$ (formula LXXVI: $R_3$ and $R_4$ of the $L_1$ moiety are hydrogen, $M_1$ is

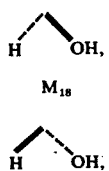

$M_{18}$ $R_1$ is hydrogen, $R_7$ is n-butyl, $R_8$ is hydroxy, Y is cis—CH=CH—, and $Z_1$ is cis—CH=CH—$(CH_2)_3$—) or its 15-epimer.

Cis-13-$PGF_{2\alpha}$-bis-tetrahydropyranyl ether (0.60 g.) is reacted with 30 ml. of tetrahydrofuran, water, and acetic acid (1:3:6) at 40° C. for 4 hr. Thereafter, the resulting mixture is diluted with 60 ml. of water and freeze dried. The residue is then extracted with diethyl ether and washed with aqueous potassium bicarbonate and brine. The diethyl ether extract is then dried using magnesium sulfate and evaporated to yield an oil which is chromatographed to yield pure product.

Using corresponding 15-epimeric starting material the corresponding 15-epimeric product is prepared. Melting point 109°–110.8° C.

Following the procedure of Example 16, but using the corresponding 16,16-difluoro-cis-13-$PGF_{2\alpha}$, methyl ester, bis-tetrahydropyranyl ether, or its 15-epimer, there are prepared the corresponding $PGF_{2\alpha}$-type products. For the 15-epi compound infrared absorptions are observed at (cm.$^{-1}$) 3360, 1735, 1720, 1655, 1435, 1315, 1240, 1205, 1165, 1120, 1085, 1050, 1010, 915, 840, and 770. NMR absorptions in $CDCl_3$ are observed at 3.65, 3.6–5.0, and 5.25–6.05 δ. Mass spectral base peak for the trimethylsilyl derivative is observed 585.3152. For the 15β compound infrared absorptions are observed (cm.$^{-1}$) 3420, 3000, 1725, 1655, 1435, 1315, 1245, 1220, 1205, 1180, 1115, 1085, 1045, 1005, 910, 835, and 760. Mass spectral base peak absorptions for the trimethylsilyl derivative is observed at 620.3535. Other mass spectral peaks are observed at 605, 600, 530, 513, 510, 440, 423, and 363.

Following the procedure of Example 16, but using the methyl ester of the indicated starting material therein, or its 15-epimer, there are prepared the corresponding methyl esterified products. For the 15β-hydroxy product MNR absorptions in $CDCl_3$ are observed at 3.68, 3.58–4.7, and 4.9–5.85. Mass spectral base peak absorption is observed at 584.3748. Other mass spectral peaks are observed at 569, 553, 513, 494, 423, 404, 314, 217, and 173. For the 15-epimer NMR absorptions in $CDCl_3$ are observed at 3.66, 3.6–4.92, and 5.08–5.93 δ. Mass spectral base peak absorption is observed at 584.3741. Other mass spectral peaks are observed at 539, 553, 513, 494, 423, 404, 217, and 173.

Following the procedure of Example 16, but using 15-epi-cis-13-16-(p-fluorophenoxy)-17,18,19,20-tetraranor-$PGF_{2\alpha}$, methyl ester, bis-tetrahydropyranyl ether, there is obtained the corresponding $PGF_{2\alpha}$-type product. Mass spectral base peak absorption is observed 638.3289. Other mass spectral peaks are observed at 623, 607, 548, 533, 513, 423, 397, 307, and 217. NMR absorptions in $CDCl_3$ are observed at 3.62, 5.2–6.0, and 6.7–7.2 δ.

Following the procedure of Example 16, but using 15-epi-cis-13-$PGF_{2\alpha}$, 11-tetrahydropyranyl ether, 15-methyl ether methyl ester (0.5 gm.) as starting material, there is obtained 15-epi-cis-13-$PGF_{2\alpha}$, 15-methyl ether, methyl ester (0.158 gm.). The NMR spectrum shows absorption at 3.31, 3.68, 3.2–4.5, and 5.1–5.85 δ.

Following the procedure of Example 16, but using as starting material any of the 11,15-bis-tetrahydropyranyl ethers, 11-tetrahydropyranyl ethers, or 15-tetrahydropyran-yl esters described in and following Examples 9, 10, 11, 12, or 13, there are prepared respectively the corresponding cis-13-$PGF_{2\alpha}$-15-methyl ether, cis-13-$PGF_{2\alpha}$-, or 11-deoxy-cis-13-, or 15-methyl ether cis-13-$PGF_{2\alpha}$-type compounds.

EXAMPLE 17

15-Methyl-cis-13-$PGE_2$, methyl ester, (Formula LXXVI : $R_3$ and $R_4$ of the $L_1$ moiety are hydrogen, $M_1$ is $M_{18}$ is O, $R_1$ is methyl, $R_7$ is n-butyl, $R_8$ is hydroxy, Y is cis—CH=CH-, and $Z_1$ is cis—CH=CH—$(CH_2)_3$—) or its 15-epimer.

A. A solution of 15-methyl-cis-13-$PGF_{2\alpha}$, methyl ester, 11,15-bis-tetrahydropyranyl ether, prepared above, in 60 ml. of acetone is cooled to −25° C. Thereupon 1.9 ml. of Jones reagent is added. The reaction mixture is then stirred for 25 min. at −25° C. and isopropyl alcohol (1.9 ml.) is added after an additional 15 min. at −25° C. the reaction mixture is diluted with 200 ml. of water (0° C.) and extracted with diethyl ether. Ethereal extracts are washed with 75 ml. of cold 0.1 normal potassium bicarbonate, 150 ml. of brine, dried over magnesium sulfate, and evaporated, thereby yielding 15-methyl-cis-13-$PGF_2$, methyl ester, 11,15-bis-tetrahydropyranyl ether.

B. A solution of the crude product of part A above is reacted with 16 ml. of tetrahydrofuran, water, and acetic acid (1:3:6) and allowed to stand at 40° C. for 4 hr. The resulting mixture is thereafter diluted with 120 ml. of water and freeze dried. The residue is dissolved in diethyl ether and washed with potassium bicarbonate, brine, and thereafter dried and evaporated to yield crude product. The crude product is chromatographed on 25 g. of silica gel packed in 5 percent acetone in methylene chloride. Elution with 5 to 40 percent acetone in methylene chloride yields the pure product.

Following the above procedure but using 15-epimeric starting material, the corresponding 15-epimer is prepared.

Following the procedure of Example 17, but using the various 15-methyl-cis-13-$PGF_{2\alpha}$, methyl ester, 11,15-bis-tetrahydropyranyl ethers, or 15-tetrahydropyranyl ethers, as prepared in or following Example 9, 10, 11, 12, and 13 there are prepared the corresponding products.

EXAMPLE 18

15-Methyl-cis-13-$PGE_2$ or its 15-epimer.

The title compound is prepared by enzymatic hydrolysis of the methyl ester of the reaction product of Example 17 or its 15-epimer.

The enzyme is prepared as follows:

Freshly harvested colony pieces of *plexaura homomalla*(Esper), 1792, forma S (10 kg.), are chopped into pieces less than 3 cm. in their longest dimension and then covered with about 3 volumes (20 l.) of acetone. The mixture is stirred at about 25° C. for 1 hr. The solids are separated by filtration, washed with a quantity of acetone, air dried, and finally stored at about 20° C. as a coarse enzymatic powder.

The esterase hydrolysis then proceeds as follows:

The suspension of the esterase composition prepared above in 25 ml. of water is combined with a solution of the above indicated starting material. 8 ml. of methanol is added, and the resulting mixture is stirred at about 25° C. for 24 hr. 50 ml. of acetone is then added and the mixture is stirred briefly, filtered, and the filtrate is then concentrated under reduced pressure. The aqueous residue is then acidified to pH 3.5 with citric acid and extracted with dichloromethane. The combined extracts are concentrated under reduced pressure to yield the title acid.

Following the procedure of Example 18, but using the various methyl esters described following Example 17, the corresponding products are prepared.

EXAMPLE 19 cis-13-$PGE_2$, methyl ester, or its 15-epimer.

Following the procedure of Example 17, but using cis-13-$PGF_{2\alpha}$, methyl ester, 11,15-bis-tetrahydropyranyl ether as starting material the title product is obtained. Mass spectral base peak absorption is observed at 510.3198. NMR absorptions in $CDCl_3$ are observed at 3.63, 3.6–4.6, and 5.1–5.9 $\delta$.

Using the 15-epimer of the above indicated starting material the corresponding 15-epimeric product is prepared. NMR absorptions in $CDCl_3$ are observed at 3.62, 3.5–5.15, and 5.15–5.92 $\delta$. Mass spectral base peak absorption is observed at 510.3188 and other mass spectral peaks are observed at 495, 492, 479, 439, 420, 389, 349, 330, and 295.

Following the procedure of Example 17, but using the corresponding 16,16-difluoro cis-13-$PGF_{2\alpha}$, methyl ester 11,15-bis-tetrahydropyranyl ether, or its 15-epimer, there is prepared respectively 16,16-difluoro-cis-13-$PGE_2$, methyl ester or 15-epi-16,16-difluoro-cis-13-$PGE_2$, methyl ester.

The 15-epimer compound exhibits infrared absorption at (cm.$^{-1}$) 3390, 1740, 1655, 1440, 1350, 1315, 1245, 1220, 1205, 1160, 1080, 1050, 1010, 915, 835, and 775. NMR absorptions in $CDCl_3$ are observed at 3.68, 3.60–5.0, 5.38, and 5.84 $\delta$. Mass spectral base peak absorption is observed at 475.2587. The 15$\alpha$-hydroxy compounds exhibits mass spectral base peak absorption at 546.2998, and other mass spectral peaks at 531, 528, 526, 511, 456, 439, and 436. Infrared absorptions are observed at (cm.$^{-1}$) 3460, 1470, 1440, 1315, 1245, 1220, 1205, 1155, 1070, 1010, and 8.35.

Following the procedure of Example 17, but using 15-epi-cis-13-$PGF_{2\alpha}$, 11-tetrahydropyranyl ether, 15-methyl ether, methyl ester (2.6 gm.), there is obtained 15-epi-cis-13-$PGE_2$, 15-methyl ether, methyl ester (1.947 gm.). NMR absorptions are observed at 3.35, 3.69, 3.7–4.5, and 5.15–5.9 $\delta$.

Following the procedure of Example 19, but using the various $PGF_{2\alpha}$, $PGF_{2\alpha}$ -11,15-bis-tetrahydropyranyl ether, $PGF_{2\alpha}$ -15-tetrahydropyranyl ether, or $PGF_{2\alpha}$ -11-tetrahydropyranyl ether type compounds described in and following Examples 9, 10, 11, 12, and 13, there are prepared the corresponding $PGE_2$ or 11-deoxy-$PGE_2$-type products optionally substituted at C-15 with a methoxy group.

EXAMPLE 20 cis-13-$PGF_{1\alpha}$, methyl ester, or its 15-epimer.

A solution of 4.8 g of cis-13-$PGF_{2\alpha}$, methyl ester in 90 ml. of acetone and 60 ml. of benzene containing 0.75 g. of tris(triphenylphosphine)rhodium (1) chloride is shaken under hydrogen atmosphere at ambient temperature at 1 to 3 atmospheres pressure for 3.5 hr. Thereafter the solvent is evaporated and the residue chromatographed on 400 g. of silica gel packed in methylene chloride eluting with one to 6 percent methanol in methylene chloride. There is recovered 0.90 g. of impure product. The above product is purified using silica gel chromatography, thereby preparing sure product. Mass spectral base peak absorption is observed at 586.3912, and other mass spectral peaks are observed at 571, 555, 515, 496, 481, 465, 425, 399, 380, 210, and 173. NMR absorptions in $CDCl_3$ are observed at 3.65, 3.5–4.7, and 4.9–5.8 $\delta$.

Following the above procedure, but using 15-epi-cis-13-$PGF_{2\alpha}$, methyl ester, there is prepared the corresponding 15-epi-cis-13-$PGF_{1\alpha}$, methyl ester. Mass spectral base peak absorption is observed at 586.3889, and other mass spectral peaks are observed at 571, 555, 515, 496, 425; and 217. Infrared absorption is observed at 3520, 1735, 1655, 1435, 1320, 1305, 1260, 1220, 1195, 1170, 1025, and 975 cm.$^{-1}$.

Following the procedure of Example 20, but using as starting material 15-methyl-cis-13-$PGF_{2\alpha}$, methyl ester, or its 15-epimer, there are prepared the corresponding 15-methyl products. For the 15$\beta$ compound mass spectral base peak absorption is observed at 600.4074, and other mass spectral peaks are observed at 585, 525, 510, 495, 479, 457, 439, 420, 367, and 217. NMR absorptions are observed in $CDCL_3$ solutions at 1.31, 3.65, 5.22, and 5.51 $\delta$.

For the 15-epimer mass spectral base peak absorption is observed at 600.4068, and other mass spectral peaks are observed at 585, 569, 529, 510, 457, 420, 367, and 217. NMR absorptions are observed in $CDCl_3$ solutions at 5.22 and 5.57 $\delta$.

Following the procedure of Example 20, but using in place of the indicated starting material any of the $PGF_{2\alpha}$ or 11-deoxy-$PGF_{2\alpha}$ -type compounds described in or following Example 13, there are prepared the corresponding $PGF_{1\alpha}$ or 11-deoxy-$PGF_{1\alpha}$ -type products.

EXAMPLE 21 cis-13-$PGE_1$, methyl ester, or is 15-epimer.

The title compound of this Example is prepared by oxidation of the compound of Example 20, using the procedure described in Examfple 17, part A.

Using the corresponding 15-epimer, there is prepared 15-epi-cis-13-$PGE_1$, methyl ester.

Following the procedure of Example 21, but using any of the $PGF_{1\alpha}$ -type compounds described following Example 20, there are prepared the corresponding PGE$_1$-type compounds.

Accordingly, following the procedures of Example 14–21 there are prepared the various PGF$_{2\alpha}$ -, 2,2-difluoro-PGF$_{2\alpha}$ -, 2a,2b-dihomo-PGF$_{2\alpha}$ -, 3-oxa-PGF$_{1\alpha}$ -, 5-oxa-PGF$_{1\alpha}$ -, 4-oxa-PGF$_{1\alpha}$ -, cis-4,5-didehydro-PGF$_{1\alpha}$ -, PGF$_{1\alpha}$ -, 2,2-difluoro-PGF$_{1\alpha}$ -, or 2a,2b-dihomo-PGF$_{1\alpha}$ -type compounds or the corresponding PGE-type compounds, optionally substituted at C-15 with methyl or methoxy, at C-16 with one or 2 methyl, or one or 2 fluoro, or phenoxy, or optionally substituted at C-17 with a phenyl or substituted phenyl moiety.

EXAMPLE 22 cis-13-PGF$_{2\beta}$ , methyl ester (Formula LXXVII: R$_3$ and R$_4$ of the L$_1$ moiety are hydrogen, M$_1$ is

R$_1$ is methyl, R$_7$ is n-butyl, R$_8$ is hydroxy, Y is cis—CH=CH—, and Z$_1$ is cis—CH=CH—(CH$_2$)$_3$—). Refer to Chart F.

A solution of 0.3 g. of cis-13-PGE$_2$, methyl ester, (Example 19) in 15 ml. of methanol is cooled to −15° C. Therafter 16 mg. of borohydride is added. After 45 min., 2 ml. of 50 percent acetic acid in water is slowly added. The reaction mixture is then allowed to warm to ambient temperature and then evaporated at reduced pressure. The residue due is then shaken with ethyl acetate and water. The organic phase is then washed with aqueous sodium bicarbonate, brine, and the dried and evaporated to yield 0.3 g. of an oil. A column of 25 g. of silica gel packed in ethyl acetate is eluted with 70–100 percent ethyl acetate in cyclohexane. Crude product is then rechromatographed eluting with 0.5 to 3 percent methanol in methylene chloride. Rechromatographing in similar fashion yields 0.116 g. of the 9β-epimer. NMR absorptions of the CDCl$_3$ solutions are observed at 3.68, 3.6–6, and 5.1–5.8 δ. Mass spectral base peak absorption is observed at 584.3735.

Using the corresponding 15-epimeric starting material the corresponding 15-epimeric product is prepared. NMR absorptions of CDCl$_3$ solutions are observed at 3.68, 3.55–5.75, and 5.16–5.83 δ. Mass spectral base peak absorption is observed at 584.3735.

Following the procedure of Example 22, but using 15-epi-cis-13-PGF$_{2\beta}$ , methyl ester, 15-methyl ester (0.497 gm.) as starting material, there is prepared 15-epi-cis-13-PGF$_{2\beta}$ , 15-methyl ether, methyl ester (0.209 gm.). NMR absorptions are observed at 3.30, 3.65, 3.6–4.4, and 5.2–5.85 β.

Following the procedure of Example 22, but using the various PGE$_2$, 11-deoxy-PGE$_2$, PGE$_1$, or 11-deoxy-PGE$_1$, products described in the preceding examples, there are obtained the corresponding PGE$_{2\beta}$ or PGF$_{1\beta}$ products.

EXAMPLE 23 cis-13-PGA$_2$ (Formula LXXVIII: R$_3$ and R$_4$ of the L$_1$ moiety are hydrogen, M$_1$ is

R$_1$ is hydrogen, R$_7$ is n-butyl, Y is cis—CH=CH—, and Z$_1$ is cis—CH=CH—(CH$_2$)$_3$—).

Refer to Chart F.

A solution of cis-13-PGE$_2$ (300 mg), 4-ml. of tetrahydrofuran, and 4 ml. of 0.5 normal hydrochloric acid is left standing at ambient temperature for 5 days. Brine and dichloromethane in ether (1:3) are added and the mixture is stirred. The organic phase is separated, dried, and concentrated. The residue is dissolved in diethyl ether and the solution is extracted with aqueous sodium bicarbonate. The aqueous phase is acidified with dilute hydrochloric acid and then extracted with dichloromethane. This extract is then dried and concentrated to yield the title compound.

Following the procedure of Example 23, but using any of the PGE$_2$-or PGE$_1$-type compounds described above there are respectively prepared the corresponding PGA$_2$- or PGA$_1$-type compounds.

EXAMPLE 24 cis-13-PGB$_2$ (Formula LXXX: R$_3$ and R$_4$ of the L$_1$ moiety are hydrogen, M$_1$ is

R$_1$ is hydrogen, R$_7$ is n-butyl, Y is cis—CH=CH—, and Z$_1$ is cis—CH=CH—(CH$_2$)$_3$—).

Refer to Chart F.

A solution of cis-13-PGE$_2$ (200 mg.) and 100 ml. of 50 percent aqueous methanol containing about 1 g. of potassium hydroxide is kept at ambient temperature for 10 hr. under nitrogen atmosphere. The resulting solution is then cooled to 10° C. and neutralized by addition of 3 normal hydrochloric acid at 10° C. This solution is then extracted repeatedly with ethyl acetate and the combined organic extracts are washed with water, then washed with brine, dried, and concentrated to yield the title compound.

Following the procedure of Example 24, but using any of the PGE$_2$ or PGE$_1$-type compounds described in the above Examples, there are prepared the corresponding PGE$_2$ and PGB$_1$-type compounds.

EXAMPLE 25 cis-13-PGF$_{2\alpha}$ sodium salt

A solution of cis-13-PGF$_{2\alpha}$ (100 mg.) in 50 ml. of water ethanol mixture (1:1) is cooled at 5° C. and neutralized with an equivalent amount of .1 normal aqueous sodium hydroxide solution. The neutral solution is then concentrated to a residue of the title compound.

Following the procedure of Example 25, using potassium hydroxide, calcium hydroxide, tetramethyl ammonium hydroxide, or benzyl trimethyl ammonium hydroxide in place sodium hydroxide there is obtained the corresponding salt of cis-13-PGF$_{2\alpha}$ . Likewise following the procedure of Example 24 each of the various other prostaglandin-type acids described above is transformed to the corresponding sodium potassium calcium trimethylammonium or benzyltrimethylammonium salt.

EXAMPLE 26

15-epi-16,16-Dimethyl-13-PGF$_{2\alpha}$ , methyl ester; 15-epi-16,16-dimethyl-cis-13-PGE$_2$, methyl ester; 15-epi-16,16-dimethyl-cis-13 -PGF$_{2\beta}$ , methyl ester; or 15-epi-11-deoxy-16,16-dimethyl-cis-13-PGE$_2$, methyl ester.

A. Following the procedure of Example 4, 3α-benzoyloxy-5α-hydroxy -2β-(4,4-dimethyl-3-oxo-cis-1-octenyl)-1α-cyclopentanceactic acid γ-lactone is prepared by photoisomerization of the corresponding trans lactone. Accordingly, crystallization of the product (using diethyl ether in pentane) yields 3.14 g. of white crystals (melting point 93°–95° C.) from 25 g. of trans starting material. NMR absorptions are observes at 3.7–4.15, 4.9–5.5, 5.94, 6.53, 7.2–7.65 and 7.8–8.15 δ. Following the procedure of Example 5, 6.0 g. of the above 3-oxo-cis unsaturated lactone (6.0 g.) is reduced, yielding a (3S)-3-hydroxy lactone (3.17 g.) and a (3R)-3-hydroxy lactone (1.32 g.). These epimeric alcohols exhibit similar NMR absorption, as follows: 0.84, 0.90, 4.03–4.34, 4.95–5.95, 7.3–7.7, and 7.9–8.2 δ.

B. Nitrogen is bubbled through a solution of the reaction product of part A above (3.1 g.) in 70 ml. of dry methanol. Thereafter 6 ml. of methanolic sodium methoxide (25.8 mmol.) is added. After 30 min. the acetic acid (1.5 ml.) is added and the reaction mixture is evaporated under reduced pressure. The residue is shaken with ethyl acetate and water and the organic phase washed with aqueous potassium bicarbonate, brine, and then allowed to dry over magnesium sulfate. This product is then evaporated to a yellow oil (3.0 g.) which is chromatographed on 300 g. of silica gel packed in 5 percent acetone in methylene chloride. Elution with 5 to 50 percent acetone in methylene chloride yields 2.17 g. of 3α,5α-dihydroxy-2β-[(3)-3-hydroxy-4,4-dimethyl-cis-1-octenyl]-1α-cyclopentaneacetic acid γ-lactone. NMR absorptions are observed at 0.84, 0.89, 3.1–3.46, 3.7–5.1–6.1 δ. The mass spectrum for the trimethylsilyl derivative shows base peak absorption 425.2562. A solution of the reaction product of the preceding paragraph (2.17 g.) in 73 ml. of methylene chloride (containing 5.1 g. of dihydropyran and 210 mg. of pyridine hydrochloride) is allowed to stand for 20 hr. at room temperature. The resulting solution is then washed with aqueous potassium bicarbonate, brine, dried over magnesium sulfate, and thereafter evaporated to yield the bis(tetrahydropyranyl) ether of the starting material (3.1 g.).

The lactone bis(tetrahydropyranyl)ether of the preceding paragraph (6.1 g.) is then dissolved in 120 ml. of toluene cooled to −73° C. Thereafter 50 ml. of a 10 percent solution of diisobutylaluminum hydride and toluene is slowly added at −68° C. The reaction mixture is stirred for 30 min. at −70° C. and then 36 ml. of a tetrahydrofuran water (2:1) mixtures is slowly added. The resulting mixture is allowed to warm to room temperature with continued stirring. Thereafter, the product is filtered and the filter cake washed with benzene. The combined filtrates are then washed with brine, dried over magnesium sulfate, and evaporated to yield the lactol bis-tetrahydropyranyl ether of the lactone starting material (7.3 g.).

C. A 57 percent dispersion of sodium hydride in mineral oil (1.75 g.) in 50 ml. of dimethyl sulfoxide is added to 4-carboxybutyltriphenylphosphonium bromide (9.2 g.) which maintaining the reaction mixture at 20° C. The reaction mixture is stirred for one hr. The reaction product of part B of this example (7.3 g.) in 20 ml. of dimethylsulfoxide is then added. The reaction mixture is then stirred for 4 hr. at room temperature and the mixture thereafter cooled to 10° C. Potassium sulfate (8 g.) 80 ml. of water is then added, maintaining the reaction temperature at 15° C. or less. The organic layer is then washed with water, brine, and thereafter dried over magnesium sulfate. The product is then evaporated to yield the yellow oil which is separated from residual starting material by chromatoraphing the crude product on 200 g. of silica gel packed in 20 percent ethyl acetate in Skellysolve B, eluting with 20-70 percent ethyl acetate in Skellysolve B. Fractions containing pure 15-epi-16,16-dimethyl-cis-13-PGF$_{2\alpha}$, 11,15-bis-tetrahydropyranyl ether are then combined. A solution of this free acid in acetonitrile is then prepared and reacted with methyl iodide and a diisopropylethylamine to yield 4.05 g. of 15-epi-16,16-dimethyl-cis-13-PGF$_{2\alpha}$, methyl ester, 11,15-bis-tetrahydropyranyl ether. NMR absorptions are observed at 0.88, 0.92, 3.68, 3.2–4.95, and 5.1–5.8 δ.

D. Preparation of 15-epi-16,16-dimethyl-cis-13-PGF$_{2\alpha}$, methyl ester.

A solution of 3.2 g. of crude reaction product of part C. of this example in a mixture of 70 ml. of tetrahydrofuran, 49 ml. of water, and 10.5 of 85 percent phosphoric acid is allowed to stand at 40° C. for 4 hr. The resulting mixture is then diluted with 100 ml. of brine and extracted with ethyl acetate. The combined extracts are then washed with 40 ml. of 20 percent sodium chloride and thereafter dried over magnesium sulfate. This product is then evaporated to yield a slightly yellow oil (3.0 g.) Upon silica gel chromatography, eluting with 50 percent acetone in methylene chloride 0.87 g. of impure product is obtained. Repeating the chromatography, eluting with 1 to 50 percent acetone in methylene chloride, there is obtained 0.71 g. of pure product. NMR absorptions are observed at 0.87, 0.90, 3.68, 3.5–5.0, and 5.1–6.1 δ. The mass spectrum for the trimethylsilyl derivative shows base peak absorption at 597.3868.

E. Preparation of 15-epi-16,16-dimethyl-cis-13-PGE$_2$, methyl ester. 30 of methylene chloride is then added rapidly. The resulting mixture 3,5-Dimethylpyrazole (5.26 g.) is added to a suspension of 5.5 g. of anhydrous chromium trioxide in 125 ml. of methylene chloride. This mixture is then stirred for 30 min., then cooled to 17° C., and a solution of the reaction product of part D of this example (3.9 g.) in 45 ml. of methylene is then slowly combined with 15 ml. of methylene chloride. After 30 min. this reaction mixture is then chromatographed on silica gel (packed in ethyl acetate and Skellysolve B: 1:1). Eluting with ethyl acetate and Skellysolve B (1:1) a crude PGE-type, 11,15-bis(tetrahydropyranyl)ether product (3.6 g.) is obtained as an oil.

The above oil is then dissolved in 200 ml. of a mixture of tetrahydrofuran, water, and acetic acid (1:3:6). This mixture is then allowed to stand for 4 hr. at 40° C. and thereafter diluted with 400 ml. of water and freeze dried. A diethyl ether solution of the freeze-dried residue is then prepared and washed with cold 0.1 N potassium bicarbonate and brine. The resulting mixture is then dried over magnesium sulfate and evaporated to yield crude 15-epi-16,16-dimethyl-cis-13-PGE$_2$, methyl ester (2.7 g.) as a thin yellow oil. Chromatographing on a silica gel column packed with acetone and methylene chloride (1:9) yields pure product can upon elution with acetone and methylene chloride (1:9). R$_f$ for silia gel TLC is 0.60 (acetone and methylene chloride; 1:2). NMR absorptions are observed at 0.84, 0.89, 3.66, and 5.05–6.2 δ. The mass spectrum shows base peak absorption for the trimethylsilyl derivative at 523.3286.

F. Preparation of 15-epi-16,16-dimethyl-cis-13-PGF$_{2\beta}$, methyl ester.

A solution of the reaction product of part E above (0.346 g.) in 20 ml. of methanol is cooled to −10° C. To this cooled mixture is then added sodium borohydride (80 mg.). The resulting mixture is then stirred for 40 min. at −10° to −20° C., and thereafter 2.5 ml. of an acetic acid water (1:1) mixture is added. The resulting mixture is then evaporated under reduced pressure and the residue shaken with ethyl acetate and water. The organic phase is then washed with aqueous sodium bicarbonate, saturated saline, dried over magnesium sulfate, and evaporated to yield an oil (3.48 g.). This oil is then chromatographed on 50 g. of silica gel packed in one percent methanol in methylene chloride. Eluting with one to 5 percent methanol in methylene chloride yields 0.16 g. of 15-epi-16,16-dimethyl-cis-13-PGF$_{2\beta}$, methyl ester. The mass spectrum shows base peak absorption at 597.3868. NMR absorptions are observed at 0.84, 0,88, 3.65, 3.1–4.3, and 5.1–6.1 δ.

G. Preparation of 15-epi-16,16-dimethyl-11-deoxy-cis-13-PGE$_2$, methyl ester.

A solution of the reaction product of part C of this example (1.30 g.) in 6 ml. of pyridine is cooled in an ice bath and thereafter one ml. of acetic acid is added. This resulting mixture is then allowed to stand for 24 hr. at −15° C., 24 hr. at +5° C., and thereafter 24 hr. at room temperature. Accordingly, there is formed initially the 11-acetate of a starting material, therefter the 11,15-diacetate of the starting material, and finally 15-epi-16,16-dimethyl-cis-13-PGA$_2$, methyl ester, 15-acetate. This reaction product is then cooled to 5° C. in methanol (6 ml.) is added. This resulting mixtue is then allowed to stand for 4 hr. at room temperature and thereafter evaporated at reduced pressure. A diethyl ether solution of the residue is then washed with aqueous potassium bisulfate, water, aqueous potassium bicarbonate, and saturated brine. This washed mixture is then dried over magnesium sulfate and evaporated to yield a colorless oil (1.45 g.). The oil is then chromatographed on silica gel eluting with 10–20 percent ethyl acetate in Skellysolve B to yield 1.34 g. of pure PGA-type methyl ester 15-acetate product. NMR absorptions are observed at 0.90, 0.92, 2.05, 3.65, 3.55–4.0, 5.1–5.8, 6.0–6.28, and 7.42–7.72 δ.

Sodium borohydride (0.4 g.) is then dissolved in 10 ml. of cold water, and thereafter diluted with 40 ml. of cold (−40° C.) methanol. The resulting solution is then added immediately to a cold (−12° C.) solution of the product of the preceding paragraph in 15 ml. of methanol. After about 20 min. at −20° C. to −10° C. the reaction mixture is then cooled to −30° C. and thereafter 3 ml. of acetic acid is added, maintaining the temperature of the acetic acid at less than −20° C. The resulting mixture is then allowed to warm to room temperature and thereafter diluted with water and extracted with methylene chloride. The organic extracts are then washed with aqueous potassium bicarbonate and brine and thereafter evaporated under reduced pressure. The residue thus obtained is dissolved in methylene chloride, dried over magnesium sulfate, and evaporated to yield a mixture of 9α-hydroxy and 9β-hydroxy compounds, e.g. 15-epi-16,16-dimethyl-11-deoxy-cis-13-PGF$_{2\alpha}$ and PGF$_{2\beta}$, methyl ester, 15-acetate. A solution of the above 9nmixture in 25 ml. of acetone is then cooled to −40° C. Thereafter the Jones reagent is added rapidly, maintaining the reaction mixture at −40 to −30° C. The resulting mixture is then stirred for 30 min. at −25° C. Thereafter isopropyl alcohol (2.5 ml.) is added and the mixture is stirred for an additional 30 min. at 25° C. The resulting mixture is then diluted with water and extracted with diethyl ether. Ethereal extracts are then washed with water, aqueous potassium bicarbonate, and brine, and thereafter dried over magnesium sulfate and evaporated to yield the colorless oil (1.31 g.). This oil is then chromatographed on 200 g. of silica gel packed in one percent acetone and methylene chloride, eluting with one to 4 percent acetone in methylene chloride. Accordingly, 0.488 g. of pure product is recovered. NMR absorptions are observed at 0.88, 0.90, 2.03, 3.65, and 5.1–5.85 δ. Accordingly, there is obtained 15-epi-16,16-dimethyl-cis-13-PGE$_2$, methyl ester, 15-acetate.

A solution of the reaction product of the preceding paragraph (0.45 g.) in 9 ml. of methanol is purged with nitrogen. Methanolic sodium methoxide (0.78 ml., containing 3.35 mmol. of sodium methoxide) is added. The resulting mixture is then allowed to stand for 30 min. Acetic acid is then added and the mixture is evaporated under reduced pressure, removing all volatile components. The residue is then shaken with ethyl acetate and water, and the organic extract washed with aqueous potassium bicarbonate, brine, and thereafter dried over magnesium sulfate and evaporated to yield the yellow oil (0.55 g.). This oil is then chromatographed on 60 g. of silica gel packed on one percent acetone and methylene chloride, eluting with one to 7 percent acetone in methylene chloride. Accordingly, 0.27 g. of title product is obtained as a colorless oil. NMR absorptions are observed 0.86, 0.91, 3.69, 4.0–4.3, and 5.15–5.95 δ.

EXAMPLE 27

15-epi-cis-13-PGA$_2$, methyl ester, 15-methyl ether.

A. A solution of 15-epi-cis-13-PGE$_2$, methyl ester, 15-methyl ether (0.503 gm) in 3 ml. of pyridine is cooled to 5° C. and thereafter 0.5 ml. of acetic anhydride is added. The resulting mixture is then allowed to stand at ambient temperature for 2 hours and thereafter cooled to 5° C. Thereupon 3 ml. of methanol is added and the mixture is then allowed to stand for 12 hours, warming to ambient temperature. The mixture is then evaporated under reduced pressure, yielding a yellow residue which is extracted with diethyl ether and thereafter washed with aqueous potassium bisulfate and brine, and then dried (magnesium sulphate) and evaporated to yield 0.460 gm. of a yellow oil. The oil is chromatographed on 50 gm. of silica gel, packed in 1 percent acetone in methylene chloride, eluting with 1–2 percent acetone in methylene chloride. Thereupon 0.403 gm. of pure title compound are obtained. NMR absorptions are observed at 3.31, 3.67, 3.4–4.8, 5.1–5.7, 6.1–6.35, and 7.45–7.68 δ.

Following the procedure of the above examples, and utilizing the appropriate starting material as described therein, there are prepared the cis-13-PGF$_\alpha$ -type compounds described in the tables below. For each of these compounds below, and for each of the various other cis-13-PG-type compounds described herein, there is present one of the C-15 epimers. When necessary to determine for any such compound which 15-epimer is present, methods known in the art for determination of absolute configuration about an assymetric carbon atom are employed.

Table A

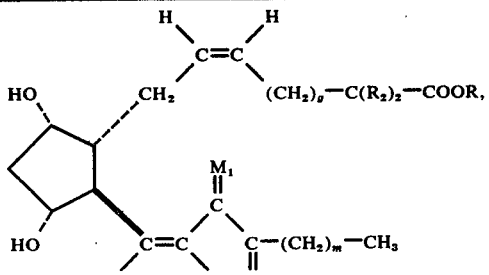

cis-13-PGF$_{2\alpha}$-type compounds

| Example | g | m | L$_1$ R$_3$ | R$_4$ | M$_1$ R$_5$ | R$_6$ | ~OR$_6$ | R$_1$ | R$_2$ | Name |
|---|---|---|---|---|---|---|---|---|---|---|
| A-1 | 2 | 3 | methyl | hydrogen | hydrogen | hydrogen | α | methyl | hydrogen | 15-epi-16-methyl, methyl ester |
| A-2 | 2 | 3 | methyl | hydrogen | methyl | hydrogen | α | methyl | hydrogen | 15-epi-15,16-dimethyl, methyl ester |
| A-3 | 2 | 3 | methyl | hydrogen | hydrogen | methyl | α | methyl | hydrogen | 15-epi, methyl ester, |
| A-4 | 2 | 3 | methyl | methyl | hydrogen | hydrogen | α | methyl | hydrogen | 15-epi-16,16-dimethyl, methyl ester |
| A-5 | 2 | 3 | methyl | methyl | methyl | hydrogen | α | methyl | hydrogen | 15-epi-15,16,16-trimethyl, methyl ester |
| A-6 | 2 | 3 | methyl | methyl | hydrogen | methyl | α | methyl | hydrogen | 15-epi-16,16-dimethyl, methyl ester, 15-methyl ether |
| A-7 | 2 | 3 | fluoro | hydrogen | hydrogen | hydrogen | α | methyl | hydrogen | 15-epi-16-fluoro, methyl ester |
| A-8 | 2 | 3 | fluoro | hydrogen | methyl | hydrogen | α | methyl | hydrogen | 15-epi-15-methyl-16-fluoro, methyl ester |
| A-9 | 2 | 3 | fluoro | hydrogen | hydrogen | methyl | α | methyl | hydrogen | 15-epi-16-fluoro, methyl ester, 15-methyl ether |
| A-10 | 2 | 3 | fluoro | fluoro | hydrogen | hydrogen | α | methyl | hydrogen | 15-epi-16,16-difluoro, methyl ester |
| A-11 | 2 | 3 | fluoro | fluoro | methyl | hydrogen | α | methyl | hydrogen | 15-epi-15-methyl-16,16-difluoro, methyl ester |
| A-12 | 2 | 3 | fluoro | fluoro | hydrogen | methyl | α | methyl | hydrogen | 15-epi-16,16-difluoro, methyl ester, 15-methyl ether |
| A-13 | 2 | 3 | hydrogen | hydrogen | hydrogen | hydrogen | α | methyl | hydrogen | 15-epi, methyl ester |
| A-14 | 2 | 3 | hydrogen | hydrogen | hydrogen | methyl | α | methyl | hydrogen | 15-epi, methyl ester, 15-methyl ether |
| A-15 | 2 | 3 | methyl | hydrogen | hydrogen | hydrogen | α | methyl | fluoro | 15-epi-2,2-difluoro-16-methyl, methyl ester |
| A-16 | 2 | 3 | methyl | hydrogen | methyl | hydrogen | α | methyl | fluoro | 15-epi-2,2-difluoro-15,16-dimethyl, methyl ester |
| A-17 | 2 | 3 | methyl | hydrogen | hydrogen | methyl | α | methyl | fluoro | 15-epi-2,2-difluoro, methyl ester, 15-methyl ether |
| A-18 | 2 | 3 | methyl | methyl | hydrogen | hydrogen | α | methyl | fluoro | 15-epi-2,2-diflfuoro-16,16-dimethyl, methyl ester |
| A-19 | 2 | 3 | methyl | methyl | methyl | hydrogen | α | methyl | fluoro | 15-epi-2,2-difluoro-15,16,16-trimethyl, methyl ester |
| A-20 | 2 | 3 | methyl | methyl | hydrogen | methyl | α | methyl | fluoro | 15-epi-2,2-difluoro-16,16-dimethyl, methyl ester, 15-methyl ether |
| A-21 | 2 | 3 | fluoro | hydrogen | hydrogen | hydrogen | α | methyl | fluoro | 15-epi-2,2,16-trifluoro, methyl ester |
| A-22 | 2 | 3 | fluoro | hydrogen | methyl | hydrogen | α | methyl | fluoro | 15-epi-2,2,16-trifluoro-15-methyl, methyl ester |
| A-23 | 2 | 3 | fluoro | hydrogen | hydrogen | methyl | α | methyl | fluoro | 15-epi-2,2,16-trifluoro, methyl ester, 15-methyl ether |
| A-24 | 2 | 3 | fluoro | fluoro | hydrogen | hydrogen | α | methyl | fluoro | 15-epi-2,2,16,16-tetrafluoro, methyl ester |
| A-25 | 2 | 3 | fluoro | fluoro | methyl | hydrogen | α | methyl | fluoro | 15-epi-2,2,16,16-tetrafluoro-15-methyl, methyl ester |
| A-26 | 2 | 3 | fluoro | fluoro | hydrogen | methyl | α | methyl | fluoro | 15-epi-2,2,16,16-tetrafluoro, methyl ester, 15-methyl ether |
| A-27 | 2 | 3 | hydrogen | hydrogen | hydrogen | hydrogen | α | methyl | fluoro | 15-epi-2,2-difluoro, methyl ester |
| A-28 | 2 | 3 | hydrogen | hydrogen | methyl | hydrogen | α | methyl | fluoro | 15-epi-2,2-difluoro-15-methyl, methyl ester |
| A-29 | 2 | 3 | hydrogen | hydrogen | hydrogen | methyl | α | methyl | fluoro | 15-epi-2,2-difluoro, methyl ester, 15-methyl ether |
| A-30 | 4 | 3 | hydrogen | hydrogen | hydrogen | hydrogen | α | methyl | hydrogen | 15-epi-2a,2b-dihomo, methyl ester |
| A-31 | 2 | 3 | methyl | methyl | hydrogen | hydrogen | α | methyl | hydrogen | 15-epi-2a,2b-dihomo-16,16-dimethyl, methyl ester |
| A-32 | 4 | 3 | methyl | methyl | methyl | hydrogen | α | methyl | hydrogen | 15-epi-2a,2b-dihomo-15,16,16-trimethyl, methyl ester |
| A-33 | 4 | 3 | fluoro | fluoro | hydrogen | hydrogen | α | methyl | hydrogen | 15-epi-2a,2b-dihomo-16,16-difluoro, methyl ester |
| A-34 | 4 | 3 | fluoro | fluoro | methyl | hydrogen | α | methyl | hydrogen | 15-epi-2a,2b-dihomo-15-methyl-16,16-difluoro, methyl ester |

Table B

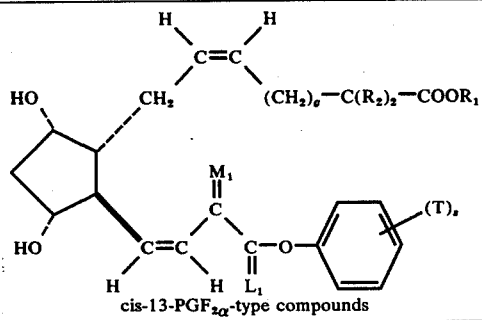

cis-13-PGF$_{2\alpha}$-type compounds

| Example | g | s | T | L$_1$ R$_3$ | R$_4$ | M$_1$ R$_5$ | R$_3$ | ~OR$_6$ | R$_3$ | R$_2$ | Name |
|---|---|---|---|---|---|---|---|---|---|---|---|
| B-1 | 2 | 0 | | hydrogen | hydrogen | hydrogen | hydrogen | α | methyl | hydrogen | 15-epi-16-phenoxy-17,18,19,20-tetranor, methyl ester |
| B-2 | 2 | 1 | p-fluoro | hydrogen | hydrogen | hydrogen | hydrogen | α | methyl | hydrogen | 16-(p-fluorophenoxy)-17,18,19,20-tetranor, methyl ester |
| B-3 | 2 | 1 | m-chloro | hydrogen | hydrogen | hydrogen | hydrogen | α | methyl | hydrogen | 16-(m-chlorophenoxy)-17,18,19,20-tetranor, methyl ester |
| B-4 | 2 | 1 | m-trifluoromethyl | hydrogen | hydrogen | hydrogen | hydrogen | α | methyl | hydrogen | 15-epi-16-(m-trifluoromethylphenoxy)-17,18,19,20-tetranor, methyl ester |
| B-5 | 2 | 0 | | hydrogen | hydrogen | methyl | hydrogen | α | methyl | hydrogen | 15-epi-15-methyl-16-phenoxy-17,18,19,20-tetranor, methyl ester |
| B-6 | 2 | 1 | p-fluoro | hydrogen | hydrogen | methyl | hydrogen | α | methyl | hydrogen | 15-epi-15-methyl-16-(p-fluorophenoxy)-17,18,19,20-tetranor, methyl ester |
| B-7 | 2 | 1 | m-chloro | hydrogen | hydrogen | methyl | hydrogen | α | methyl | hydrogen | 15-epi-15-methyl-16-(m-chlorophenoxy), methyl ester |
| B-8 | 2 | 1 | m-trifluoromethyl | hydrogen | hydrogen | methyl | hydrogen | α | methyl | hydrogen | 15-epi-15-methyl-16-(m-trifluoromethylphenoxy), methyl ester |
| B-9 | 2 | 0 | | hydrogen | hydrogen | hydrogen | methyl | α | methyl | hydrogen | 15-epi-16-phenoxy-17,18,19,20-tetranor, methyl ester, 15-methyl ether |
| B-10 | 2 | 1 | p-fluoro | hydrogen | hydrogen | hydrogen | methyl | α | methyl | hydrogen | 15-epi-16-(p-fluorophenoxy)-17,18,19,20-tetranor, methyl ester, 15-methyl ether |
| B-11 | 2 | 1 | m-chloro | hydrogen | hydrogen | hydrogen | methyl | α | methyl | hydrogen | 15-epi-16-(m-chlorophenoxy)-17,18,19,20-tetranor, methyl ester, 15-methyl ether |
| B-12 | 2 | 1 | m-trifluoromethyl | hydrogen | hydrogen | hydrogen | methyl | α | methyl | hydrogen | 15-epi-16-(m-trifluoromethylphenoxy)-17,18,19,20-tetranor, methyl ester, 15-methyl ether |
| B-13 | 2 | 0 | | methyl | methyl | hydrogen | hydrogen | α | methyl | hydrogen | 15-epi-16-methyl-16-phenoxy-18,19,20-trinor, methyl ester |
| B-14 | 2 | 1 | p-fluoro | methyl | methyl | hydrogen | hydrogen | α | methyl | hydrogen | 15-epi-16-methyl-16-(p-fluorophenoxy)-18,19,20-trinor, methyl ester |
| B-15 | 2 | 1 | m-chloro | methyl | methyl | hydrogen | hydrogen | α | methyl | hydrogen | 15-epi-16-methyl-16-(m-chlorophenoxy)-18,19,20-trinor, methyl ester |
| B-16 | 2 | 1 | m-trifluoromethyl | methyl | methyl | hydrogen | hydrogen | α | methyl | hydrogen | 15-epi-16-methyl-16-(m-trifluoromethylphenoxy)-18,19,20-trinor, methyl ester |
| B-17 | 2 | 0 | | methyl | methyl | methyl | hydrogen | α | methyl | hydrogen | 15-epi-15,16-dimethyl-16-phenoxy-18,19,20-trinor, methyl ester |
| B-18 | 2 | 1 | p-fluoro | methyl | methyl | methyl | hydrogen | α | methyl | hydrogen | 15-epi-15,16-dimethyl-16-(p-fluorophenoxy)-ester |
| B-19 | 2 | 1 | m-chloro | methyl | methyl | methyl | hydrogen | α | methyl | hydrogen | 15-epi-15,16-dimethyl-16-(m-chlorophenoxy)-18,19,20-trinor, methyl ester |
| B-20 | 2 | 1 | m-trifluoromethyl | methyl | methyl | methyl | hydrogen | α | methyl | hydrogen | 15-epi-15,16-dimethyl-16-(m-trifluoromethylphenoxy)-18,19,20-triphenoxy)-18,19,20-trinor, methyl ester |
| B-21 | 2 | 0 | | methyl | methyl | hydrogen | methyl | α | methyl | hydrogen | 15-epi-16-methyl-16- |

Table B-continued

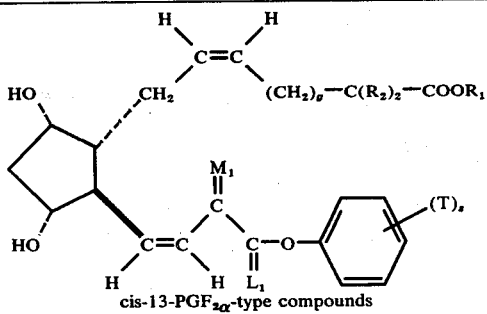

cis-13-PGF$_{2\alpha}$-type compounds

| Example | g | s | T | L$_1$ R$_3$ | R$_4$ | M$_1$ R$_5$ | R$_3$ | ~OR$_6$ | R$_3$ | R$_2$ | Name |
|---|---|---|---|---|---|---|---|---|---|---|---|
| | | | | | | gen | | | | gen | phenoxy-18,19,20-trinor, methyl ester, 15-methyl ether |
| B-22 | 2 | 1 | p-fluoro | methyl | methyl | hydro-gen | methyl | α | methyl | hydro-gen | 15-epi-16-methyl-16-(p-fluorophenoxy)-18,19,20-trinor, methyl ester, 15-methyl ether |
| B-23 | 2 | 1 | m-chloro | methyl | methyl | hydro-gen | methyl | α | methyl | hydro-gen | 15-epi-16-methyl-16-(m-chlorophenoxy)-18,19,20-trinor, methyl ester, 15-methyl ether |
| B-24 | 2 | 1 | m-trifluoromethyl | methyl | methyl | hydro-gen | methyl | α | methyl | hydro-gen | 15-epi-16-methyl-16-(m-trifluoromethylphenoxy)-18,19,20-trinor, methyl ester, 15-methyl ether |
| B-25 | 2 | 0 | | hydro-gen | hydro-gen | hydro-gen | hydro-gen | α | methyl | fluoro | 15-epi-2,2-difluoro-16-phenoxy-17,18,19,20-tetranor, methyl ester |
| B-26 | 2 | 1 | p-fluoro | hydro-gen | hydro-gen | hydro-gen | hydro-gen | α | methyl | fluoro | 15-epi-2,2-difluoro-16-(p-fluorophenoxy)-17,18,19,20-tetranor, methyl ester |
| B-27 | 2 | 1 | m-chloro | hydro-gen | hydro-gen | hydro-gen | hydro-gen | α | methyl | fluoro | 15-epi-2,2-difluoro-16-(m-chlorophenoxy)-17,18,19,20-tetranor, methyl ester |
| B-28 | 2 | 1 | m-trifluoromethyl | hydro-gen | hydro-gen | hydro-gen | hydro-gen | α | methyl | fluoro | 15-epi-2,2-difluoro-16-(m-trifluoromethylphenoxy)-17,18,19,20-tetranor, methyl ester |
| B-29 | 2 | 0 | | hydro-gen | hydro-gen | methyl | hydro-gen | α | methyl | fluoro | 15-epi-2,2-difluoro-15-methyl-16-phenoxy-17,18,19,20-tetranor, methyl ester |
| B-30 | 2 | 1 | p-fluoro | hydro-gen | hydro-gen | methyl | hydro-gen | α | methyl | fluoro | 15-epi-2,2-difluoro-15-methyl-16-(p-fluorophenoxy)-17,18,19,20-tetranor, methyl ester |
| B-31 | 2 | 1 | m-chloro | hydro-gen | hydro-gen | methyl | hydro-gen | α | methyl | fluoro | 15-epi-2,2-difluoro-15-methyl-16-(m-chlorophenoxy), methyl ester |
| B-32 | 2 | 1 | m-trifluoromethyl | hydro-gen | hydro-gen | methyl | hydro-gen | α | methyl | fluoro | 15-epi-2,2-difluoro-15-methyl-16-(m-trifluoromethylphenoxy), methyl ester |
| B-33 | 2 | 0 | | hydro-gen | hydro-gen | hydro-gen | methyl | α | methyl | fluoro | 15-epi-2,2-difluoro-16-phenoxy-17,18,19,20-tetranor, methyl ester, 15-methyl ether |
| B-34 | 2 | 1 | p-fluoro | hydro-gen | hydro-gen | hydro-gen | methyl | α | methyl | fluoro | 15-epi-2,2-difluoro-16-(p-fluorophenoxy)-17,18,19,20-tetranor, methyl ester, 15-methyl ether |
| B-35 | 2 | | m-chloro | hydro-gen | hydro-gen | hydro-gen | methyl | α | methyl | fluoro | 15-epi-2,2-difluoro-16-(m-chlorophenoxy)-17,18,19,20-tetranor, methyl ester, 15-methyl ether |
| B-36 | 2 | 1 | m-trifluoromethyl | hydro-gen | hydro-gen | hydro-gen | methyl | α | methyl | fluoro | 15-epi-2,2-difluoro-16-(m-trifluoromethylphenoxy)-17,18,19,20-tetranor, methyl ester, 15-methyl ether |
| B-37 | 2 | 0 | | methyl | methyl | hydro-gen | hydro-gen | α | methyl | fluoro | 15-epi-2,2-difluoro-16-methyl-16-phenoxy-18,19,20-trinor, methyl ester |
| B-38 | 2 | 1 | p-fluoro | methyl | methyl | hydro-gen | hydro-gen | α | methyl | fluoro | 15-epi-2,2-difluoro-16-methyl-16-(p-fluorophenoxy)-18,19,20-trinor, methyl ester |
| B-39 | 2 | 1 | m- | methyl | methyl | hydro-gen | hydro-gen | α | methyl | fluoro | 15-epi-2,2-difluoro-16- |

Table B-continued

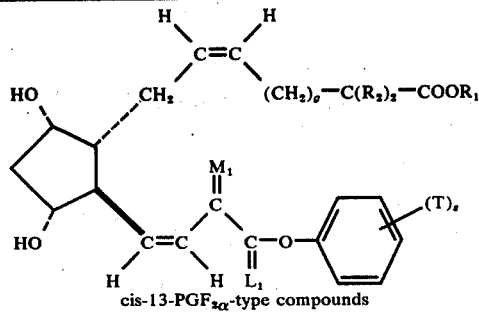
cis-13-PGF$_{2\alpha}$-type compounds

| Example | g | s | T | L$_1$ R$_3$ | R$_4$ | R$_5$ | M$_1$ R$_3$ | ~OR$_6$ | R$_3$ | R$_2$ | Name |
|---|---|---|---|---|---|---|---|---|---|---|---|
|  |  |  | chloro |  |  | gen | gen |  |  |  | (m-chlorophenoxy)-18,19,20-trinor, methyl ester |
| B-40 | 2 | 1 | m-tri-fluoromethyl | methyl | methyl | hydrogen | hydrogen | α | methyl | fluoro | 15-epi-2,2-difluoro-16-methyl-16-(m-trifluoromethylphenoxy)-18,19,20-trinor, methyl ester |
| B-41 | 2 | 0 |  | methyl | methyl | methyl | hydrogen | α | methyl | fluoro | 15-epi-2,2-difluoro-15,16-dimethyl-16-phenoxy 18,19,20-trinor, methyl ester |
| B-42 | 2 | 1 | p-fluoro | methyl | methyl | methyl | hydrogen | α | methyl | fluoro | 15-epi-2,2-difluoro-15,16-dimethyl-16-(p fluorophenoxy)-18,19,20-trinor, methyl |
| B-43 | 2 | 1 | m-chloro | methyl | methyl | methyl |  | α | methyl | fluoro | 15-epi-2,2-difluoro-15,16-dimethyl-16-(m-chlorophenoxy)-18,19,20-trinor, methyl ester |
| B-44 | 2 | 1 | m-tri-fluoromethyl | methyl | methyl | methyl | hydrogen | α | methyl | fluoro | 15-epi-2,2-difluoro-15,16-dimethyl-16-(m-trifluoromethylphenoxy)-18,19,20-trinor, methyl ester |
| B-45 | 2 | 0 |  | methyl | methyl | hydrogen | methyl | α | methyl | fluoro | 15-epi-2,2-difluoro-16-methyl-16-phenoxy-18,19,20-trinor, methyl ester, 15-methyl ether |
| B-46 | 2 | 1 | p-fluoro | methyl | methyl | hydrogen | methyl | α | methyl | fluoro | 15-epi-2,2-difluoro-16-methyl-16-(p-fluorophenoxy)-18,19,20-trinor, methyl ester, 15-methyl ether |
| B-47 | 2 | 1 | m-chloro | methyl | methyl | hydrogen | methyl | α | methyl | fluoro | 15-epi-2,2-difluoro-16-methyl-16-(m-chlorophenoxy)-18,19,20-trinor, methyl ester, 15-methyl ether |
| B-48 | 2 | 1 | m-tri-fluoromethyl | methyl | methyl | hydrogen | methyl | α | methyl | fluoro | 15-epi-2,2-difluoro-16-methyl-16-(m-trifluoromethylphenoxy)-18,19,20-methyl ester, 15-methyl ether |
| B-49 | 4 | 0 |  | hydrogen | hydrogen | hydrogen | hydrogen | α | methyl | hydrogen | 15,epi-2a,2b-dihomo-16-phenoxy-17,18,19,20-tetranor, methyl ester |
| B-50 | 4 | 1 | p-fluoro | hydrogen | hydrogen | hydrogen | hydrogen | α | methyl | hydrogen | 15-epi-2a,2b-dihomo-16-(p-fluorophenoxy)-17,18,19,20-tetranor, methyl ester |
| B-51 | 4 | 1 | m-chloro | hydrogen | hydrogen | hydrogen | hydrogen | α | methyl | hydrogen | 15-epi-2a,2b-dihomo-16-(m-chlorophenoxy)-17,18,19,20-tetranor, methyl ester |
| B-52 | 4 | 1 | m-tri-fluoromethyl | hydrogen | hydrogen | hydrogen | hydrogen | α | methyl | hydrogen | 15-epi-2a,2b-dihomo-16-(m-trifluoromethylphenoxy)-17,18,19,20-tetranor, methyl ester |
| B-53 | 4 | 0 |  | hydrogen | hydrogen | methyl | hydrogen | α | methyl | hydrogen | 15-epi-2a,2b-dihomo-15-methyl-16-phenoxy-17,18,19,20-tetranor, methyl ester |
| B-54 | 4 | 1 | p-fluoro | hydrogen | hydrogen | methyl | hydrogen | α | methyl | hydrogen | 15-epi-2a,2b-dihomo-15-methyl-16-(p-fluorophenoxy)-17,18,19,20-tetranor, methyl ester |
| B-55 | 4 | 1 | m-chloro | hydrogen | hydrogen | methyl | hydrogen | α | methyl | hydrogen | 15-epi-2a,2b-dihomo-15-methyl-16-(m-chlorophenoxy)-17,18,19,20-tetranor, methyl ester |
| B-56 | 4 | 1 | m-tri-fluoromethyl | hydrogen | hydrogen | methyl | hydrogen | α | methyl | hydrogen | 15-epi-2a,2b-dihomo-15-methyl-16-(m-trifluoromethylphenoxy)- |

Table B-continued

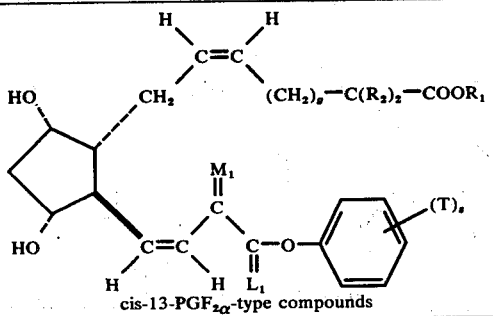

cis-13-PGF$_{2\alpha}$-type compounds

| Example | g | s | T | L$_1$ R$_3$ | R$_4$ | R$_5$ | M$_1$ R$_3$ | ~OR$_6$ | R$_3$ | R$_2$ | Name |
|---|---|---|---|---|---|---|---|---|---|---|---|
| | | | | | | | | | | | 17,18,19,20-tetranor, methyl ester |

Table C

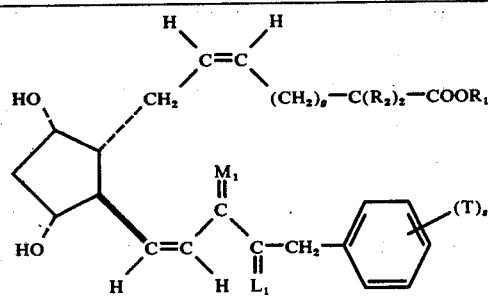

cis-13-18,19,20-trinor-PGF$_{2\alpha}$-type compounds

| Example | g | s | T | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|---|---|
| C-1 | 2 | 0 | | hydrogen | hydrogen | hydrogen | hydrogen | α | methyl | hydrogen | 15-epi-17-phenyl, methyl ester |
| C-2 | 2 | 1 | p-fluoro | hydrogen | hydrogen | hydrogen | hydrogen | α | methyl | hydrogen | 15-epi-17-(p-fluorophenyl), methyl ester |
| C-3 | 2 | 1 | m-chloro | hydrogen | hydrogen | hydrogen | hydrogen | α | methyl | hydrogen | 15-epi-17-(m-chlorophenyl), methyl ester |
| C-4 | 2 | 1 | m-trifluoromethyl | hydrogen | hydrogen | hydrogen | hydrogen | α | methyl | hydrogen | 15-epi-17-(m-trifluoromethylphenyl), methyl ester |
| C-5 | 2 | 0 | | hydrogen | hydrogen | methyl | hydrogen | α | methyl | hydrogen | 15-epi-15-methyl-17-phenyl, methyl ester |
| C-6 | 2 | 1 | p-fluoro | hydrogen | hydrogen | methyl | hydrogen | α | methyl | hydrogen | 15-epi-15-methyl-17-(p-fluorophenyl), methyl ester |
| C-7 | 2 | 1 | m-chloro | hydrogen | hydrogen | methyl | hydrogen | α | methyl | hydrogen | 15-epi-15-methyl-17-(m-chlorophenyl), methyl ester |
| C-8 | 2 | 1 | m-trifluoromethyl | hydrogen | hydrogen | methyl | hydrogen | α | methyl | hydrogen | 15-epi-15-methyl-17-(m-trifluoromethylphenyl), methyl ester |
| C-9 | 2 | 0 | | hydrogen | hydrogen | hydrogen | methyl | α | methyl | hydrogen | 15-epi-17-phenyl, methyl ester, 15-methyl ether |
| C-10 | 2 | 1 | p-fluoro | hydrogen | hydrogen | hydrogen | methyl | α | methyl | hydrogen | 15-epi-17-(p-fluorophenyl), methyl ester, 15-methyl ether |
| C-11 | 2 | 1 | m-chloro | hydrogen | hydrogen | hydrogen | methyl | α | methyl | hydrogen | 15-epi-17-(m-chlorophenyl), methyl ester, 15-methyl ether |
| C-10 | 2 | 1 | p-fluoro | hydrogen | hydrogen | hydrogen | methyl | α | methyl | hydrogen | 15-epi-17-(p-fluorophenyl), methyl ester, 15-methyl ether |
| C-11 | 2 | 1 | m-chloro | hydrogen | hydrogen | hydrogen | methyl | α | methyl | hydrogen | 15-epi-17-(m-chlorophenyl), methyl ester, 15-methyl ether |
| C-12 | 2 | 1 | m-trifluoromethyl | hydrogen | hydrogen | hydrogen | methyl | α | methyl | hydrogen | 15-epi-17-(m-trifluoromethylphenyl), methyl ester, 15-methyl ether |
| C-13 | 2 | 0 | | methyl | methyl | hydrogen | hydrogen | α | methyl | hydrogen | 15-epi-16,16-dimethyl-17-phenyl, methyl ester |
| C-14 | 2 | 1 | p-fluoro | methyl | methyl | hydrogen | hydrogen | α | methyl | hydrogen | 15-epi-16,16-dimethyl-17-(p-fluorophenyl), methyl ester |
| C-15 | 2 | 1 | m-chloro | methyl | methyl | hydrogen | hydrogen | α | methyl | hydrogen | 15-epi-16,16-dimethyl-17-(m-chlorophenyl), methyl ester |
| C-16 | 2 | 1 | m-tri- | methyl | methyl | hydrogen | hydrogen | α | methyl | hydrogen | 15-epi-16,16-dimethyl- |

Table C-continued

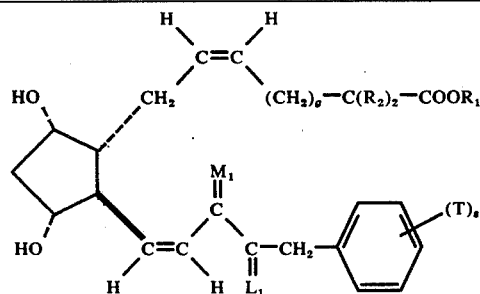

cis-13-18,19,20-trinor-PGF$_{2\alpha}$-type compounds

| Example | g | s | T | L$_1$ R$_3$ | R$_4$ | R$_5$ | M$_1$ R$_6$ | ~OR$_4$ | R$_1$ | R$_2$ | Name |
|---|---|---|---|---|---|---|---|---|---|---|---|
|  |  |  | fluoro methyl |  |  | gen | gen |  |  | gen | 17-(m-trifluoromethyl-phenyl), methyl ester |
| C-17 | 2 | 0 |  | methyl | methyl | methyl | hydro-gen | α | methyl | hydro-gen | 15-epi-15,16,16-tri-methyl-17-phenyl, methyl ester |
| C-18 | 2 | 1 | p-fluoro | methyl | methyl | methyl | hydro-gen | α | methyl | hydro-gen | 15-epi-15,16,16-tri-methyl-17-(p-fluoro-phenyl), methyl ester |
| C-19 | 2 | 1 | m-chloro | methyl | methyl | methyl | hydro-gen | α | methyl | hydro-gen | 15-epi-15,16,16-tri-methyl-17-(m-chloro-phenyl), methyl ester |
| C-20 | 2 | 1 | m-tri-fluoro | methyl | methyl | methyl | hydro-gen | α | methyl | hydro-gen | 15-epi-15,16,17-tri-methyl-(m-trifluoro-methylphenyl), methyl ester |
| C-21 | 2 | 0 |  | methyl | methyl | hydro-gen | methyl | α | methyl | hydro-gen | 15-epi-16,16-dimethyl-17-phenyl, methyl ester, 15-methyl ether |
| C-22 | 2 | 1 | p-fluoro | methyl | methyl | hydro-gen | methyl | α | methyl | hydro-gen | 15-epi-16,16-dimethyl-17-(p-fluorophenyl), methyl ester, 15-methyl ether |
| C-23 | 2 | 1 | m-chloro | methyl | methyl | hydro-gen | methyl | α | methyl | hydro-gen | 15-epi-16,16-dimethyl-17-(m-chlorophenyl), methyl ester, 15-methyl ether |
| C-24 | 2 | 1 | m-tri-fluoro methyl | methyl | methyl | hydro-gen | methyl | α | methyl | hydro-gen | 15-epi-16,16-dimethyl-17-(m-trifluoromethyl-phenyl), methyl ester, 15-methyl ether |
| C-25 | 2 | 0 |  | hydro-gen | hydro-gen | hydro-gen | hydro-gen | α | methyl | fluoro | 15-epi-2,2-difluoro-17-phenyl, methyl ester |
| C-26 | 2 | 1 | p-fluoro | hydro-gen | hydro-gen | hydro-gen | hydro-gen | α | methyl | fluoro | 15-epi-2,2-difluoro-17-(p-fluorophenyl), methyl ester |
| C-27 | 2 | 1 | m-chloro | hydro-gen | hydro-gen | hydro-gen | hydro-gen | α | methyl | fluoro | 15-epi-2,2-difluoro-17-(m-chlorophenyl), methyl ester |
| C-28 | 2 | 1 | m-tri-fluoro | hydro-gen | hydro-gen | hydro-gen | hydro-gen | α | methyl | fluoro | 15-epi-2,2-difluoro-17-(m-trifluoromethylphen-yl), methyl ester |
| C-29 | 2 | 0 |  | hydro-gen | hydro-gen | methyl | hydro-gen | α | methyl | fluoro | 15-epi-2,2-difluoro-15-methyl-17-phenyl, methyl ester |
| C-30 | 2 | 1 | p-fluoro | hydro gen | hydro-gen | methyl | hydro-gen | α | methyl | fluoro | 15-epi-2,2-difluoro-15-methyl-17-(p-fluorophen-yl), methyl ester |
| C-31 | 2 | 1 | m-chloro | hydro-gen | hydro-gen | methyl | hydro-gen | α | methyl | fluoro | 15-epi-2,2-difluoro-15-methyl-17-(m-chlorophen-yl), methyl ester |
| C-32 | 2 | 1 | m-tri-fluoro methyl | hydro-gen | hydro-gen | methyl | hydro-gen | α | methyl | fluoro | 15-epi-2,2-difluoro-15-methyl-17-(m-trifluoro-methylphenyl), methyl ester |
| C-33 | 2 | 0 |  | hydro-gen | hydro-gen | hydro-gen | methyl | α | methyl | fluoro | 15-epi-2,2-difluoro-17-phenyl, methyl ester, 15-methyl ether |
| C-34 | 2 | 1 | p-fluoro | hydro-gen | hydro-gen | hydro-gen | methyl | α | methyl | fluoro | 15-epi-2,2-difluoro-17-(p-fluorophenyl), methyl ester, 15-methyl ether |
| C-35 | 2 | 1 | m-chloro | hydro-gen | hydro-gen | hydro-gen | methyl | α | methyl | fluoro | 15-epi-2,2-difluoro-17-(m-chlorophenyl), methyl ester, 15-methyl ether |
| C-36 | 2 | 1 | m-tri-fluoro methyl | hydro-gen | hydro-gen | hydro-gen | methyl | α | methyl | fluoro | 15-epi-2,2-difluoro-17-(m-trifluoromethylphen-yl), methyl ester, 15-methyl ether |
| C-37 | 2 | 0 |  | methyl | methyl | hydro-gen | hydro-gen | α | methyl | fluoro | 15-epi-2,2-difluoro-16,16-dimethyl-17-phen-yl, methyl ester |
| C-38 | 2 | 1 | p-fluoro | methyl | methyl | hydro-gen | hydro-gen | α | methyl | fluoro | 15-epi-2,2-difluoro-16,16-dimethyl-17-(p- |

Table C-continued

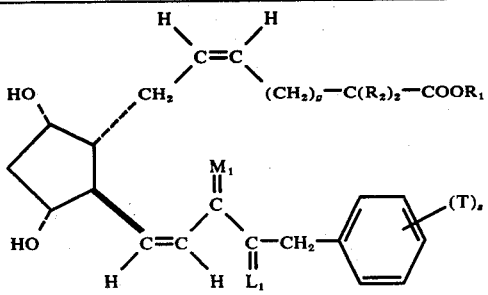

cis-13-18,19,20-trinor-PGF$_{2\alpha}$-type compounds

| Example | g | s | T | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|---|---|
| C-39 | 2 | 1 | m-chloro | methyl | methyl | hydrogen | hydrogen | α | methyl | fluoro | 15-epi-2,2-difluoro 16,16-dimethyl-17-(m-chlorophenyl), methyl ester |
| C-40 | 2 | 1 | m-trifluoromethyl | methyl | methyl | hydrogen | hydrogen | α | methyl | fluoro | 15-epi-2,2-difluoro-16,16-dimethyl-17-(m-trifluoromethylphenyl), methyl ester |
| C-41 | 2 | 0 | | methyl | methyl | methyl | hydrogen | α | methyl | fluoro | 15-epi-2,2-difluoro-15,16,16-trimethyl-17-phenyl, methyl ester |
| C-42 | 2 | 1 | p-fluoro | methyl | methyl | methyl | hydrogen | α | methyl | fluoro | 15-epi-2,2-difluoro-15,16,16-trimethyl-17-(p-fluorophenyl), methyl ester |
| C-43 | 2 | 1 | m-chloro | methyl | methyl | methyl | hydrogen | α | methyl | fluoro | 15-epi-2,2-difluoro-15,16,16-trimethyl-17-(m-chlorophenyl), methyl ester |
| C-44 | 2 | 1 | m-trifluoro | methyl | methyl | methyl | hydrogen | α | methyl | fluoro | 15-epi-2,2-difluoro-15,16,16-trimethyl-17-(m-trifluoromethylphenyl), methyl ester |
| C-45 | 2 | 0 | | methyl | methyl | hydrogen | methyl | α | methyl | fluoro | 15-epi-2,2-difluoro-16,16-dimethyl-17-phenyl, methyl ester, 15-methyl ether |
| C-46 | 2 | 1 | p-fluoro | methyl | methyl | hydrogen | methyl | α | methyl | fluoro | 15-epi-2,2-difluoro-16,16-dimethyl-17-(p-fluorophenyl), methyl ester, 15-methyl ether |
| C-47 | 2 | 1 | m-chloro | methyl | methyl | hydrogen | methyl | α | methyl | fluoro | 15-epi-2,2-difluoro-16,16-dimethyl-17-17-(m-chlorophenyl), methyl ester, 15-methyl ether |
| C-48 | 2 | 1 | m-trifluoro | methyl | methyl | hydrogen | methyl | α | methyl | fluoro | 15-epi-2,2-difluoro-16,16-dimethyl-17-(m-trifluoromethylphenyl), methyl ester, 15-methyl ether |
| C-49 | 4 | 0 | | hydrogen | hydrogen | hydrogen | hydrogen | α | methyl | hydrogen | 15-epi-2a,2b-dihomo-17-phenyl, methyl ester |
| C-50 | 4 | 1 | p-fluoro | hydrogen | hydrogen | hydrogen | hydrogen | α | methyl | hydrogen | 15-epi-2a,2b-dihomo-17-(p-fluorophenyl), methyl ester |
| C-51 | 4 | 1 | m-chloro | hydrogen | hydrogen | hydrogen | hydrogen | α | methyl | hydrogen | 15-epi-2a,2b-dihomo-17-(m-chlorophenyl), methyl ester |
| C-52 | 4 | 1 | m-trifluoromethyl | hydrogen | hydrogen | hydrogen | hydrogen | α | methyl | hydrogen | 15-epi-2a,2b-dihomo-17-(m-trifluoromethylphenyl), methyl ester |
| C-53 | 4 | 0 | | hydrogen | hydrogen | methyl | hydrogen | α | methyl | hydrogen | 15-epi-2a,2b-dihomo-15-methyl-17-phenyl, methyl ester |
| C-54 | 4 | 1 | p-fluoro | hydrogen | hydrogen | methyl | hydrogen | α | methyl | hydrogen | 15-epi-2a,2b-dihomo-15-methyl-17-(p-fluorophenyl), methyl ester |
| C-55 | 4 | 0 | m-chloro | hydrogen | hydrogen | methyl | hydrogen | α | methyl | hydrogen | 15-epi-2a,2b-dihomo-15-methyl-17-(m-chlorophenyl), methyl ester |
| C-56 | 4 | 1 | m-trifluoromethyl | hydrogen | hydrogen | methyl | hydrogen | α | methyl | hydrogen | 15-epi-2a,2b-dihomo-15-methyl-17-(m-trifluoromethylphenyl), methyl ester |
| C-57 | 2 | 0 | | fluoro | fluoro | hydrogen | hydrogen | α | methyl | hydrogen | 15-epi-16,16-difluoro-17-phenyl, methyl ester |
| C-58 | 3 | 1 | p-fluoro | fluoro | fluoro | hydrogen | hydrogen | α | methyl | hydrogen | 15-epi-16,16-difluoro-17-(p-fluorophenyl), methyl ester |

Table C-continued

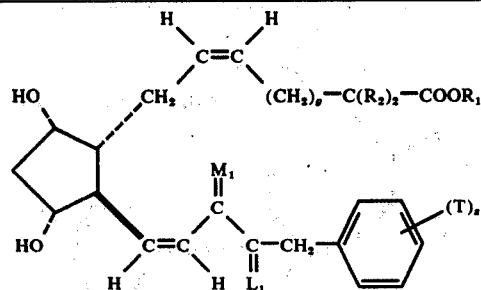

cis-13-18,19,20-trinor-PGF$_{2\alpha}$-type compounds

| Example | g | s | T | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|---|---|
| C-59 | 3 | 1 | m-chloro | fluoro | fluoro | hydrogen | hydrogen | α | methyl | hydrogen | 15-epi-16,16-difluoro-17-(m-chlorophenyl), methyl ester |
| C-60 | 2 | 1 | m-trifluoromethyl | fluoro | fluoro | hydrogen | hydrogen | α | methyl | hydrogen | 15-epi-16,16-difluoro-17-(m-trifluoromethylphenyl), methyl ester |
| C-61 | 2 | 0 |  | fluoro | fluoro | methyl | hydrogen | α | methyl | hydrogen | 15-epi-15-methyl-16,16-difluoro-17-phenyl, methyl ester |
| C-62 | 2 | 1 | p-fluoro | fluoro | fluoro | methyl | hydrogen | α | methyl | hydrogen | 15-epi-15-methyl-16,16-difluoro-17-(p-fluorophenyl), methyl ester |
| C-63 | 2 | 1 | m-chloro | fluoro | fluoro | methyl | hydrogen | α | methyl | hydrogen | 15-epi-15-methyl-16,16-difluoro-17-(m-chlorophenyl), methyl ester |
| C-64 | 2 | 1 | m-trifluoromethyl | fluoro | fluoro | methyl | hydrogen | α | methyl | hydrogen | 15-epi-15-methyl-16,16-difluoro-17-(m-trifluoromethylphenyl), methyl ester |
| C-65 | 2 | 0 |  | fluoro | fluoro | hydrogen | methyl | α | methyl | hydrogen | 15-epi-16,16-difluoro-17-phenyl, methyl ester, 15-methyl ether |
| C-66 | 2 | 1 | p-fluoro | fluoro | fluoro | hydrogen | methyl | α | methyl | hydrogen | 15-epi-16,16-difluoro-17-(p-fluorophenyl), methyl ester, 15-methyl ether |
| C-67 | 2 | 1 | m-chloro | fluoro | fluoro | hydrogen | methyl | α | methyl | hydrogen | 15-epi-16,16-difluoro-17-(m-chlorophenyl), methyl ester, 15-methyl ether |
| C-68 | 2 | 1 | m-trifluoromethyl | fluoro | fluoro | hydrogen | methyl | α | methyl | hydrogen | 15-epi-16,16-difluoro-17-(m-trifluoromethylphenyl), methyl ester 15-methyl ether |
| C-69 | 2 | 0 |  | fluoro | fluoro | hydrogen | hydrogen | α | methyl | fluoro | 15-epi-2,2,16,16-tetrafluoro-16-phenoxy, methyl ester |
| C-70 | 2 | 1 | p-fluoro | fluoro | fluoro | hydrogen | hydrogen | α | methyl | fluoro | 15-epi-2,2,16,16-tetrafluoro-16-(p-fluorophenyl), methyl ester |
| C-71 | 2 | 1 | m-chloro | fluoro | fluoro | hydrogen | hydrogen | α | methyl | fluoro | 15-epi-2,2,16,16-tetrafluoro-16-(m-chlorophenyl, methyl ester |
| C-72 | 2 | 1 | m-trifluoromethyl | fluoro | fluoro | hydrogen | hydrogen | α | methyl | fluoro | 15-epi-2,2,16,16-tetrafluoro-17-(m-trifluoromethylphenyl), methyl ester |
| C-73 | 2 | 0 |  | fluoro | fluoro | methyl | hydrogen | α | methyl | fluoro | 15-epi-2,2,16,16-tetrafluoro-15-methyl-17-phenyl, methyl ester |
| C-74 | 2 | 1 | p-fluoro | fluoro | fluoro | methyl | hydrogen | α | methyl | fluoro | 15-epi-2,2,16,16-tetrafluoro-15-methyl-17-(p-fluorophenyl), methyl ester |
| C-75 | 2 | 1 | m-chloro | fluoro | fluoro | methyl | hydrogen | α | methyl | fluoro | 15-epi-2,2,16,16-tetrafluoro-15-methyl-17-(m-chlorophenyl), methyl ester |
| C-76 | 2 | 1 | m-trifluoromethyl | fluoro | fluoro | methyl | hydrogen | α | methyl | fluoro | 15-epi-2,2,16,16-tetrafluoro-15-methyl-17-(m-trifluoromethylphenyl), methyl ester |
| C-77 | 2 | 0 |  | fluoro | fluoro | hydrogen | methyl | α | methyl | fluoro | 15-epi-2,2,16,16-tetrafluoro-7-phenyl, methyl ester, 15-methyl ether |
| C-78 | 2 | 1 | p-fluoro | fluoro | fluoro | hydrogen | methyl | α | methyl | fluoro | 15-epi-2,2,16,16-tetrafluoro-17-(p-fluorophenyl),methyl ether, 15-methyl ester |
| C-79 | 2 | 1 | m-chloro | fluoro | fluoro | hydrogen | methyl | α | methyl | fluoro | 15-epi-2,2,16,16-tetrafluoro-17-(m-chlorophenyl), methyl ester, |

Table C-continued

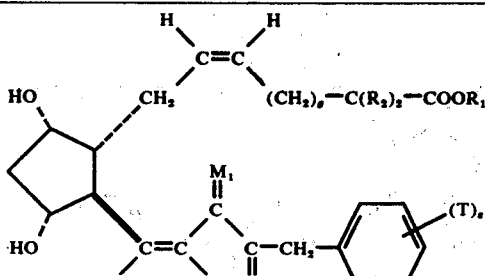

cis-13-18,19,20-trinor-PGF$_{2\alpha}$-type compounds

| Example | g | s | T | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|---|---|
| C-80 | 2 | 1 | m-tri-fluoro | fluoro | fluoro | hydrogen | methyl | α | methyl | fluoro | 15-methyl ether 15-epi-2,2,16,16-tetrafluoro-16-(m-trifluoromethyl), methyl ester, 15-methyl ether |

Table D

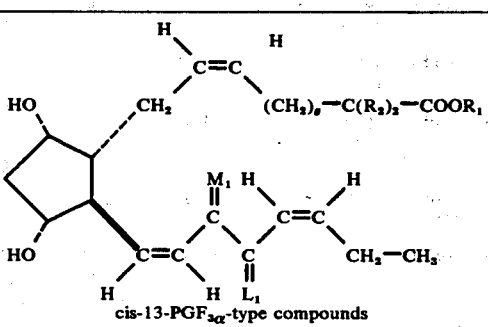

cis-13-PGF$_{3\alpha}$-type compounds

| Example | g | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|
| D-1 | 2 | methyl | hydrogen | hydrogen | hydrogen | α | methyl | hydrogen | 15-epi-16-methyl, methyl ester |
| D-2 | 2 | methyl | hydrogen | methyl | hydrogen | α | methyl | hydrogen | 15-epi-15,16-dimethyl, methyl ester |
| D-3 | 2 | methyl | hydrogen | hydrogen | methyl | α | methyl | hydrogen | 15-epi, methyl ester, 15-methyl ether |
| D-4 | 2 | methyl | methyl | hydrogen | hydrogen | α | methyl | hydrogen | 15-epi-16,16-dimethyl, methyl ester |
| D-5 | 2 | methyl | methyl | methyl | hydrogen | α | methyl | hydrogen | 15-epi-15,16,16-trimethyl, methyl ester |
| D-6 | 2 | methyl | methyl | hydrogen | methyl | α | methyl | hydrogen | 15-epi-16,16-dimethyl, methyl ester, 15-methyl ether |
| D-7 | 2 | fluoro | hydrogen | hydrogen | hydrogen | α | methyl | hydrogen | 15-epi-16-fluoro, methyl ester |
| D-8 | 2 | fluoro | hydrogen | methyl | hydrogen | α | methyl | hydrogen | 15-epi-15-methyl-16-fluoro, methyl ester |
| D-9 | 2 | fluoro | hydrogen | hydrogen | methyl | α | methyl | hydrogen | 15-epi-16-fluoro, methyl ester, 15-methyl ether |
| D-10 | 2 | fluoro | fluoro | hydrogen | hydrogen | α | methyl | hydrogen | 15-epi-16,16-difluoro, methyl ester |
| D-11 | 2 | fluoro | fluoro | methyl | hydrogen | α | methyl | hydrogen | 15-epi-15-methyl-16,16-difluoro, methyl ester |
| D-12 | 2 | fluoro | fluoro | hydrogen | methyl | α | methyl | hydrogen | 15-epi-16,16-difluoro, methyl ester, 15-methyl ether |
| D-13 | 2 | hydrogen | hydrogen | hydrogen | hydrogen | α | methyl | hydrogen | 15-epi, methyl ester |
| D-14 | 2 | hydrogen | hydrogen | methyl | hydrogen | α | methyl | hydrogen | 15-epi-15-methyl, methyl ester |
| D-15 | 2 | hydrogen | hydrogen | hydrogen | methyl | α | methyl | hydrogen | 15-epi, methyl ester, 15-methyl ether |
| D-16 | 2 | methyl | hydrogen | hydrogen | hydrogen | α | methyl | fluoro | 15-epi-2,2-difluoro-16-methyl, methyl ester |
| D-17 | 2 | methyl | hydrogen | methyl | hydrogen | α | methyl | fluoro | 15-epi-2,2-difluoro-15,16-dimethyl, methyl ester |
| D-18 | 2 | methyl | hydrogen | hydrogen | methyl | α | methyl | fluoro | 15-epi-2,2-difluoro, methyl ester, 15-methyl ether |
| D-19 | 2 | methyl | methyl | hydrogen | hydrogen | α | methyl | fluoro | 15-epi-2,2-difluoro-16,16-dimethyl, methyl ester |
| D-20 | 2 | methyl | methyl | methyl | hydrogen | α | methyl | fluoro | 15-epi-2,2-difluoro-15,16,16-trimethyl, methyl ester |
| D-21 | 2 | methyl | methyl | hydrogen | methyl | α | methyl | fluoro | 15-epi-2,2-difluoro-16,16-dimethyl, methyl ester |
| D-22 | 2 | fluoro | hydrogen | hydrogen | hydrogen | α | methyl | fluoro | 15-epi-2,2,16-trifluoro, |

Table D-continued

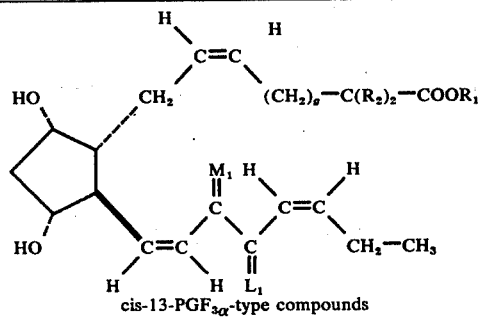

cis-13-PGF$_{3\alpha}$-type compounds

| Example | g | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|
| D-23 | 2 | fluoro | hydrogen | methyl | hydrogen | α | methyl | fluoro | 15-epi-2,2,16-trifluoro-15-methyl, methyl ester |
| D-24 | 2 | fluoro | hydrogen | hydrogen | methyl | α | methyl | fluoro | 15-epi-2,2,16-trifluoro, methyl ester, 15-methyl ether |
| D-25 | 2 | fluoro | fluoro | hydrogen | hydrogen | α | methyl | fluoro | 15-epi-2,2,16,16-tetrafluoro, methyl ester |
| D-26 | 2 | fluoro | fluoro | methyl | hydrogen | α | methyl | fluoro | 15-epi-2,2,16,16-tetrafluoro-15-methyl, methyl ester |
| D-27 | 2 | fluoro | fluoro | hydrogen | methyl | α | methyl | fluoro | 15-epi-2,2,16,16-tetrafluoro, methyl ester, 15-methyl ether |
| D-28 | 2 | hydrogen | hydrogen | hydrogen | hydrogen | α | methyl | fluoro | 15-epi-2,2-difluoro, methyl ester |
| D-29 | 2 | hydrogen | hydrogen | methyl | hydrogen | α | methyl | fluoro | 15-epi-2,2-difluoro-15-methyl, methyl ester |
| D-30 | 2 | hydrogen | hydrogen | hydrogen | methyl | α | methyl | fluoro | 15-epi-2,2-difluoro, methyl ester, 15-methyl ether |
| D-31 | 4 | hydrogen | hydrogen | hydrogen | hydrogen | α | methyl | hydrogen | 15-epi-2a,2b-dihomo, methyl ester |
| D-32 | 4 | hydrogen | hydrogen | methyl | hydrogen | α | methyl | hydrogen | 15-epi-2a,2b-dihomo-15-methyl, methyl ester |
| D-33 | 4 | methyl | methyl | hydrogen | hydrogen | α | methyl | hydrogen | 15-epi-2a,2b-dihomo-16,16-dimethyl, methyl ester |
| D-34 | 4 | methyl | methyl | methyl | hydrogen | α | methyl | hydrogen | 15-epi-2a,2b-dihomo-15,16,16-trimethyl, methyl ester |
| D-35 | 4 | fluoro | fluoro | hydrogen | hydrogen | α | methyl | hydrogen | 15-epi-2a,2b-dihomo-16,16-difluoro, methyl ester |
| D-36 | 4 | fluoro | fluoro | methyl | hydrogen | α | methyl | hydrogen | 15-epi-2a,2b-dihomo-15-methyl-16,16-difluoro, methyl ester |

Table E

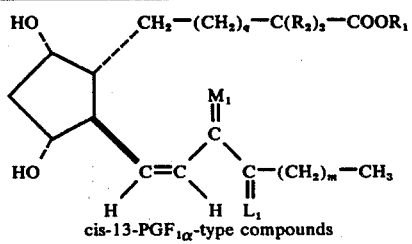

cis-13-PGF$_{1\alpha}$-type compounds

| Example | q | m | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|---|
| E-1 | 4 | 3 | methyl | hydrogen | hydrogen | hydrogen | α | methyl | hydrogen | 15-epi-16-methyl, methyl ester |
| E-2 | 4 | 3 | methyl | hydrogen | methyl | hydrogen | α | metyl | hydrogen | 15-epi-15,16-dimethyl, methyl ester |
| E-3 | 4 | 3 | methyl | hydrogen | hydrogen | methyl | α | methyl | hydrogen | 15-epi, methyl ester, 15-methyl ether |
| E-4 | 4 | 3 | methyl | methyl | hydrogen | hydrogen | α | methyl | hydrogen | 15-epi-16,16-dimethyl, methyl ester |
| E-5 | 4 | 3 | methyl | methyl | methyl | hydrogen | α | methyl | hydrogen | 15-epi-15,16,16-trimethyl, methyl ester |
| E-6 | 4 | 3 | methyl | methyl | hydrogen | methyl | α | methyl | hydrogen | 15-epi-16,16-dimethyl, methyl ester, 15-methyl ether |
| E-7 | 4 | 3 | fluoro | hydrogen | hydrogen | hydrogen | α | methyl | hydrogen | 15-epi-16-fluoro, methyl ester |
| E-8 | 4 | 3 | fluoro | hydrogen | methyl | hydrogen | α | methyl | hydrogen | 15-epi-15-methyl-16-fluoro, methyl ester |
| E-9 | 4 | 3 | fluoro | hydrogen | hydrogen | methyl | α | methyl | hydrogen | 15-epi-16-fluoro, methyl ester, 15-methyl ether |
| E-10 | 4 | 3 | fluoro | fluoro | hydrogen | hydrogen | α | methyl | hydrogen | 15-epi-16,16-difluoro, methyl ester |
| E-11 | 4 | 3 | fluoro | fluoro | methyl | hydrogen | α | methyl | hydrogen | 15-epi-15-methyl-16,16-difluoro, methyl ester |
| E-12 | 4 | 3 | fluoro | fluoro | hydrogen | methyl | α | methyl | hydrogen | 15-epi-16,16-difluoro, methyl |

Table E-continued

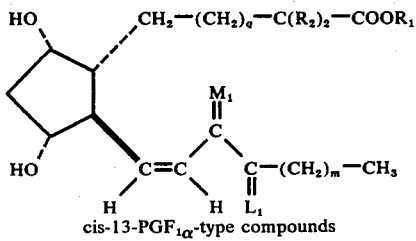

cis-13-PGF$_{1\alpha}$-type compounds

| Example | q | m | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|---|
| E-13 | 4 | 3 | hydrogen | hydrogen | hydrogen | methyl | α | methyl | hydrogen | ester, 15-methyl ether 15-epi, methyl ester, 15-methyl ether |
| E-14 | 4 | 3 | methyl | hydrogen | hydrogen | hydrogen | α | methyl | fluoro | 15-epi-2,2-difluoro-16-methyl, methyl ester |
| E-15 | 4 | 3 | methyl | hydrogen | metyl | hydrogen | α | methyl | fluoro | 15-epi-2,2-difluoro-15,16-dimethyl, methyl ester |
| E-16 | 4 | 3 | methyl | hydrogen | hydrogen | methyl | α | methyl | fluoro | 15-epi-2,2-difluoro, methyl ester, 15-methyl ether |
| E-17 | 4 | 3 | methyl | methyl | hydrogen | hydrogen | α | methyl | fluoro | 15-epi-2,2-difluoro-16,16-dimethyl, methyl ester |
| E-18 | 4 | 3 | methyl | methyl | methyl | hydrogen | α | methyl | fluoro | 15-epi-2,2-difluoro-15,16,16-trimethyl, methyl ester |
| E-19 | 4 | 3 | methyl | methyl | hydrogen | methyl | α | methyl | fluoro | 15-epi-2,2-difluoro-16,16-dimethyl, methyl ester, 15-methyl ether |
| E-20 | 4 | 3 | fluoro | hydrogen | hydrogen | hydrogen | α | methyl | fluoro | 15-epi-2,2,16-trifluoro, methyl ester |
| E-21 | 4 | 3 | fluoro | hydrogen | methyl | hydrogen | α | methyl | fluoro | 15-epi-2,2,16-trifluoro-15-methyl, methyl ester |
| E-22 | 4 | 3 | fluoro | hydrogen | hydrogen | methyl | α | methyl | fluoro | 15-epi-2,2,16-trifluoro, methyl ester, 15-methyl ether |
| E-23 | 4 | 3 | fluoro | fluoro | hydrogen | hydrogen | α | methyl | fluoro | 15-epi-2,2,16,16-tetrafluoro-16,16-difluoro, methyl ester |
| E-24 | 4 | 3 | fluoro | fluoro | methyl | hydrogen | α | methyl | fluoro | 15-epi-2,2,16,16-tetrafluoro-15-methyl, methyl ester |
| E-25 | 4 | 3 | fluoro | fluoro | hydrogen | methyl | α | methyl | fluoro | 15-epi-2,2,16,16-tetrafluoro, methyl ester, 15-methyl ether |
| E-26 | 4 | 3 | hydrogen | hydrogen | hydrogen | hydrogen | α | methyl | fluoro | 15-epi-2,2-difluoro, methyl ester |
| E-27 | 4 | 3 | hydrogen | hydrogen | methyl | hydrogen | α | methyl | fluoro | 15-epi-2,2-difluoro-15-methyl, methyl ester |
| E-28 | 4 | 3 | hydrogen | hydrogen | hydrogen | methyl | α | methyl | fluoro | 15-epi-2,2-difluoro, methyl ester, 15-methyl ether |
| E-29 | 6 | 3 | methyl | methyl | hydrogen | hydrogen | α | methyl | hydrogen | 15-epi-2a,2b-dihomo-16,16-dimethyl, methyl ester |
| E-30 | 6 | 3 | methyl | methyl | methyl | hydrogen | α | methyl | hydrogen | 15-epi-2a,2b-dihomo-15,16,16-trimethyl, methyl ester |
| E-31 | 6 | 3 | fluoro | fluoro | hydrogen | hydrogen | α | methyl | hydrogen | 15-epi-2a,2b-dihomo-16,16-difluoro, methyl ester |
| E-32 | 6 | 3 | fluoro | fluoro | methyl | hydrogen | α | methyl | hydrogen | 15-epi-2a,2b-dihomo-15-methyl-16,16-difluoro, methyl ester |

Table F

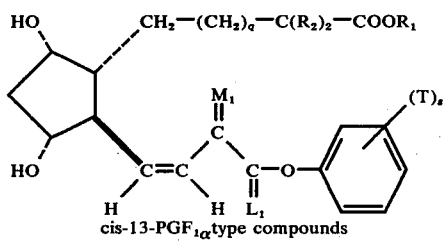

cis-13-PGF$_{1\alpha}$type compounds

| Example | q | s | T | R$_3$ | R$_4$ | R$_5$ | R$_6$ | ~OR$_6$ | R$_1$ | R$_2$ | Name |
|---|---|---|---|---|---|---|---|---|---|---|---|
| F-1 | 4 | 0 |  | hydrogen | hydrogen | hydrogen | hydrogen | α | methyl | hydrogen | 15-epi-16-phenoxy-17,18,19,20-tetranor, methyl ester |
| F-2 | 4 | 1 | p-fluoro | hydrogen | hydrogen | hydrogen | hydrogen | α | methyl | hydrogen | 16-(p-fluorophenoxy)-17,18,19,20-tetranor, methyl ester |
| F-3 | 4 | 1 | m-chloro | hydrogen | hydrogen | hydrogen | hydrogen | α | methyl | hydrogen | 16-(m-chlorophenoxy)-17,18,19,20-tetranor, methyl ester |
| F-4 | 4 | 1 | m-trifluoro | hydrogen | hydrogen | hydrogen | hydrogen | α | methyl | hydrogen | 15-epi-16-(m-trifluoromethylphenoxy)-17,18,19,20-tetranor, methyl ester |
| F-5 | 4 | 0 |  | hydrogen | hydrogen | methyl | hydrogen | α | methyl | hydrogen | 15-epi-15-methyl-16- |

Table F-continued

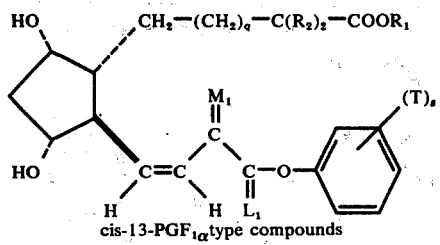

cis-13-PGF$_{1\alpha}$ type compounds

| Example | q | s | T | R$_3$ | R$_4$ | R$_5$ | R$_6$ | ~OR$_6$ | R$_1$ | R$_2$ | Name |
|---|---|---|---|---|---|---|---|---|---|---|---|
| | | | | gen | gen | | gen | | | gen | phenoxy-17,18,19,20-tetranor, methyl ester |
| F-6 | 4 | 1 | p-fluoro | hydrogen | hydrogen | methyl | hydrogen | α | methyl | hydrogen | 15-epi-15-methyl-16-(p-fluorophenoxy)-17,18,19,20-tetranor, methyl ester |
| F-7 | 4 | 1 | m-chloro | hydrogen | hydrogen | methyl | hydrogen | α | methyl | hydrogen | 15-epi-15-methyl-16-(m-chlorophenoxy), methyl ester |
| F-8 | 4 | 1 | m-trifluoro | hydrogen | hydrogen | methyl | hydrogen | α | methyl | hydrogen | 15-epi-15-methyl-16-(m-trifluoromethylphenoxy), methyl ester |
| F-9 | 4 | 0 | | hydrogen | hydrogen | hydrogen | methyl | α | methyl | hydrogen | 15-epi-16-phenoxy-17,18,19,20-tetranor, methyl ester, 15-methyl ether |
| F-10 | 4 | 1 | p-fluoro | hydrogen | hydrogen | hydrogen | methyl | α | methyl | hydrogen | 15-epi-16-(p-fluorophenoxy)-17,18,19,20-tetranor, methyl ester, 15-methyl ether |
| F-11 | 4 | 1 | m-chloro | hydrogen | hydrogen | hydrogen | methyl | α | methyl | hydrogen | 15-epi-16-(m-chlorophenoxy)-17,18,19,20-tetranor, methyl ester, 15-methyl ether |
| F-12 | 4 | 1 | m-trifluoromethyl | hydrogen | hydrogen | hydrogen | methyl | α | methyl | hydrogen | 15-epi-16-(m-trifluoromethylphenoxy)-17,18,19,20-tetranor, methyl ester, 15-methyl ether |
| F-13 | 4 | 0 | | methyl | methyl | hydrogen | hydrogen | α | methyl | hydrogen | 15-epi-16-methyl-16-phenoxy-18,19,20-trinor, methyl ester |
| F-14 | 4 | 1 | p-fluoro | methyl | methyl | hydrogen | hydrogen | α | methyl | hydrogen | 15-epi-16-methyl-16-(p-fluorophenoxy)-18,19,20-trinor, methyl ester |
| M-15 | 4 | 1 | m-chloro | methyl | methyl | hydrogen | hydrogen | α | methyl | hydrogen | 15-epi-16-methyl-16-(m-chlorophenoxy)-18,19,20-trinor, methyl ester |
| F-16 | 4 | 1 | m-trifluoromethyl | methyl | methyl | hydrogen | hydrogen | α | methyl | hydrogen | 15-epi-16-methyl-16-(m-trifluoromethylphenoxy)-18,19,20-trinor, methyl ester |
| F-17 | 4 | 0 | | methyl | methyl | methyl | hydrogen | α | methyl | hydrogen | 15-epi-15,16-dimethyl-16-phenoxy-18,19,20-trinor, methyl ester |
| F-18 | 4 | 1 | p-fluoro | methyl | methyl | methyl | hydrogen | α | methyl | hydrogen | 15-epi-15,16-dimethyl-16-(p-fluorophenoxy)-18,19,20-trinor, methyl ester |
| F-19 | 4 | 1 | m-chloro | methyl | methyl | methyl | hydrogen | α | methyl | hydrogen | 15-epi-15,16-dimethyl-16-(m-chlorophenoxy)-18,19,20-trinor, methyl ester |
| F-20 | 4 | 1 | m-trifluoromethyl | methyl | methyl | methyl | hydrogen | α | methyl | hydrogen | 15-epi-15,16-dimethyl-16-(m-trifluoromethylphenoxy)-18,19,20-trinor, methyl ester |
| F-21 | 4 | 0 | | methyl | methyl | hydrogen | methyl | α | methyl | hydrogen | 15-epi-16-methyl-16-phenoxy-18,19,20-trinor, methyl ester, 15-methyl ether |
| F-22 | 4 | 1 | p-fluoro | methyl | methyl | hydrogen | methyl | α | methyl | hydrogen | 15-epi-16-methyl-16-(p-fluorophenoxy)-18,19,20-trinor, methyl ester, 15-methyl ether |
| F-23 | 4 | 1 | m-chloro | methyl | methyl | hydrogen | methyl | α | methyl | hydrogen | 15-epi-16-methyl-16-(m-chlorophenoxy)-18,19,20-trinor, methyl ester, 15-methyl ether |
| F-24 | 4 | 1 | m-trifluoromethyl | methyl | methyl | hydrogen | methyl | α | methyl | hydrogen | 15-epi-16-methyl-16-(m-trifluoromethylphenoxy)-18,19,20-trinor, methyl ester, 15-methyl ether |
| F-25 | 4 | 0 | | hydrogen | hydrogen | hydrogen | hydrogen | α | methyl | fluoro | 15-epi-2,2-difluoro-16-phenoxy-17,18,19,20-tetranor, methyl ester |

Table F-continued

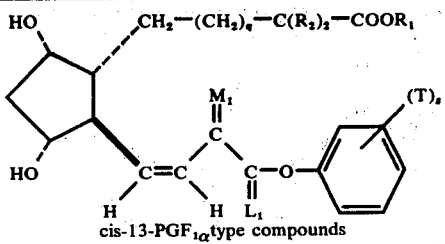

cis-13-PGF$_{1\alpha}$type compounds

| Example | q | s | T | R$_3$ | R$_4$ | R$_5$ | R$_6$ | ~OR$_6$ | R$_1$ | R$_2$ | Name |
|---|---|---|---|---|---|---|---|---|---|---|---|
| F-26 | 4 | 1 | p-fluoro | hydrogen | hydrogen | hydrogen | hydrogen | α | methyl | fluoro | 15-epi-2,2-difluoro-16-(p-fluorophenoxy)-17,18,19,20-tetranor, methyl ester |
| F-27 | 4 | 1 | m-chloro | hydrogen | hydrogen | hydrogen | hydrogen | α | methyl | fluoro | 15-epi-2,2-difluoro-16-(m-chlorophenoxy)-17,18,19,20-tetranor, methyl ester |
| F-28 | 4 | 1 | m-trifluoromethyl | hydrogen | hydrogen | hydrogen | hydrogen | α | methyl | fluoro | 15-epi-2,2-difluoro-16-(m-trifluoromethylphenoxy)-17,18,19,20-tetranor, methyl ester |
| F-29 | 4 | 0 | | hydrogen | hydrogen | methyl | hydrogen | α | methyl | fluoro | 15-epi-2,2-difluoro-15-methyl-16-phenoxy-17,18,19,20-tetranor, methyl ester |
| F-30 | 4 | 1 | p-fluoro | hydrogen | hydrogen | methyl | hydrogen | α | methyl | fluoro- | 15-epi-2,2-difluoro-15-methyl-16-(p-fluorophenoxy)-17,18,19,20-tetranor, methyl ester |
| F-31 | 4 | 1 | m-chloro | hydrogen | hydrogen | methyl | hydrogen | α | methyl | fluoro | 15-epi-2,2-difluoro-15-methyl-16-(m-chlorophenoxy), methyl ester |
| F-32 | 4 | 1 | m-trifluoromethyl | hydrogen | hydrogen | methyl | hydrogen | α | methyl | fluoro | 15-epi-2,2-difluoro-15-methyl-16-(m-trifluoromethylphenoxy), methyl ester |
| F-33 | 4 | 0 | | hydrogen | hydrogen | hydrogen | methyl | α | methyl | fluoro | 15-epi-2,2-difluoro-16-phenoxy-17,18,19,20-tetranor, methyl ester, 15-methyl ether |
| F-34 | 4 | 1 | p-fluoro | hydrogen | hydrogen | hydrogen | methyl | α | methyl | fluoro | 15-epi-2,2-difluoro-16-(p-fluorophenoxy)-17,18,19,20-tetranor, methyl ester, 15-methyl ether |
| F-35 | 4 | 1 | m-chloro | hydrogen | hydrogen | hydrogen | methyl | α | methyl | fluoro | 15-epi-2,2-difluoro-16-(m-chlorophenoxy)-17,18,19,20-tetranor, methyl ester, 15-methyl ether |
| F-36 | 4 | 1 | m-trifluoro | hydrogen | hydrogen | hydrogen | methyl | α | methyl | fluoro | 15-epi-2,2-difluoro-16-(m-trifluoromethylphenoxy)-17,18,19,20-tetranor, methyl ester, 15-methyl ether |
| F-37 | 4 | 0 | | methyl | methyl | hydrogen | hydrogen | α | methyl | fluoro | 15-epi-2,2-difluoro-16-phenoxy-18,19,20-trinor, methyl ester |
| F-38 | 4 | 1 | p-fluoro | methyl | methyl | hydrogen | hydrogen | α | methyl | fluoro | 15-epi-2,2-difluoro-16-methyl-16-(p-fluorophenoxy)-18,19,20-trinor, methyl ester |
| F-39 | 4 | 1 | m-chloro | methyl | methyl | hydrogen | hydrogen | α | methyl | fluoro | 15-epi-2,2-difluoro-16-methyl-16-(m-chlorophen- |
| F-40 | 4 | 1 | m-trifluoromethyl | methyl | methyl | hydrogen | hydrogen | α | methyl | fluoro | 15-epi-2,2-difluoro-16-methyl-16-(m-trifluoromethylphenoxy)-18,19,20-trinor, methyl ester |
| F-41 | 4 | 0 | | methyl | methyl | methyl | hydrogen | α | methyl | fluoro | 15-epi-2,2-difluoro-15,16-dimethyl-16-phenoxy-18,19,20-trinor, methyl ester |
| F-42 | 4 | 1 | p-fluoro | methyl | methyl | methyl | hydrogen | α | methyl | fluoro | 15-epi-2,2-difluoro-15,16-dimethyl-16-(p-fluorophenoxy)-18,19,20-trinor, methyl ester |
| F-43 | 4 | 1 | m-chloro | methyl | methyl | methyl | hydrogen | α | methyl | fluoro | 15-epi-2,2-difluoro-15,16-dimethyl-16-(m-chlorophenoxy)-18,19,20-trinor, methyl ester |
| F-44 | 4 | 1 | m-trifluoromethyl | methyl | methyl | methyl | hydrogen | α | methyl | fluoro | 15-epi-2,2-difluoro-15,16-dimethyl-16-(m-trifluoromethylphenoxy)-18,19,20-trinor, methyl ester |
| F-45 | 4 | 0 | | methyl | methyl | hydrogen | methyl | α | methyl | fluoro | 15-epi-2,2-difluoro-16- |

Table F-continued

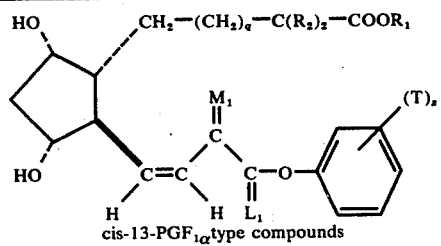

cis-13-PGF$_{1\alpha}$type compounds

| Example | q | s | T | R$_3$ | R$_4$ | R$_5$ | R$_6$ | ~OR$_6$ | R$_1$ | R$_2$ | Name |
|---|---|---|---|---|---|---|---|---|---|---|---|
| F-46 | 4 | 1 | p-fluoro | methyl | methyl | hydrogen | methyl | α | methyl | fluoro | 15-epi-2,2-difluoro-16-methyl-16-(p-fluorophenoxy)-18,19,20-trinor, methyl ester, 15-methyl ether |
| F-47 | 4 | 1 | m-chloro | methyl | methyl | hydrogen | methyl | α | methyl | fluoro | 15-epi-2,2-difluoro-16-methyl-16-(m-chlorophenoxy)-18,19,20-trinor, methyl ester, 15-methyl ether |
| F-48 | 4 | 1 | m-trifluoromethyl | methyl | methyl | hydrogen | methyl | α | methyl | fluoro | 15-epi-2,2-difluoro-16-methyl-16-(m-trifluoromethylphenoxy)-18,19,20-trinor, methyl ester, 15-methyl ether |
| F-49 | 6 | 0 |  | hydrogen | hydrogen | hydrogen | hydrogen | α | methyl | hydrogen | 15-epi-2a,2b-dihomo-16-phenoxy-17,18,19,20-tetranor, methyl ester |
| F-50 | 6 | 1 | p-fluoro | hydrogen | hydrogen | hydrogen | hydrogen | α | methyl | hydrogen | 15-epi-2a,2b-dihomo-16-(p-fluorophenoxy)-17,18,19,20-tetranor, methyl ester |
| F-51 | 6 | 1 | m-chloro | hydrogen | hydrogen | hydrogen | hydrogen | α | methyl | hydrogen | 15-epi-2a,2b-dihomo-16-(m-chlorophenoxy)-17,18,19,20-tetranor, methyl ester |
| F-52 | 6 | 1 | m-trifluoromethyl | hydrogen | hydrogen | hydrogen | hydrogen | α | methyl | hydrogen | 15-epi-2a,2b-dihomo-16-(m-trifluoromethylphenoxy)-17,18,19,20-tetranor, methyl ester |
| F-53 | 6 | 0 |  | hydrogen | hydrogen | methyl | hydrogen | α | methyl | hydrogen | 15-epi-2a,2b-dihomo-15-methyl-16-phenoxy-17,18,19,20-tetranor, methyl ester |
| F-54 | 6 | 1 | p-fluoro | hydrogen | hydrogen | methyl | hydrogen | α | methyl | hydrogen | 15-epi-2a,2b-dihomo-16-(p-fluorophenoxy)-17,18,19,20-tetranor, methyl ester |
| F-55 | 6 | 0 | m-chooro | hydrogen | hydrogen | methyl | hydrogen | α | methyl | hydrogen | 15-epi-2a,2b-dihomo-15-methyl-16-(m-chlorophenoxy)-17,18,19,20-tetranor, methyl ester |
| F-56 | 6 | 1 | m-trifluoro | hydrogen | hydrogen | methyl | hydrogen | α | methyl | hydrogen | 15-epi-2a,2b-dihomo-15-methyl-16-(m-trifluoro-17,18,19,20-tetranor, methyl ester |

Table G

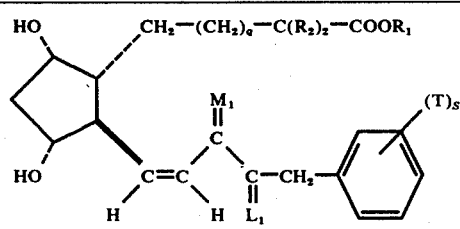

cis-13,18,19,20-trinor-PGF$_{1\alpha}$-type compounds

| Example | q | s | T | L$_1$ | | M$_1$ | | ~OR$_6$ | R$_1$ | R$_2$ | Name |
| | | | | R$_3$ | R$_4$ | R$_5$ | R$_6$ | | | | |
|---|---|---|---|---|---|---|---|---|---|---|---|
| G-1 | 4 | 0 |  | hydrogen | hydrogen | hydrogen | hydrogen | α | methyl | hydrogen | 15-epi-17-phenyl, methyl ester |
| G-2 | 4 | 1 | p-fluoro | hydrogen | hydrogen | hydrogen | hydrogen | α | methyl | hydrogen | 15-epi-17-(p-fluorophenyl), methyl ester |
| G-3 | 4 | 1 | m-chloro | hydrogen | hydrogen | hydrogen | hydrogen | α | methyl | hydrogen | 15-epi-17-(m-chlorophenyl), methyl ester |

Table G-continued

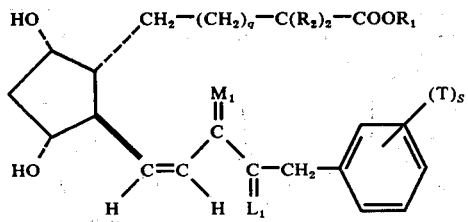

cis-13,18,19,20-trinor-PGF$_{1\alpha}$-type compounds

| Example | q | s | T | L$_1$ R$_3$ | R$_4$ | R$_5$ | M$_1$ R$_6$ | ~OR$_6$ | R$_1$ | R$_2$ | Name |
|---|---|---|---|---|---|---|---|---|---|---|---|
| G-4 | 4 | 1 | m-trifluoromethyl | hydrogen | hydrogen | hydrogen | hydrogen | α | methyl | hydrogen | 15-ei-17-(m-trifluoromethylphenyl, methyl ester |
| G-5 | 4 | 0 | | hydrogen | hydrogen | methyl | hydrogen | α | methyl | hydrogen | 15-epi-15-methyl-17-phenyl, methyl ester |
| G-6 | 4 | 1 | p-fluoro | hydrogen | hydrogen | methyl | hydrogen | α | methyl | hydrogen | 15-epi-15-methyl-17-(p-fluorophenyl), methyl ester |
| G-7 | 4 | 1 | m-chloro | hydrogen | hydrogen | methyl | hydrogen | α | methyl | hydrogen | 15-epi-15-methyl-17-(m-chlorophenyl), methyl ester |
| G-8 | 4 | 1 | m-trifluoromethyl | hydrogen | hydrogen | methyl | hydrogen | α | methyl | hydrogen | 15-epi-15-methyl-17-(m-trifluoromethylphenyl), methyl ester |
| G-9 | 4 | 0 | | hydrogen | hydrogen | hydrogen | methyl | α | methyl | hydrogen | 15-epi-17-phenyl, methyl ester, 15-methyl ether |
| G-10 | 4 | 1 | p-fluoro | hydrogen | hydrogen | hydrogen | methyl | α | methyl | hydrogen | 15-epi-17-(P-fluorophenyl), methyl ester, 15-methyl ether |
| G-11 | 4 | 1 | m-chloro | hydrogen | hydrogen | hydrogen | methyl | α | methyl | hydrogen | 15-epi-17-(m-chlorophenyl), methyl ester, 15-methyl ether |
| G-12 | 4 | 1 | m-trifluoromethyl | hydrogen | hydrogen | hydrogen | methyl | α | methyl | hydrogen | 15-epi-17-(m-trifluoromethylphenyl), methyl ester, 15-methyl ether |
| G-13 | 4 | 0 | | methyl | methyl | hydrogen | hydrogen | α | methyl | hydrogen | 15-epi-16,16-dimethyl-17-phenyl, methyl ester |
| G-14 | 4 | 1 | p-fluoro | methyl | methyl | hydrogen | hydrogen | α | methyl | hydrogen | 15-epi-16,16-dimethyl-17-(p-fluorophenyl), methyl ester |
| G-15 | 4 | 1 | m-chloro | methyl | methyl | hydrogen | hydrogen | α | methyl | hydrogen | 15-epi-16,16-dimethyl-17-(m-chlorophenyl), methyl ester |
| G-16 | 4 | 1 | m-trifluoromethyl | methyl | methyl | hydrogen | hydrogen | α | methyl | hydrogen | 15-epi-16,16-dimethyl-17-(m-trifluoromethylphenyl), methyl ester |
| G-17 | 4 | 0 | | methyl | methyl | methyl | hydrogen | α | methyl | hydrogen | 15-epi-15,16,16-trimethyl-17-phenyl, methyl ester |
| G-18 | 4 | 1 | p-fluoro | methyl | methyl | methyl | hydrogen | α | methyl | hydrogen | 15-epi-15,16,16-trimethyl-17-(p-fluorophenyl), methyl ester |
| G-19 | 4 | 1 | m-chloro | methyl | methyl | methyl | hydrogen | α | methyl | hydrogen | 15-epi-15,16,16-trimethyl-17-(m-chlorophenyl), methyl ester |
| G-20 | 4 | 1 | m-trifluoromethyl | methyl | methyl | methyl | hydrogen | α | methyl | hydrogen | 15-epi-15,16,16-trimethyl-17(m-trifluoromethylphenyl), methyl ester |
| G-21 | 4 | 0 | | methyl | methyl | hydrogen | methyl | α | methyl | hydrogen | 15-epi-16,16-dimethyl-17-phenyl, methyl ester, 15-methyl ether |
| G-22 | 4 | 1 | p-fluoro | methyl | methyl | hydrogen | methyl | α | methyl | hydrogen | 15-epi-16,16-dimethyl-17-(p-fluorophenyl), methyl ester, 15-methyl ether |
| G-23 | 4 | 1 | m-chloro | methyl | methyl | hydrogen | methyl | α | methyl | hydrogen | 15-epi-16,16-dimethyl-17-(m-chlorophenyl), methyl ester, 15-methyl ether |
| G-24 | 4 | 1 | m-trifluoromethyl | methyl | methyl | hydrogen | methyl | α | methyl | hydrogen | 15-epi-16,16-dimethyl-17-(m-trifluoromethylphenyl), methyl ester, 15-methyl ether |
| G-25 | 4 | 0 | | hydrogen | hydrogen | hydrogen | hydrogen | α | methyl | fluoro | 15-epi-2,2-difluoro-17-phenyl, methyl ester |
| G-26 | 4 | 1 | p-fluoro | hydrogen | hydrogen | hydrogen | hydrogen | α | methyl | fluoro | 15-epi-2,2-difluoro-17-(p-fluorophenyl), methyl ester |
| G-27 | 4 | 1 | m-chloro | hydrogen | hydrogen | hydrogen | hydrogen | α | methyl | fluoro | 15-epi-2,2-difluoro-17-(m-chlorophenyl), methyl ester |
| G-28 | 4 | 1 | m-trifluoro | hydrogen | hydrogen | hydrogen | hydrogen | α | methyl | fluoro | 15-epi-2,2-difluoro-17-(m-trifluoromethylphenyl), methyl ester |
| G-29 | 4 | 0 | | hydrogen | hydrogen | methyl | hydrogen | α | methyl | fluoro | 15-epi-2,2-difluoro-15- |

Table G-continued

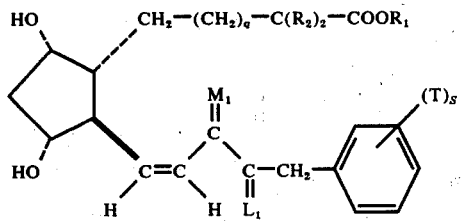

cis-13,18,19,20-trinor-PGF$_{1\alpha}$-type compounds

| Example | q | s | T | L$_1$ R$_3$ | R$_4$ | M$_1$ R$_5$ | R$_6$ | ~OR$_6$ | R$_1$ | R$_2$ | Name |
|---|---|---|---|---|---|---|---|---|---|---|---|
|  |  |  |  | gen | gen |  | gen |  |  |  | methyl-17-phenyl, methyl ester |
| G-30 | 4 | 1 | p-fluoro | hydrogen | hydrogen | methyl | hydrogen | α | methyl | hydrogen | 15-epi-2,2-difluoro-15-methyl-17-(p-fluorophenyl), methyl ester |
| G-31 | 4 | 1 | m-chloro | hydrogen | hydrogen | methyl | hydrogen | α | methyl | fluoro | 15-epi-2,2-difluoro-15-methyl-17-(m-chlorophenyl), methyl ester |
| G-32 | 4 | 1 | m-trifluoromethyl | hydrogen | hydrogen | methyl | hydrogen | α | methyl | fluoro | 15-epi-2,2-difluoro-15-methyl-17-(m-trifluoromethylphenyl), methyl ester |
| G-33 | 4 | 0 |  | hydrogen | hydrogen | hydrogen | methyl | α | methyl | fluoro | 15-epi-2,2-difluoro-17-phenyl, methyl ester, 15-methyl ether |
| G-34 | 4 | 1 | p-fluoro | hydrogen | hydrogen | hydrogen | methyl | α | methyl | fluoro | 15-epi-2,2-difluoro-17-(p-fluorophenyl), methyl ester, 15-methyl ether |
| G-35 | 4 | 1 | m-chloro | hydrogen | hydrogen | hydrogen | methyl | α | methyl | fluoro | 15-epi-2,2-difluoro-17-(m-chlorophenyl), methyl ester, 15-methyl ether |
| G-36 | 4 | 1 | m-trifluoro | hydrogen | hydrogen | hydrogen | methyl | α | methyl | fluoro | 15-epi-2,2-difluoro-17-(m-trifluoromethylphenyl), methyl ester, 15-methyl ether |
| G-37 | 4 | 0 |  | methyl | methyl | hydrogen | hydrogen | α | methyl | fluoro | 15-epi-2,2-difluoro-16,16-dimethyl-17-phenyl, methyl ester |
| G-38 | 4 | 1 | p-fluoro | methyl | methyl | hydrogen | hydrogen | α | methyl | fluoro | 15-epi-2,2-difluoro-16,16-dimethyl-17-(p- ester |
| G-39 | 4 | 1 | m-chloro | methyl | methyl | hydrogen | hydrogen | α | methyl | fluoro | 15-epi-2,2-difluoro-16,16-dimethyl-17-(m-chlorophenyl), methyl ester |
| G-40 | 4 | 1 | m-trifluoromethyl | methyl | methyl | hydrogen | hydrogen | α | methyl | fluoro | 15-epi-2,2-difluoro-16,16-dimethyl-17-(m-trifluoromethylphenyl), methyl ester |
| G-41 | 4 | 0 |  | methyl | methyl | methyl | hydrogen | α | methyl | fluoro | 15-epi-2,2-difluoro-15,16,16-trimethyl-17-phenyl, methyl ester |
| G-42 | 4 | 1 | p-fluoro | methyl | methyl | methyl | hydrogen | α | methyl | fluoro | 15-epi-2,2-difluoro-15,16,16-trimethyl-17-(p-fluorophenyl), methyl ester |
| G-43 | 4 | 1 | m-chloro | methyl | methyl | methyl | hydrogen | α | methyl | fluoro | 15-epi-2,2-difluoro-15,16,16-trimethyl-17-(m-chlorophenyl), methyl ester |
| G-44 | 4 | 1 | m-trifluoromethyl | methyl | methyl | methyl | hydrogen | α | methyl | fluoro | 15-epi-2,2-difluoro-15,16,16-trimethyl-17-(m-trifluoromethylphenyl), methyl ester |
| G-45 | 4 | 0 |  | methyl | methyl | hydrogen | methyl | α | methyl | fluoro | 15-epi-2,2-difluoro-16,16-dimethyl-17-phenyl, ester, 15-methyl ether methyl ether |
| G-46 | 4 | 1 | p-fluoro | methyl | methyl | hydrogen | methyl | α | methyl | fluoro | 15-epi-2,2-difluoro-16,16-dimethyl-17-(p-fluorophenyl), methyl ester, 15-methyl ether |
| G-47 | 4 | 1 | m-chloro | methyl | methyl | hydrogen | methyl | α | methyl | fluoro | 15-epi-2,2-difluoro-16,16-dimethyl-17-(m-chlorophenyl), methyl ester, 15-methyl ether |
| G-48 | 4 | 1 | m-trifluoromethyl | methyl | methyl | hydrogen | methyl | α | methyl | fluoro | 15-epi-2,2-difluoro-16,16-dimethyl-17-(m-trifluoromethylphenyl), methyl ester, 15-methyl ether |
| G-49 | 6 | 0 |  | hydrogen | hydrogen | hydrogen | hydrogen | α | methyl | hydrogen | 15-epi-2a,2b-dihomo-17-phenyl, methyl ester |
| G-50 | 6 | 1 | p-fluoro | hydrogen | hydrogen | hydrogen | hydrogen | α | methyl | hydrogen | 15-epi-2a,2b-dihomo-17-(p-fluorophenyl), methyl |

Table G-continued

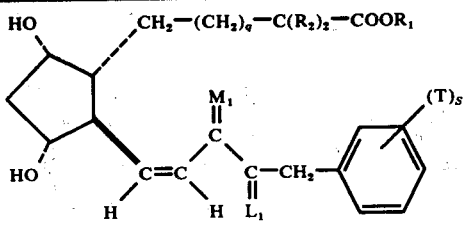

cis-13,18,19,20-trinor-PGF$_{1\alpha}$-type compounds

| Example | q | s | T | L$_1$ R$_3$ | L$_1$ R$_4$ | M$_1$ R$_5$ | M$_1$ R$_6$ | ~OR$_6$ | R$_1$ | R$_2$ | Name |
|---|---|---|---|---|---|---|---|---|---|---|---|
| G-51 | 6 | 1 | m-chloro | hydrogen | hydrogen | hydrogen | hydrogen | α | methyl | hydrogen | 15-epi-2a,2b-dihomo-17-(m-chlorophenyl), methyl ester |
| G-52 | 6 | 1 | m-trifluoromethyl | hydrogen | hydrogen | hydrogen | hydrogen | α | methyl | hydrogen | 15-epi-2a,2b-dihomo-17-(m-trifluoromethylphenyl), methyl ester |
| G-53 | 6 | 0 |  | hydrogen | hydrogen | methyl | hydrogen | α | methyl | hydrogen | 15-epi-2a,2b-dihomo-15-methyl-17-phenyl, methyl ester |
| G-54 | 6 | 1 | p-fluoro | hydrogen | hydrogen | methyl | hydrogen | α | methyl | hydrogen | 15-epi-2a,2b-dihomo-17-(p-fluorophenyl), methyl ester |
| G-55 | 6 | 0 | m-chloro | hydrogen | hydrogen | methyl | hydrogen | α | methyl | hydrogen | 15-epi-2a,2b-dihomo-15-methyl-17-(m-chlorophenyl), methyl ester |
| G-56 | 6 | 1 | m-trifluoro | hydrogen | hydrogen | methyl | hydrogen | α | methyl | hydrogen | 15-epi-2a,2b-dihomo-15-methyl-17-(m-trifluoromethylphenyl), methyl ester |
| G-57 | 2 | 0 |  | fluoro | fluoro | hydrogen | hydrogen | α | methyl | hydrogen | 15-epi-16,16-difluoro-17-phenyl, methyl ester |
| G-58 | 3 | 1 | p-fluoro | fluoro | fluoro | hydrogen | hydrogen | α | methyl | hydrogen | 15-epi-16,16-difluoro-17-(p-fluorophenyl), methyl ester |
| G-59 | 3 | 1 | m-chloro | fluoro | fluoro | hydrogen | hydrogen | α | methyl | hydrogen | 15-epi-16,16-difluoro-17-(m-chlorophenyl), methyl ester |
| G-60 | 2 | 1 | m-trifluoromethyl | fluoro | fluoro | hydrogen | hydrogen | α | methyl | hydrogen | 15-epi-16,16-difluoro-17-(m-trifluoromethylphenyl), methyl ester |
| G-61 | 2 | 0 |  | fluoro | fluoro | methyl | hydrogen | α | methyl | hydrogen | 15-epi-15-methyl-16,16-difluoro-17-phenyl, methyl ester |
| G-62 | 2 | 1 | p-fluoro | fluoro | fluoro | methyl | hydrogen | α | methyl | hydrogen | 15-epi-15-methyl-16,16-difluoro-17-(p-fluorophenyl), methyl ester |
| G-63 | 2 | 1 | m-chloro | fluoro | fluoro | methyl | hydrogen | α | methyl | hydrogen | 15-epi-15-methyl-16,16-difluoro-17-(m-chlorophenyl), methyl ester |
| G-64 | 2 | 1 | m-trifluoromethyl | fluoro | fluoro | methyl | hydrogen | α | methyl | hydrogen | 15-epi-15-methyl-16,16-difluoro-17-(m-trifluoromethylphenyl), methyl ester |
| G-65 | 2 | 0 |  | fluoro | fluoro | hydrogen | methyl | α | methyl | hydrogen | 15-epi-16,16-difluoro-17-phenyl, methyl ester, 15-methyl ether |
| G-66 | 2 | 1 | p-fluoro | fluoro | fluoro | hydrogen | methyl | α | methyl | hydrogen | 15-epi-16,16-difluoro-17-(p-fluorophenyl), methyl ester, 15-methyl ether |
| G-67 | 2 | 1 | m-chloro | fluoro | fluoro | hydrogen | methyl | α | methyl | hydrogen | 15-epi-16,16-difluoro-17-(m-chlorophenyl), methyl ester, 15-methyl ether |
| G-68 | 2 | 1 | m-trifluoromethyl | fluoro | fluoro | hydrogen | methyl | α | methyl | hydrogen | 15-epi-16,16-difluoro-17-(m-trifluoromethylphenyl), methyl ester, 15-methyl ether |
| G-69 | 2 | 0 |  | fluoro | fluoro | hydrogen | hydrogen | α | methyl | fluoro | 15-epi-2,2,16,16-tetrafluoro-16-phenoxy, methyl ester |
| G-70 | 2 | 1 | p-fluoro | fluoro | fluoro | hydrogen | hydrogen | α | methyl | fluoro | 15-epi-2,2,16,16-tetrafluoro-16-(p-fluorophenyl), methyl ester |
| G-71 | 2 | 1 | m-chloro | fluoro | fluoro | hydrogen | hydrogen | α | methyl | fluoro | 15-epi-2,2,16,16-tetrafluoro-16-(m-chlorophenyl), methyl ester |
| G-72 | 2 | 1 | m-trifluoromethyl | fluoro | fluoro | hydrogen | hydrogen | α | methyl | fluoro | 15-epi-2,2,16,16-tetrafluoro-17-(m-trifluoromethylphenyl), methyl ester |
| G-73 | 2 | 0 |  | fluoro | fluoro | methyl | hydrogen | α | methyl | fluoro | 15-epi-2,2,16,16-tetrafluoro-15-methyl-17-phenyl, methyl ester |
| G-74 | 2 | 1 | p- | fluoro | fluoro | methyl | hydrogen | α | methyl | fluoro | 15-epi-2,2,16,16-tetra- |

Table G-continued

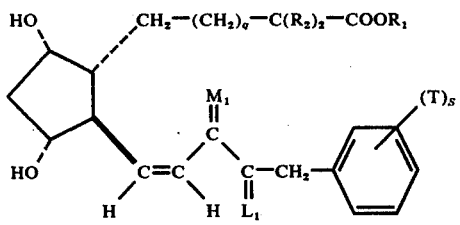

cis-13,18,19,20-trinor-PGF$_{1\alpha}$-type compounds

| Example | q | s | T | L$_1$ R$_3$ | R$_4$ | M$_1$ R$_5$ | R$_6$ | ~OR$_6$ | R$_1$ | R$_2$ | Name |
|---|---|---|---|---|---|---|---|---|---|---|---|
|  |  |  | fluoro |  |  |  | gen |  |  |  | fluoro-15-methyl-17-(p-fluorophenyl), methyl ester |
| G-75 | 2 | 1 | m-chloro | fluoro | fluoro | methyl | hydrogen | α | methyl | fluoro | 15-epi-2,2,16,16-tetrafluoro-15-methyl-17-(m-chlorophenyl), methyl ester |
| G-76 | 2 | 1 | m-trifluoromethyl | fluoro | fluoro | methyl | hydrogen | α | methyl | fluoro | 15-epi-2,2,16,16-tetrafluoro-15-methyl-17-(m-trifluoromethylphenyl), methyl ester |
| G-77 | 2 | 0 |  | fluoro | fluoro | hydrogen | methyl | α | methyl | fluoro | 15-epi-2,2,16,16-tetrafluoro-17-phenyl, methyl ester, 15-methyl ether |
| G-78 | 2 | 1 | p-fluoro | fluoro | fluoro | hydrogen | methyl | α | methyl | fluoro | 15-epi-2,2,16,16-tetrafluoro-17-(p-fluorophenyl), methyl ester, 15-methyl ether |
| G-79 | 2 | 1 | m-chloro | fluoro | fluoro | hydrogen | methyl | α | methyl | fluoro | 15-epi-2,2-,16,16-tetrafluoro-17-(m-chlorophenyl), methyl ester, 15-methyl ether |
| G-80 | 2 | 1 | m-trifluoromethyl | fluoro | fluoro | hydrogen | methyl | α | methyl | fluoro | 15-epi-2,2,16,16-tetrafluoro-16-(m-trifluoromethyl), methyl ester, 15-methyl ether |

Table H

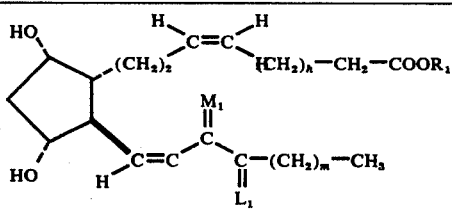

cis-4,5-didehydro-cis-13-PGF$_{1\alpha}$-type compounds

| Example | h | m | L$_1$ R$_3$ | R$_4$ | M$_1$ R$_5$ | R$_6$ | ~OR$_6$ | R$_1$ | Name |
|---|---|---|---|---|---|---|---|---|---|
| H-1 | 1 | 3 | methyl | hydrogen | hydrogen | hydrogen | α | methyl | 15-epi-16-methyl, methyl ester |
| H-2 | 1 | 3 | methyl | hydrogen | methyl | hydrogen | α | methyl | 15-epi-15,16-dimethyl, methyl ester |
| H-3 | 1 | 3 | methyl | hydrogen | hydrogen | methyl | α | methyl | 15-epi, methyl ester, 15-methyl ester |
| H-4 | 1 | 3 | methyl | methyl | hydrogen | hydrogen | α | methyl | 15-epi-16,16-dimethyl, methyl ester |
| H-5 | 1 | 3 | methyl | methyl | methyl | hydrogen | α | methyl | 15-epi-15,16,16-trimethyl, methyl ester |
| H-6 | 1 | 3 | methyl | methyl | hydrogen | methyl | α | methyl | 15-epi-16,16-dimethyl, methyl ester, 15-methyl ether |
| H-7 | 1 | 3 | fluoro | hydrogen | hydrogen | hydrogen | α | methyl | 15-epi-16-fluoro, methyl ester |
| H-8 | 1 | 3 | fluoro | hydrogen | methyl | hydrogen | α | methyl | 15-epi-15-methyl-16-fluoro, methyl ester |
| H-9 | 1 | 3 | fluoro | hydrogen | hydrogen | methyl | α | methyl | 15-epi-16-fluoro, methyl ester, 15-methyl ether |
| H-10 | 1 | 3 | fluoro | fluoro | hydrogen | hydrogen | α | methyl | 15-epi-16,16-difluoro, methyl ester |
| H-11 | 1 | 3 | fluoro | fluoro | methyl | hydrogen | α | methyl | 15-epi-15-methyl-16,16-difluoro, methyl ester |
| H-12 | 1 | 3 | fluoro | fluoro | hydrogen | methyl | α | methyl | 15-epi-16,16-difluoro, methyl ester, 15-methyl ether |
| H-13 | 1 | 3 | hydrogen | hydrogen | hydrogen | hydrogen | α | methyl | 15-epi, methyl ester |
| H-14 | 1 | 3 | hydrogen | hydrogen | methyl | hydrogen | α | methyl | 15-epi-15-methyl, methyl ester |
| H-15 | 1 | 3 | hydro | hydro- | hydro- | methyl | α | methyl | 15-epi, methyl ester, 15-methyl ether |

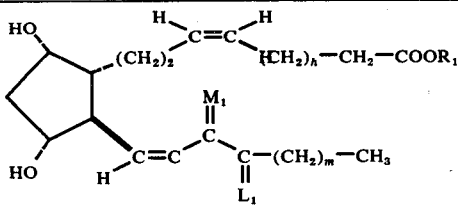

cis-4,5-didehydro-cis-13-PGF$_{1\alpha}$-type compounds

| Example | h | m | L$_1$ R$_3$ | R$_4$ | M$_1$ R$_5$ | R$_6$ | ~OR$_6$ | R$_1$ | Name |
|---|---|---|---|---|---|---|---|---|---|
| H-16 | 3 | 3 | hydrogen | hydrogen | hydrogen | hydrogen | α | methyl | 15-epi-2a,2b-dihomo, methyl ester |
| H-17 | 3 | 3 | hydrogen | hydrogen | methyl | hydrogen | α | methyl | 15-epi-2a,2b-dihomo-15-methyl, methyl ester |
| H-18 | 1 | 3 | methyl | methyl | hydrogen | hydrogen | α | methyl | 15-epi-2a,2b-dihomo-16,16-dimethyl, methyl ester |
| H-19 | 3 | 3 | methyl | methyl | methyl | hydrogen | α | methyl | 15-epi-2a,2b-dihomo-15,16,16-trimethyl, methyl ester |
| H-20 | 3 | 3 | fluoro | fluoro | hydrogen | hydrogen | α | methyl | 15-epi-2a,2b-dihomo-16,16-difluoro, methyl ester |
| H-21 | 3 | 3 | fluoro | fluoro | methyl | hydrogen | α | methyl | 15-epi-2a,2b-dihomo-15-methyl-16,16-difluoro, methyl ester |

Table J

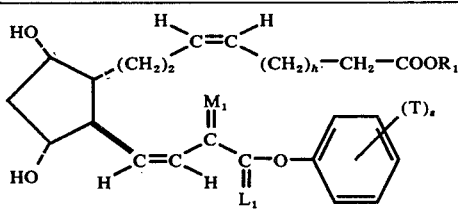

cis-4,5-didehydro-cis-13-PGF$_{1\alpha}$-type compounds

| Example | h | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| J-1 | 1 | 0 | | hydrogen | hydrogen | hydrogen | hydrogen | α | methyl | 15-epi-16-phenoxy-17,18,19,20-tetranor, methyl ester |
| J-2 | 1 | 1 | p-fluoro | hydrogen | hydrogen | hydrogen | hydrogen | α | methyl | 15-epi-16-(p-fluorophenoxy)-17,18,19,20-tetranor, methyl ester |
| J-3 | 1 | 1 | m-chloro | hydrogen | hydrogen | hydrogen | hydrogen | α | methyl | 16-(m-chlorophenoxy)-17,18,19,20-tetranor, methyl ester |
| J-4 | 1 | 1 | m-trifluoromethyl | hydrogen | hydrogen | hydrogen | hydrogen | α | methyl | 15-epi-16-(m-trifluoromethylphenoxy)-17,18,19,20-tetranor, methyl ester |
| J-5 | 1 | 0 | | hydrogen | hydrogen | methyl | hydrogen | α | methyl | 15-epi-15-methyl-16-phenoxy-17,18,19,20-tetranor, methyl ester |
| J-6 | 1 | 1 | p-fluoro | hydrogen | hydrogen | methyl | hydrogen | α | methyl | 15-epi-15-methyl-16-(p-fluorophenoxy)-17,18,19,20-tetranor, methyl ester |
| J-7 | 1 | 1 | m-chloro | hydrogen | hydrogen | methyl | hydrogen | α | methyl | 15-epi-15-methyl-16-(m-chlorophenoxy), methyl ester |
| J-8 | 1 | 1 | m-trifluoromethyl | hydrogen | hydrogen | methyl | hydrogen | α | methyl | 15-epi-15-methyl-16-(m-trifluoromethylphenoxy), methyl ester |
| J-9 | 1 | 0 | | hydrogen | hydrogen | hydrogen | methyl | α | methyl | 15-epi-16-phenoxy-17,18,19,20-tetranor, methyl ester 15-methyl ether |
| J-10 | 1 | 1 | p-fluoro | hydrogen | hydrogen | hydrogen | methyl | α | methyl | 15-epi-16-(p-fluorophenoxy)-17,18,19,20-tetranor, methyl ester, 15-methyl ether |
| J-11 | 1 | 1 | m-chloro | hydrogen | hydrogen | hydrogen | methyl | α | methyl | 15-epi-16-(m-chlorophenoxy)-17,18,19,20-tetranor, methyl ester, 15-methyl ether |
| J-12 | 1 | 1 | m-trifluoromethyl | hydrogen | hydrogen | hydrogen | methyl | α | methyl | 15-epi-16-(m-trifluoromethylphenoxy)-17,18,19,20-tetranor-methyl ester, 15-methyl ether |
| J-13 | 1 | 0 | | methyl | methyl | hydrogen | hydrogen | α | methyl | 15-epi-16-methyl-16-phenoxy-18,19,20-trinor, methyl ester |
| J-14 | 1 | 1 | p-fluoro | methyl | methyl | hydrogen | hydrogen | α | methyl | 15-epi-16-methyl-16-(p-fluorophenoxy)-18,19,20-trinor, methyl ester |
| J-15 | 1 | 1 | m-chloro | methyl | methyl | hydrogen | hydrogen | α | methyl | 15-epi-16-methyl-16-(m-chlorophenoxy)-18,19,20-trinor, methyl ester |
| J-16 | 1 | 1 | m-tri- | methyl | methyl | hydrogen | hydrogen | α | methyl | 15-epi-16-methyl-16-(m-tri- |

Table J-continued

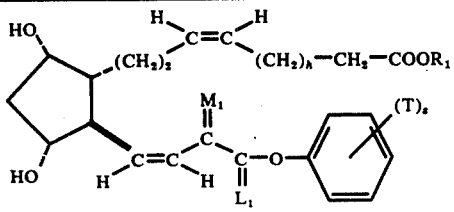

cis-4,5-didehydro-cis-13-PGF$_{1\alpha}$-type compounds

| Example | h | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
|   |   |   | fluoromethyl |   |   | gen | gen |   |   | fluoromethylphenoxy)-18,19,20-trinor, methyl ester |
| J-17 | 1 | 0 |   | methyl | methyl | methyl | hydrogen | α | methyl | 15-epi-15,16-dimethyl-16-phenoxy-18,19,20-trinor, methyl ester |
| J-18 | 1 | 1 | p-fluoro | methyl | methyl | methyl | hydrogen | α | methyl | 15-epi-15,16-dimethyl-16-(p-fluorophenoxy)-18,19,20-trinor, methyl ester |
| J-19 | 1 | 1 | m-chloro | methyl | methyl | methyl | hydrogen | α | methyl | 15-epi-15,16-dimethyl-16-(m-chlorophenoxy)-18,19,20-trinor, methyl ester |
| J-20 | 1 | 1 | m-trifluoromethyl | methyl | methyl | methyl | hydrogen | α | methyl | 15-epi-15,16-dimethyl-16-(m-trifluoromethylphenoxy)-18,19,20-trinor, methyl ester |
| J-21 | 1 | 0 |   | methyl | methyl | hydrogen | methyl | α | methyl | 15-epi-16-methyl-16-phenoxy-18,19,20-trinor, methyl ester, 15-methyl ether |
| J-22 | 1 | 1 | p-fluoro | methyl | methyl | hydrogen | methyl | α | methyl | 15-epi-16-methyl-16-(p-fluorophenoxy)-18,19,20-trinor, methyl ester, 15-methyl ether |
| J-23 | 1 | 1 | m-chloro | methyl | methyl | hydrogen | methyl | α | methyl | 15-epi-16-methyl-16-(m-chlorophenoxy)-18,19,20-trinor, methyl ester, 15-methyl ether |
| J-24 | 1 | 1 | m-trifluoro | methyl | methyl | hydrogen | methyl | α | methyl | 15-epi-16-methyl-16-(m-trifluoromethylphenoxy)-18,19,20-trinor, methyl ester, 15-methyl ether |
| J-25 | 3 | 0 |   | hydrogen | hydrogen | hydrogen | hydrogen | α | methyl | 15-epi-2a,2b-dihomo-16-phenoxy-17,18,19,20-tetranor, methyl ester |
| J-26 | 3 | 1 | p-fluoro | hydrogen | hydrogen | hydrogen | hydrogen | α | methyl | 15-epi-2a,2b-dihomo-16-(p-fluorophenoxy)-17,18,19,20-tetranor, methyl ester |
| J-27 | 3 | 1 | m-chloro | hydrogen | hydrogen | hydrogen | hydrogen | α | methyl | 15-epi-2a,2b-dihomo-16-(m-chlorophenoxy)-17,18,19,20-tetranor, methyl ester |
| J-28 | 3 | 1 | m-trifluoromethyl | hydrogen | hydrogen | hydrogen | hydrogen | α | methyl | 15-epi-2a,2b-dihomo-16-(m-trifluoromethylphenoxy)-17,18,19,20-tetranor, methyl ester |
| J-29 | 3 | 0 |   | hydrogen | hydrogen | methyl | hydrogen | α | methyl | 15-epi-2a,2b-dihomo-15-methyl-16-phenoxy-17,18,19,20-tetranor, methyl ester |
| J-30 | 3 | 1 | p-fluoro | hydrogen | hydrogen | methyl | hydrogen | α | methyl | 15-epi-2a,2b-dihomo-16-(p-fluorophenoxy)-17,18,19,20-tetranor, methyl ester |
| J-31 | 3 | 0 | m-chloro | hydrogen | hydrogen | methyl | hydrogen | α | methyl | 15-epi-2a,2b-dihomo-15-methyl-16-(m-chlorophenoxy)-17,18,19,20-tetranor, methyl ester |
| J-32 | 3 | 1 | m-trifluoromethyl | hydrogen | hydrogen | methyl | hydrogen | α | methyl | 15-epi-2a,2b-dihomo-15-methyl-16-(m-trifluoromethylphenoxy)-17,18,19,20-tetranor, methyl ester |

Table K

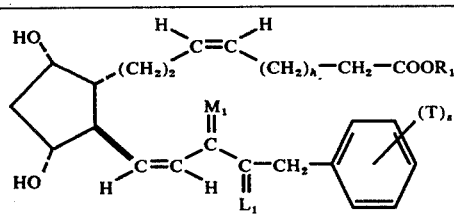

cis-4,5-didehydro-18,19,20-trinor-cis-13-PGF$_{1\alpha}$-type compounds

| Example | h | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| K-1 | 1 | 0 |   | hydrogen | hydrogen | hydrogen | hydrogen | α | methyl | 15-epi-17-phenyl, methyl ester |
| K-2 | 1 | 1 | p- | hydrogen | hydrogen | hydrogen | hydrogen | α | methyl | 15-epi-17-(p-fluorophenyl), |

Table K-continued

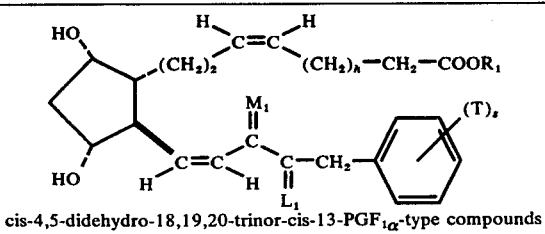

cis-4,5-didehydro-18,19,20-trinor-cis-13-PGF$_{1\alpha}$-type compounds

| Example | h | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| K-3 | 1 | 1 | m-chloro | hydrogen | hydrogen | hydrogen | hydrogen | α | methyl | 15-epi-17-(m-chlorophenyl), methyl ester |
| K-4 | 1 | 1 | m-tri-fluoro methyl) | hydrogen | hydrogen | hydrogen | hydrogen | α | methyl | 15-epi-17-(m-trifluoromethylphenyl), methyl ester |
| K-5 | 1 | 0 |  | hydrogen | hydrogen | methyl | hydrogen | α | methyl | 15-epi-15-methyl-17-phenyl, methyl ester |
| K-6 | 1 | 1 | p-fluoro | hydrogen | hydrogen | methyl | hydrogen | α | methyl | 15-epi-15-methyl-17-(p-fluorophenyl), methyl ester |
| K-7 | 1 | 1 | m-chloro | hydrogen | hydrogen | methyl | hydrogen | α | methyl | 15-epi-15-methyl-17-(m-chlorophenyl), methyl ester |
| K-8 | 1 | 1 | m-tri-fluoro methyl | hydrogen | hydrogen | methyl | hydrogen | α | methyl | 15-epi-15-methyl-17-(m-trifluoromethylphenyl), methyl ester |
| K-9 | 1 | 0 |  | hydrogen | hydrogen | hydrogen | methyl | α | methyl | 15-epi-17-phenyl, methyl ester, 15-methyl ether |
| K-10 | 1 | 1 | p-fluoro | hydrogen | hydrogen | hydrogen | methyl | α | methyl | 15-epi-17-(p-fluorophenyl), methyl ester, 15-methyl ether |
| K-11 | 1 | 1 | m-chloro | hydrogen | hydrogen | hydrogen | methyl | α | methyl | 15-epi-17-(m-chlorophenyl), methyl ester, 15-methyl ether |
| K-12 | 1 | 1 | m-tri-fluoro methyl | hydrogen | hydrogen | hydrogen | methyl | α | methyl | 15-epi-17-(m-trifluoromethylphenyl), methyl ester, 15-methyl ether |
| K-13 | 1 | 0 |  | methyl | methyl | hydrogen | hydrogen | α | methyl | 15-epi-16,16-dimethyl-17-phenyl, methyl ester |
| K-14 | 1 | 1 | p-fluoro | methyl | methyl | hydrogen | hydrogen | α | methyl | 15-epi-16,16-dimethyl-17-(p-fluorophenyl), methyl ester |
| K-15 | 1 | 1 | m-chloro | methyl | methyl | hydrogen | hydrogen | α | methyl | 15-epi-16,16-dimethyl-17-(m-chlorophenyl), methyl ester |
| K-16 | 1 | 1 | m-tri-fluoro methyl | methyl | methyl | hydrogen | hydrogen | α | methyl | 15-epi-16,16-dimethyl-17-(m-trifluoromethylphenyl), methyl ester |
| K-17 | 1 | 0 |  | methyl | methyl | methyl | hydrogen | α | methyl | 15-epi-15,16,16-trimethyl-17-phenyl, methyl ester |
| K-18 | 1 | 1 | p-fluoro | methyl | methyl | methyl | hydrogen | α | methyl | 15-epi-15,16,16-trimethyl-17-(p-fluorophenyl), methyl ester |
| K-19 | 1 | 1 | m-chloro | methyl | methyl | methyl | hydrogen | α | methyl | 15-epi-15,16,16-trimethyl-17- |
| K-20 | 1 | 1 | m-tri-fluoro | methyl | methyl | methyl | hydrogen | α | methyl | 15-epi-15,16,16-trimethyl-(m-trifluoromethylphenyl), methyl ester |
| K-21 | 1 | 0 |  | methyl | methyl | hydrogen | methyl | α | methyl | 15-epi-16,16-dimethyl-17-phenyl, methyl ester, 15-methyl ether |
| K-22 | 1 | 1 | p-fluoro | methyl | methyl | hydrogen | methyl | α | methyl | 15-epi-16,16-dimethyl-17-(p-fluorophenyl), methyl ester, 15-methyl ether |
| K-23 | 1 | 1 | m-chloro | methyl | methyl | hydrogen | methyl | α | methyl | 15-epi-16,16-dimethyl-17-(m-chlorophenyl), methyl ester 15-methyl ether |
| K-24 | 1 | 1 | m-tri-fluoro methyl | methyl | methyl | hydrogen | methyl | α | methyl | 15-epi-16,16-dimethyl-17-(m-trifluoromethylphenyl), methyl ester, 15-methyl ether |
| K-25 | 3 | 0 |  | hydrogen | hydrogen | hydrogen | hydrogen | α | methyl | 15-epi-2a,2b-dihomo-17-phenyl, methyl ester |
| K-26 | 3 | 1 | p-fluoro | hydrogen | hydrogen | hydrogen | hydrogen | α | methyl | 15-epi-2a,2b-dihomo-17-(p-fluorophenyl), methyl ester |
| K-27 | 3 | 1 | m-chloro | hydrogen | hydrogen | hydrogen | hydrogen | α | methyl | 15-epi-2a,2b-dihomo-17-(m-chlorophenyl), methyl ester |
| K-28 | 3 | 1 | m-tri-fluoro methyl | hydrogen | hydrogen | hydrogen | hydrogen | α | methyl | 15-epi-2a,2b-dihomo-17-(m-trifluoromethylphenyl), methyl ester |
| K-29 | 3 | 0 |  | hydrogen | hydrogen | methyl | hydrogen | α | methyl | 15-epi-2a,2b-dihomo-15-methyl-17-phenyl, methyl ester |
| K-30 | 3 | 1 | p-fluoro | hydrogen | hydrogen | methyl | hydrogen | α | methyl | 15-epi-2a,2b-dihomo-17-(p-fluorophenyl), methyl ester |
| K-31 | 3 | 0 | m-chloro | hydrogen | hydrogen | methyl | hydrogen | α | methyl | 15-epi-2a,2b-dihomo-15-methyl-17-(m-chlorophenyl), methyl ester |
| K-32 | 3 | 1 | m-tri-fluoro methyl | hydrogen | hydrogen | methyl | hydrogen | α | methyl | 15-epi-2a,2b-dihomo-15-methyl-17-(m-trifluoromethylphenyl), methyl ester |
| K-33 | 2 | 0 |  | fluoro | fluoro | hydrogen | hydrogen | α | methyl | 15-epi-16,16-difluoro-17-phenyl, methyl ester |
| K-34 | 3 | 1 | p-fluoro | fluoro | fluoro | hydrogen | hydrogen | α | methyl | 15-epi-16,16-difluoro-17-(p-fluorophenyl), methyl ester |
| K-35 | 3 | 1 | m-chloro | fluoro | fluoro | hydrogen | hydrogen | α | methyl | 15-epi-16,16-difluoro-17-(m-chlorophenyl), methyl ester |

Table K-continued

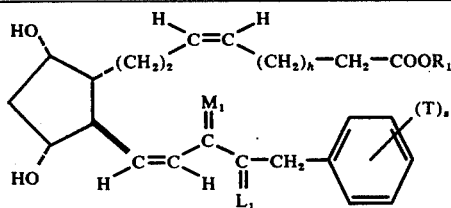

cis-4,5-didehydro-18,19,20-trinor-cis-13-PGF$_{1\alpha}$-type compounds

| Example | h | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| K-36 | 2 | 1 | m-trifluoromethyl | fluoro | fluoro | hydrogen | hydrogen | α | methyl | 15-epi-16,16-difluoro-17-(m-trifluoromethylphenyl), methyl ester |
| K-37 | 2 | 0 | | fluoro | fluoro | methyl | hydrogen | α | methyl | 15-epi-15-methyl-16,16-difluoro-17-phenyl, methyl ester |
| K-38 | 2 | 1 | p-fluoro | fluoro | fluoro | methyl | hydrogen | α | methyl | 15-epi-15-methyl-16,16-difluoro-17-(p-fluorophenyl), methyl ester |
| K-39 | 2 | 1 | m-chloro | fluoro | fluoro | methyl | hydrogen | α | methyl | 15-epi-15-methyl-16,16-difluoro-17-(m-chlorophenyl), methyl ester |
| K-40 | 2 | 1 | m-trifluoromethyl | fluoro | fluoro | methyl | hydrogen | α | methyl | 15-epi-15-methyl-16,16-difluoro-17-(m-trifluoromethylphenyl), methyl ester |
| K-41 | 2 | 0 | | fluoro | fluoro | hydrogen | methyl | α | methyl | 15-epi-16,16-difluoro-17-phenyl, methyl ester, 15-methyl ether |
| K-42 | 2 | 1 | p-fluoro | fluoro | fluoro | hydrogen | methyl | α | methyl | 15-epi-16,16-difluoro-17-(p-fluorophenyl), methyl ester, 15-methyl ether |
| K-43 | 2 | 1 | m-chloro | fluoro | fluoro | hydrogen | methyl | α | methyl | 15-epi-16,16-difluoro-17-(m-chlorophenyl), methyl ester, 15-methyl ether |
| K-44 | 2 | 1 | m-trifluoromethyl | fluoro | fluoro | hydrogen | methyl | α | methyl | 15-epi-16,16-difluoro-17-(m-trifluoromethylphenyl), methyl ester, 15-methyl ether |

Table L

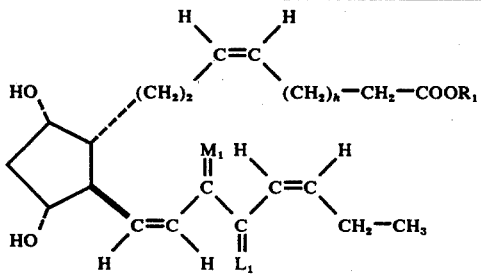

cis-4,5,17,18-tetradehydro-cis-13-PGF$_{1\alpha}$-type compounds

| Example | h | L$_1$ R$_3$ | R$_4$ | M$_1$ R$_5$ | R$_6$ | ~OR$_6$ | R$_1$ | Name |
|---|---|---|---|---|---|---|---|---|
| L-1 | 1 | hydrogen | hydrogen | hydrogen | hydrogen | α | methyl | 15-epi, methyl ester |
| L-2 | 1 | hydrogen | hydrogen | hydrogen | methyl | α | methyl | 15-epi, methyl ester, 15-methyl ether |
| L-3 | 1 | hydrogen | hydrogen | methyl | hydrogen | α | methyl | 15-epi-15-methyl, methyl ester |
| L-4 | 1 | hydrogen | methyl | hydrogen | hydrogen | α | methyl | 15-epi-16-methyl, methyl ester |
| L-5 | 1 | hydrogen | methyl | hydrogen | methyl | α | methyl | 15-epi-16-methyl, methyl ester, 15-methyl ether |
| L-6 | 1 | hydrogen | methyl | methyl | hydrogen | α | methyl | 15-epi-15,16-dimethyl, methyl ester |
| L-7 | 1 | methyl | methyl | hydrogen | hydrogen | α | methyl | 15-epi-16,16-dimethyl, methyl ester |
| L-8 | 1 | methyl | methyl | hydrogen | methyl | α | methyl | 15-epi-16,16-dimethyl, methyl ester, 15-methyl ether |
| L-9 | 1 | methyl | methyl | methyl | hydrogen | α | methyl | 15-epi-15,16,16-trimethyl, methyl ester |
| L-10 | 1 | hydrogen | fluoro | hydrogen | hydrogen | α | methyl | 15-epi-16-fluoro, methyl ester |
| L-11 | 1 | hydrogen | fluoro | hydrogen | methyl | α | methyl | 15-epi-16-fluoro, methyl ester, 15-methyl ether |
| L-12 | 1 | hydrogen | fluoro | methyl | hydrogen | α | methyl | 15-epi-15-methyl-16-fluoro, methyl ester |
| L-13 | 1 | fluoro | hydrogen | hydrogen | hydrogen | α | methyl | 15-epi-16,16-difluoro, methyl ester |
| L-14 | 1 | fluoro | fluoro | hydrogen | methyl | α | methyl | 15-epi-16,16-difluoro, methyl ester, 15-methyl ether |
| L-15 | 1 | fluoro | fluoro | methyl | hydrogen | α | methyl | 15-epi-15-methyl-16,16-difluoro, methyl |

Table L-continued

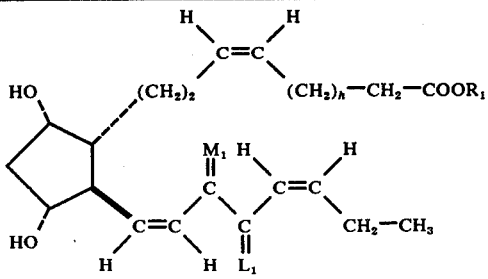

cis-4,5,17,18-tetradehydro-cis-13-PGF$_{1\alpha}$-type compounds

| Example | h | L$_1$ R$_3$ | R$_4$ | M$_1$ R$_5$ | R$_6$ | ~OR$_6$ | R$_1$ | Name |
|---|---|---|---|---|---|---|---|---|
| L-16 | 3 | hydrogen | hydrogen | hydrogen | hydrogen | α | methyl | 15-epi-2a,2b-dihomo, methyl ester |
| L-17 | 3 | hydrogen | hydrogen | hydrogen | methyl | α | methyl | 15-epi-2a,2b-dihomo, methyl ester, 15-methyl ether |
| L-18 | 3 | hydrogen | hydrogen | methyl | hydrogen | α | methyl | 15-epi-2a,2b-dihomo-15-methyl, methyl ester |
| L-19 | 3 | methyl | methyl | hydrogen | hydrogen | α | methyl | 15-epi-2a,2b-dihomo-16,16-dimethyl, methyl ester |
| L-20 | 3 | fluoro | fluoro | hydrogen | hydrogen | α | methyl | 15-epi-2a,2b-dihomo-16,16-difluoro, methyl ester |

Table M

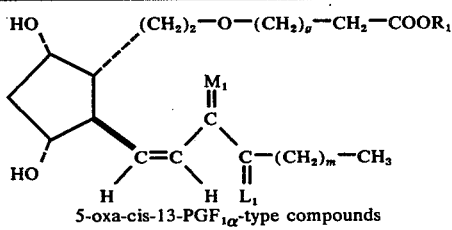

5-oxa-cis-13-PGF$_{1\alpha}$-type compounds

| Example | g | m | R$_3$ | R$_4$ | R$_5$ | R$_6$ | ~OR$_6$ | R$_1$ | Name |
|---|---|---|---|---|---|---|---|---|---|
| M-1 | 2 | 3 | methyl | hydrogen | hydrogen | hydrogen | α | methyl | 15-epi-16-methyl, methyl ester |
| M-2 | 2 | 3 | methyl | hydrogen | methyl | hydrogen | α | methyl | 15-epi-15,16-dimethyl, methyl ester |
| M-3 | 2 | 3 | methyl | hydrogen | hydrogen | methyl | α | methyl | 15-epi-methyl ester, 15-methyl ether |
| M-4 | 2 | 3 | methyl | methyl | hydrogen | hydrogen | α | methyl | 15-epi-16,16-dimethyl, methyl ester |
| M-5 | 2 | 3 | methyl | methyl | methyl | hydrogen | α | methyl | 15-epi-15,16,16-trimethyl, methyl ester |
| M-6 | 2 | 3 | methyl | methyl | hydrogen | methyl | α | methyl | 15-epi-16,16-dimethyl, methyl ester, 15-methyl ether |
| M-7 | 2 | 3 | fluoro | hydrogen | hydrogen | hydrogen | α | methyl | 15-epi-16-fluoro, methyl ester |
| M-8 | 2 | 3 | fluoro | hydrogen | methyl | hydrogen | α | methyl | 15-epi-15-methyl-16-fluoro, methyl ester |
| M-9 | 2 | 3 | fluoro | hydrogen | hydrogen | methyl | α | methyl | 15-epi-16-fluoro, methyl ester, methyl ester |
| M-10 | 2 | 3 | fluoro | fluoro | hydrogen | hydrogen | α | methyl | 15-epi-16,16-difluoro, methyl ester |
| M-11 | 2 | 3 | fluoro | fluoro | methyl | hydrogen | α | methyl | 15-epi-15-methyl-16,16-difluoro, methyl ester |
| M-12 | 2 | 3 | fluoro | fluoro | hydrogen | methyl | α | methyl | 15-epi-16,16-difluoro, methyl ester, 15-methyl ether |
| M-13 | 2 | 3 | hydrogen | hydrogen | hydrogen | hydrogen | α | methyl | 15-epi, methyl ester |
| M-14 | 2 | 3 | hydrogen | hydrogen | methyl | hydrogen | α | methyl | 15-epi-15-methyl, methyl ester |
| M-15 | 2 | 3 | hydrogen | hydrogen | hydrogen | methyl | α | methyl | 15-epi, methyl ester, 15-methyl ether |
| M-16 | 4 | 3 | hydrogen | hydrogen | hydrogen | hydrogen | α | methyl | 15-epi-2a,2b-dihomo, methyl ester |
| M-17 | 4 | 3 | hydrogen | hydrogen | methyl | hydrogen | α | methyl | 15-epi-2a,2b-dihomo-15-methyl, methyl ester |
| M-18 | 2 | 3 | methyl | methyl | hydrogen | hydrogen | α | methyl | 15-epi-2a,2b-dihomo-16,16-dimethyl, methyl ester |
| M-19 | 4 | 3 | methyl | methyl | methyl | hydrogen | α | methyl | 15-epi-2a,2b-dihomo-15,16,16-trimethyl, methyl ester |
| M-20 | 4 | 3 | fluoro | fluoro | hydrogen | hydrogen | α | methyl | 15-epi-2a,2b-dihomo-16,16-difluoro, methyl ester |

Table M-continued

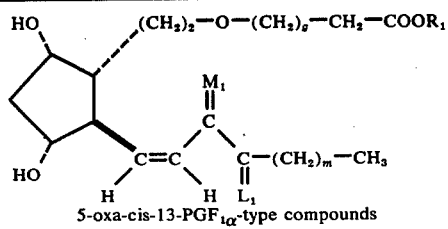

5-oxa-cis-13-PGF$_{1\alpha}$-type compounds

| Example | g | m | R$_3$ | R$_4$ | R$_5$ | R$_6$ | ~OR$_6$ | R$_1$ | Name |
|---|---|---|---|---|---|---|---|---|---|
| M-21 | 4 | 3 | fluoro | fluoro | methyl | hydrogen | α | methyl | 15-epi-2a,2b-dihomo-15-methyl-16,16-difluoro, methyl ester |

Table N

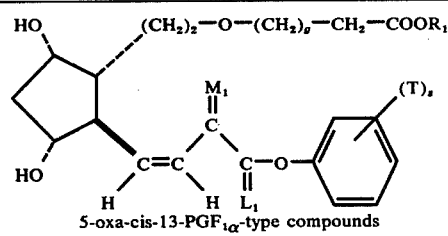

5-oxa-cis-13-PGF$_{1\alpha}$-type compounds

| Example | g | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| N-1 | 2 | 0 | | hydrogen | hydrogen | hydrogen | hydrogen | α | methyl | 15-epi-16-phenoxy-17,18,19,20-tetranor, methyl ester |
| N-2 | 2 | 1 | p-fluoro | hydrogen | hydrogen | hydrogen | hydrogen | α | methyl | 15-epi-16-(p-fluorophenoxy)-17,18,19,20-tetranor, methyl ester |
| N-3 | 2 | 1 | m-chloro | hydrogen | hydrogen | hydrogen | hydrogen | α | methyl | 15-epi-16-(m-chlorophenoxy)-17,18,19,20-tetranor, methyl ester |
| N-4 | 2 | 1 | m-trifluoro | hydrogen | hydrogen | hydrogen | hydrogen | α | methyl | 15-epi-16-(m-trifluoromethyl-phenoxy)-17,18,19,20-tetranor, methyl ester |
| N-5 | 2 | 0 | | hydrogen | hydrogen | methyl | hydrogen | α | methyl | 15-epi-15-methyl-16-phenoxy-17,18,19,20-tetranor, methyl ester |
| N-6 | 2 | 1 | p-fluoro | hydrogen | hydrogen | methyl | hydrogen | α | methyl | 15-epi-15-methyl-16-(p-fluorophenoxy)-17,18,19,20-tetranor, methyl ester |
| N-7 | 2 | 1 | m-chloro | hydrogen | hydrogen | methyl | hydrogen | α | methyl | 15-epi-15-methyl-16-(m-chlorophenoxy), methyl ester |
| N-8 | 2 | 1 | m-trifluoromethyl | hydrogen | hydrogen | methyl | hydrogen | α | methyl | 15-epi-15-methyl-16-(m-trifluoromethylphenoxy), methyl ester |
| N-9 | 2 | 0 | | hydrogen | hydrogen | hydrogen | methyl | α | methyl | 15-epi-16-phenoxy-17,18,19,20-tetranor, methyl ester, 15-methyl ether |
| N-10 | 2 | 1 | p-fluoro | hydrogen | hydrogen | hydrogen | methyl | α | methyl | 15-epi-16-(p-fluorophenoxy)-17,18,19,20-tetranor, methyl ester, 15-methyl ether |
| N-11 | 2 | 1 | m-chloro | hydrogen | hydrogen | hydrogen | methyl | α | methyl | 15-epi-16-(m-chlorophenoxy)-17,18,19,20-tetranor, methyl ester, 15-methyl ether |
| N-12 | 2 | 1 | m-trifluoromethyl | hydrogen | hydrogen | hydrogen | methyl | α | methyl | 15-epi-16-(m-trifluoromethyl-phenoxy)-17,18,19,20-tetranor, methyl ester, 15-methyl ether |
| N-13 | 2 | 0 | | methyl | methyl | hydrogen | hydrogen | α | methyl | 15-epi-16-methyl-16-phenoxy-18,19,20-trinor, methyl ester |
| N-14 | 2 | 1 | p-fluoro | methyl | methyl | hydrogen | hydrogen | α | methyl | 15-epi-16-methyl-16-(p-fluorophenoxy)-18,19,20-trinor, methyl ester |
| N-15 | 2 | 1 | m-chloro | methyl | methyl | hydrogen | hydrogen | α | methyl | 15-epi-16-methyl-16-(m-chlorophenoxy)-18,19,20-trinor, methyl ester |
| N-16 | 2 | 1 | m-trifluoromethyl | methyl | methyl | hydrogen | hydrogen | α | methyl | 15-epi-16-methyl-16-(m-trifluoromethylphenoxy)-18,19,20-trinor, methyl ester |
| N-17 | 2 | 0 | | methyl | methyl | methyl | hydrogen | α | methyl | 15-epi-15,16-dimethyl-16-phenoxy-18,19,20-trinor, methyl ester |
| N-18 | 2 | 1 | p-fluoro | methyl | methyl | methyl | hydrogen | α | methyl | 15-epi-15,16-dimethyl-16-(p-fluorophenoxy)-18,19,20-trinor, methyl ester |
| N-19 | 2 | 1 | m-chloro | methyl | methyl | methyl | hydrogen | α | methyl | 15-epi-15,16-dimethyl-16-(m-chlorophenoxy)-18,19,20-trinor, methyl ester |
| N-20 | 2 | 1 | m-trifluoromethyl | methyl | methyl | methyl | hydrogen | α | methyl | 15-epi-15,16-dimethyl-16-(m-trifluoromethylphenoxy)-18,19,20-trinor, methyl ester |

Table N-continued 5-oxa-cis-13-PGF$_{1\alpha}$-type compounds with structure: HO-cyclopentane with (CH$_2$)$_2$-O-(CH$_2$)$_g$-CH$_2$-COOR$_1$ side chain, M$_1$=C, C=C-H, H, C-O-phenyl-(T)$_s$, L$_1$

| Example | g | s | T | L$_1$ R$_3$ | L$_1$ R$_4$ | M$_1$ R$_5$ | M$_1$ R$_6$ | ~OR$_6$ | R$_1$ | Name |
|---|---|---|---|---|---|---|---|---|---|---|
| N-21 | 2 | 0 | | methyl | methyl | hydrogen | methyl | α | methyl | 15-epi-16-methyl-16-phenoxy-18,19,20-trinor, methyl ester, 15-methyl ether |
| N-22 | 2 | 1 | p-fluoro | methyl | methyl | hydrogen | methyl | α | methyl | 15-epi-16-methyl-16-(p-fluorophenoxy)-18,19,20-trinor, methyl ester, 15-methyl ether |
| N-23 | 2 | 1 | m-chloro | methyl | methyl | hydrogen | methyl | α | methyl | 15-epi-16-methyl-16-(m-chlorophenoxy)-18,19,20-trinor, methyl ester, 15-methyl ether |
| N-24 | 2 | 1 | m-trifluoromethyl | methyl | methyl | hydrogen | methyl | α | methyl | 15-epi-16-methyl-16-(m-trifluoromethylphenoxy)-18,19,20-trinor, methyl ester, 15-methyl ether |
| N-25 | 4 | 0 | | hydrogen | hydrogen | hydrogen | hydrogen | α | methyl | 15-epi-2a,2b-dihomo-16-phenoxy-17,18,19,20-tetranor, methyl ester |
| N-26 | 4 | 1 | p-fluoro | hydrogen | hydrogen | hydrogen | hydrogen | α | methyl | 15-epi-2a,2b-dihomo-16-(p-fluorophenoxy)-17,18,19,20-tetranor, methyl ester |
| N-27 | 4 | 1 | m-chloro | hydrogen | hydrogen | hydrogen | hydrogen | α | methyl | 15-epi-2a,2b-dihomo-16-(m-chlorophenoxy)-17,18,19,20-tetranor, methyl ester |
| N-28 | 4 | 1 | m-trifluoromethyl | hydrogen | hydrogen | hydrogen | hydrogen | α | methyl | 15-epi-2a,2b-dihomo-16-(m-trifluoromethylphenoxy)-17,18,19,20-tetranor, methyl ester |
| N-29 | 4 | 0 | | hydrogen | hydrogen | methyl | hydrogen | α | methyl | 15-epi-2a,2b-dihomo-15-methyl-16-phenoxy-17,18,19,20-tetranor, methyl ester |
| N-30 | 4 | 1 | p-fluoro | hydrogen | hydrogen | methyl | hydrogen | α | methyl | 15-epi-2a,2b-dihomo-16-(p-fluorophenoxy)-17,18,19,20-tetranor, methyl ester |
| N-31 | 4 | 0 | m-chloro | hydrogen | hydrogen | methyl | hydrogen | α | methyl | 15-epi-2a,2b-dihomo-15-methyl-16-(m-chlorophenoxy)-17,18,19,20-tetranor, methyl ester |
| N-32 | 4 | 1 | m-trifluoromethyl | hydrogen | hydrogen | methyl | hydrogen | α | methyl | 15-epi-2a,2b-dihomo-15-methyl-16-(m-trifluoromethylphenoxy)-17,18,19,20-tetranor, ester |

Table P 5-oxa-18,19,20-trinor-cis-13-PGF$_{1\alpha}$-type compounds with structure: HO-cyclopentane with (CH$_2$)$_2$-O-(CH$_2$)$_g$-CH$_2$-COOR$_1$ side chain, M$_1$=C, C=C-H, H, C-CH$_2$-phenyl-(T)$_s$, L$_1$

| Example | g | s | T | L$_1$ R$_3$ | L$_1$ R$_4$ | M$_1$ R$_5$ | M$_1$ R$_6$ | ~OR$_6$ | R$_1$ | Name |
|---|---|---|---|---|---|---|---|---|---|---|
| P-1 | 2 | 0 | | hydrogen | hydrogen | hydrogen | hydrogen | α | methyl | 15-epi-17-phenyl, methyl ester |
| P-2 | 2 | 1 | p-fluoro | hydrogen | hydrogen | hydrogen | hydrogen | α | methyl | 15-epi-17-(p-fluorophenyl), methyl ester |
| P-3 | 2 | 1 | m-chloro | hydrogen | hydrogen | hydrogen | hydrogen | α | methyl | 15-epi-17-(m-chlorophenyl), methyl ester |
| P-4 | 2 | 1 | m-trifluoromethyl | hydrogen | hydrogen | hydrogen | hydrogen | α | methyl | 15-epi-17-(m-trifluoromethylphenyl), methyl ester |
| P-5 | 2 | 0 | | hydrogen | hydrogen | methyl | hydrogen | α | methyl | 15-epi-15-methyl-17-phenyl, methyl ester |
| P-6 | 2 | 1 | p-fluoro | hydrogen | hydrogen | methyl | hydrogen | α | methyl | 15-epi-15-methyl-17-(p-fluorophenyl), methyl ester |
| P-7 | 2 | 1 | m-chloro | hydrogen | hydrogen | methyl | hydrogen | α | methyl | 15-epi-15-methyl-17-(m-chlorophenyl), methyl ester |
| P-8 | 2 | 1 | m-trifluoro | hydrogen | hydrogen | methyl | hydrogen | α | methyl | 15-epi-15-methyl-17-(m-trifluoromethylphenyl), methyl |

Table P-continued

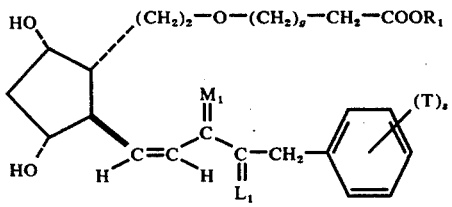

5-oxa-18,19,20-trinor-cis-13-PGF$_{1\alpha}$-type compounds

| Example | g | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| P-9 | 2 | 0 | methyl | hydrogen | hydrogen | hydrogen | methyl | α | methyl | 15-epi-17-phenyl, methyl ester, 15-methyl ether |
| P-10 | 2 | 1 | p-fluoro | hydrogen | hydrogen | hydrogen | methyl | α | methyl | 15-epi-17-(p-fluorophenyl), methyl ester, 15-methyl ether |
| P-11 | 2 | 1 | m-chloro | hydrogen | hydrogen | hydrogen | methyl | α | methyl | 15-epi-17-(m-chlorophenyl), methyl ester, 15-methyl ether |
| P-12 | 2 | 1 | m-trifluoromethyl | hydrogen | hydrogen | hydrogen | methyl | α | methyl | 15-epi-17-(m-trifluoromethylphenyl), methyl ester, 15-methyl ether |
| P-13 | 2 | 0 |  | methyl | methyl | hydrogen | hydrogen | α | methyl | 15-epi-16,16-dimethyl-17-phenyl, methyl ester |
| P-14 | 2 | 1 | p-fluoro | methyl | methyl | hydrogen | hydrogen | α | methyl | 15-epi-16,16-dimethyl-17-(p-fluorophenyl), methyl ester |
| P-15 | 2 | 1 | m-chloro | methyl | methyl | hydrogen | hydrogen | α | methyl | 15-epi-16,16-dimethyl-17-(m-chlorophenyl), methyl ester |
| P-16 | 2 | 1 | m-trifluoromethyl | methyl | methyl | hydrogen | hydrogen | α | methyl | 15-epi-16,16-dimethyl-17-(m-trifluoromethylphenyl), methyl ester |
| P-17 | 2 | 0 |  | methyl | methyl | methyl | hydrogen | α | methyl | 15-epi-15,16,16-trimethyl-17-phenyl, methyl ester |
| P-18 | 2 | 1 | p-fluoro | methyl | methyl | methyl | hydrogen | α | methyl | 15-epi-15,16,16-trimethyl-17-(p-fluorophenyl), methyl ester |
| P-19 | 2 | 1 | m-chloro | methyl | methyl | methyl | hydrogen | α | methyl | 15-epi-15,16,16-trimethyl-17-(m-chlorophenyl), methyl ester |
| P-20 | 2 | 1 | m-trifluoro | methyl | methyl | methyl | hydrogen | α | methyl | 15-epi-15,16,16-trimethyl-(m-trifluoromethylphenyl), methyl ester |
| P-21 | 2 | 0 |  | methyl | methyl | hydrogen | methyl | α | methyl | 15-epi-16,16-dimethyl-17-phenyl, methyl ester, 15-methyl ether |
| P-22 | 2 | 1 | p-fluoro | methyl | methyl | hydrogen | methyl | α | methyl | 15-epi-16,16-dimethyl-17-(p-fluorophenyl), methyl ester, 15-methyl ether |
| P-23 | 2 | 1 | m-chloro | methyl | methyl | hydrogen | methyl | α | methyl | 15-epi-16,16-dimethyl-17-(m-chlorophenyl), methyl ester, 15-methyl ether |
| P-24 | 2 | 1 | m-trifluoromethyl | methyl | methyl | hydrogen | methyl | α | methyl | 15-epi-16,16-dimethyl-17-(m-trifluoromethylphenyl), methyl ester, 15-methyl ether |
| P-25 | 4 | 0 |  | hydrogen | hydrogen | hydrogen | hydrogen | α | methyl | 15-epi-2a,2b-dihomo-17-phenyl, methyl ester |
| P-26 | 4 | 1 | p-fluoro | hydrogen | hydrogen | hydrogen | hydrogen | α | methyl | 15-epi-2a,2b-dihomo-17-(p-fluorophenyl), methyl ester |
| P-27 | 4 | 1 | m-chloro | hydrogen | hydrogen | hydrogen | hydrogen | α | methyl | 15-epi-2a,2b-dihomo-17-(m-chlorophenyl), methyl ester |
| P-28 | 4 | 1 | m-trifluoromethyl | hydrogen | hydrogen | hydrogen | hydrogen | α | methyl | 15-epi-2a,2b-dihomo-17-(m-trifluoromethylphenyl), methyl ester |
| P-29 | 4 | 0 |  | hydrogen | hydrogen | methyl | hydrogen | α | methyl | 15-epi-2a,2b-dihomo-15-methyl-17-phenyl, methyl ester |
| P-30 | 4 | 1 | p-fluoro | hydrogen | hydrogen | methyl | hydrogen | α | methyl | 15-epi-2a,2b-dihomo-17-(p-fluorophenyl), methyl ester |
| P-31 | 4 | 0 | m-chloro | hydrogen | hydrogen | methyl | hydrogen | α | methyl | 15-epi-2a,2b-dihomo-15-methyl-17-(m-chlorophenyl), methyl ester |
| P-32 | 4 | 1 | m-trifluoromethyl | hydrogen | hydrogen | methyl | hydrogen | α | methyl | 15-epi-2a,2b-dihomo-15-methyl-17-(m-trifluoromethylphenyl), methyl ester |
| P-33 | 2 | 0 |  | fluoro | fluoro | hydrogen | hydrogen | α | methyl | 15-epi-16,16-difluoro-17-phenyl, methyl ester |
| P-34 | 3 | 1 | p-fluoro | fluoro | fluoro | hydrogen | hydrogen | α | methyl | 15-epi-16,16-difluoro-17-(p-fluorophenyl), methyl ester |
| P-35 | 3 | 1 | m-chloro | fluoro | fluoro | hydrogen | hydrogen | α | methyl | 15-epi-16,16-difluoro-17-(m-chlorophenyl), methyl ester |
| P-36 | 2 | 1 | m-trifluoromethyl | fluoro | fluoro | hydrogen | hydrogen | α | methyl | 15-epi-16,16-difluoro-17-(m-trifluoromethylphenyl), methyl ester |
| P-37 | 2 | 0 |  | fluoro | fluoro | methyl | hydrogen | α | methyl | 15-epi-15-methyl-16,16-difluoro-17-phenyl, methyl ester |
| P-38 | 2 | 1 | p-fluoro | fluoro | fluoro | methyl | hydrogen | α | methyl | 15-epi-15-methyl-16,16-difluoro-17-(p-fluorophenyl), methyl ester |
| P-39 | 2 | 1 | m-chloro | fluoro | fluoro | methyl | hydrogen | α | methyl | 15-epi-15-methyl-16,16-difluoro-17-(m-chlorophenyl), methyl ester |
| P-40 | 2 | 1 | m-trifluoro | fluoro | fluoro | methyl | hydrogen | α | methyl | 15-epi-15-methyl-16,16-difluoro-17-(m-trifluoromethylphenyl), |

Table P-continued

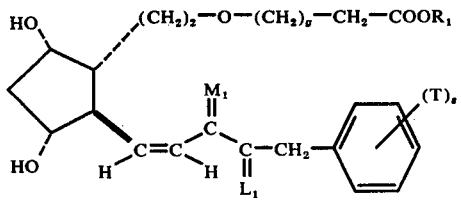

5-oxa-18,19,20-trinor-cis-13-PGF$_{1\alpha}$-type compounds

| Example | g | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| P-41 | 2 | 0 | methyl | fluoro | fluoro | hydrogen | methyl | α | methyl | 15-epi-16,16-difluoro-17-phenyl, methyl ester methyl ester, 15-methyl ether |
| P-42 | 2 | 1 | p-fluoro | fluoro | fluoro | hydrogen | methyl | α | methyl | 15-epi-16,16-difluoro-17-(p-fluorophenyl), methyl ester, 15-methyl ether |
| P-43 | 2 | 1 | m-chloro | fluoro | fluoro- | hydrogen | methyl | α | methyl | 15-epi-16,16-difluoro-17-(m-chlorophenyl), methyl ester, 15-methyl ether |
| P-44 | 2 | 1 | m-trifluoromethyl | fluoro | fluoro | hydrogen | methyl | α | methyl | 15-epi-16,16-difluoro-17-(m-trifluoromethylphenyl), methyl ester, 15-methyl ether |

For each of the compounds described in the Tables above, there are prepared by the procedures described in the Examples above the corresponding PGE-, PGA-, PGB-, or PGF$_\beta$ -type products. Further, using the appropriate bicyclic lactone starting material wherein the 3-position of the cyclopentane ring is unsubstituted, there are obtained the corresponding 11-deoxy-PGF$_\alpha$ -type compounds corresponding to the PGF$_\alpha$ -type compounds of the above tables. Likewise, by the procedure of the above examples the corresponding 11-deoxy-PGE and 11-deoxy-PGF$_\beta$ -type compounds are prepared.

I claim:

1. A compound of the formula

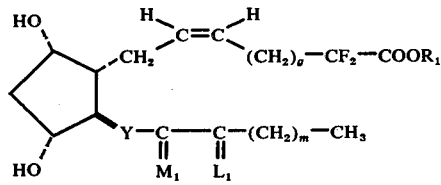

wherein Y is cis—CH=CH—; wherein g is 2, 3, or 4; wherein M$_1$ is

or

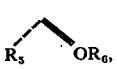

wherein R$_5$ and R$_6$ are hydrogen or methyl, with the proviso that one of R$_5$ and R$_6$ is methyl only when the other is hydrogen;

wherein L$_1$ is

or a mixture of

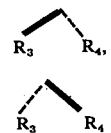

wherein R$_3$ and R$_4$ are hydrogen, methyl, or fluoro, being the same or different, with the proviso that one of R$_3$ and R$_4$ is fluoro only when the other is hydrogen or fluoro;

wherein m is one to 5, inclusive; and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein g is 2.

3. A compound according to claim 2, wherein m is 3.

4. A compound according to claim 3, wherein at least one of R$_3$ and R$_4$ is fluoro.

5. A compound according to claim 4, wherein R$_3$ and R$_4$ are both fluoro.

6. A compound according to claim 5, wherein R$_5$ and R$_6$ are hydrogen.

7. 15-epi-2,2,16,16-Tetrafluoro-cis-13-PGF$_{2\alpha}$, methyl ester, a compound according to claim 6.

8. A compound according to claim 3, wherein at least one of R$_3$ and R$_4$ is methyl.

9. A compound according to claim 8, wherein R$_3$ and R$_4$ are both methyl.

10. A compound according to claim 9, wherein R$_5$ and R$_6$ are both hydrogen.

11. 15-epi-2,2-Difluoro-16,16-dimethyl-cis-13-PGF$_{2\alpha}$, methyl ester, a compound according to claim 10.

12. A compound according to claim 3, wherein R$_3$ and R$_4$ are both hydrogen.

13. A compound according to claim 12, wherein $R_5$ and $R_6$ are both hydrogen.

14. 15-epi-2,2-Difluoro-cis-13-$PGF_{2\alpha}$, methyl ester, a compound according to claim 13.

15. A compound according to claim 12, wherein $R_5$ is methyl.

16. 15-epi-2,2-Difluoro-15-methyl-cis-13-$PGF_{2\alpha}$, methyl ester, a compound according to claim 15.

17. A compound according to claim 12, wherein $R_6$ is methyl.

18. 15-epi-2,2-Difluoro-cis-13-$PGF_{2\alpha}$, 15-methyl ether, methyl ester, a compound according to claim 17.

19. A compound of the formula

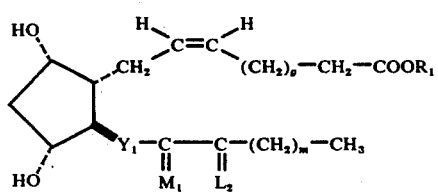

wherein Y is cis—CH=CH—; wherein $g$ is 2, 3, or 4; wherein $M_1$ is

or

wherein $R_5$ and $R_6$ are hydrogen or methyl, with the proviso tht one of $R_5$ and $R_6$ is methyl only when the other is hydrogen;

wherein $L_2$ is

or a mixture of

and

wherein $R_3$ and $R_4$ are hydrogen or fluoro, being the same or different, with the proviso that at least one of $R_3$ and $R_4$ is fluoro;

wherein $m$ is one to 5, inclusive; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

20. A compound according to claim 19, wherein $g$ is 4.

21. A compound according to claim 20, wherein $m$ is 3.

22. A compound according to claim 21, wherein $R_3$ and $R_4$ are both fluoro.

23. A compound according to claim 22, wherein $R_5$ and $R_6$ are hydrogen.

24. 15-epi-2a,2b-Dihomo-16,16-difluoro-cis-13-$PGF_{2\alpha}$, methyl ester, a compound according to claim 23.

25. A compound according to claim 19, wherein $g$ is 2.

26. A compound according to claim 25, wherein $m$ is 3.

27. A compound according to claim 26, wherein both $R_3$ and $R_4$ are fluoro.

28. A compound according to claim 27, wherein $R_5$ and $R_6$ are hydrogen.

29. 15-epi-16,16-difluoro-cis-13-$PGF_{2\alpha}$, methyl ester, a compound according to claim 28.

30. A compound of the formula

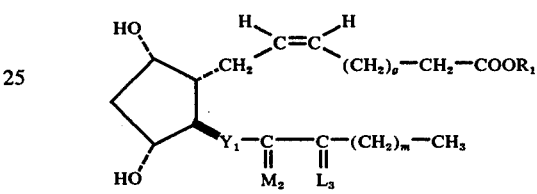

wherein Y is cis—CH=CH—; wherein $g$ is 2, 3, or 4; wherein $M_2$ is

or

wherein $L_3$ is

or a mixture of

and

wherein $R_3$ and $R_4$ are hydrogen or methyl, being the same or different;

wherein $m$ is one to 5, inclusive; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

31. A compound according to claim 30, wherein $g$ is 4.

32. A compound according to claim 31, wherein $m$ is 3.

33. A compound according to claim 32, wherein at least one of $R_3$ and $R_4$ is methyl.

34. A compound according to claim 33, wherein $R_3$ and $R_4$ are both methyl.

35. A compound according to claim 32, wherein $R_3$ and $R_4$ are hydrogen.

36. 15-epi-cis-13-$PGF_{2\alpha}$, methyl ester, 15-methyl ether, a compound according to claim 35.

* * * * *

UNITED STATES PATENT OFFICE
CERTIFICATE OF CORRECTION

Patent No. 4,026,909    Dated 31 May 1977

Inventor(s) Ernest W. Yankee

It is certified that error appears in the above-identified patent and that said Letters Patent are hereby corrected as shown below:

Column 4, line 15, "cyclopetane ring" should read -- cyclopentane ring --;
Column 5, line 13, "injery" should read -- injury --;
Column 6, line 3, "reducting" should read -- reducing --;
Column 7, line 52, "certan" should read -- certain --; line 59, "adre" should read -- are --;
Column 9, line 10, "reat" should read -- treat --;
Column 13, lines 32-33, "cis-CH=λCH-" should read -- cis-CH=CH- --;
Column 12, line 60, "$R_3$ and $R_4$ is or fluoro" should read -- $R_3$ and $R_4$ is fluoro --;
Column 18, line 45, "1-butylcyclopropyl," should read -- 2-butylcyclopropyl, --; line 48, "cyclohexnyl" should read -- cyclohexyl --;
Column 19, line 5, "(o-, m-, or p-(tolyl," should read -- (o-, m-, or p-)tolyl, --;
Column 20, line 20, "injusion" should read -- infusion --;
Column 23, lines 1-10, that portion of the formula reading

   should read   

Column 42, line 3, "With respct" should read -- With respect --; line 5, "5-ox -$PGF_1\alpha$-type" should read -- 5-oxa-$PGF_1\alpha$-type --; line 28, "haloitryl'" should read -- halonitryl --; line 42, "4-oxo-$PGF_1\alpha$-type" should read -- 4-oxa-$PGF_1\alpha$-type --;
Column 43, lines 58-59, "$HOOC-CH_2-(CH_2)_h CH_2-P-(C_6H_5)_3$" should read -- $HOOC-CH_2-(CH_2)_h-CH_2-P-(C_6H_5)_3$ --; line 60, "reation proceeds" should read -- reaction proceeds --; line 68, "$PGF_1$ -type" should read -- $PGF_1\alpha$-type --;
Column 44, line 53, "$M_{18}$ is O" should read -- $M_{18}$ is $\underset{||}{O}$ --;

UNITED STATES PATENT OFFICE
CERTIFICATE OF CORRECTION

Patent No. 4,026,909    Dated 31 May 1977

Inventor(s) Ernest W. Yankee

It is certified that error appears in the above-identified patent and that said Letters Patent are hereby corrected as shown below:

Column 46, line 4, "15-metyl-" should read -- 15-methyl- --;
Column 55, line 16, "additon rate" should read -- addition rate --; line 45, "s zero, one," should read -- s is zero, one, --;
Column 58, line 28, "7-brmoheptanoic" should read -- 7-bromoheptanoic --
Column 60, line 56, "8.15δ PGF , PGE, PGF , PGA" should read -- 8.15δ. PGFα, PGE, PGFβ, PGA --; lines 61-62, "11-deoxy-PGF , 11-deoxy-PGE, and 11-deoxy-PGF -type" should read -- 11-deoxy-PGFα, 11-deoxy-PGE, and 11-deoxy-PGFβ-type --;
Column 61, line 47, "11-deoxy-PGF ," should read -- 11-deoxy-PGFα, --; line 5, "or PGF -type" should read -- or PGFβ-type --; line 6, "PGF -, PGE-, and PGF -type" should read -- PGFα-, PGE-, and PGFβ-type --; line 22, "cis-1-ocetnyl)-" should read -- cis-1-octenyl)- --; line 47, "7.8 8.15." should read -- 7.8-8.15. --;
Column 62, line 30, "-cis-11-butenyl;" should read -- -cis-11-butenyl; --; lines 49-50, "cis-CH3=λCH-" should read -- cis-CH=CH- --;
Column 64, line 31, "filtered throgh Gelite." should read -- filtered through Celite. --;
Column 66, line 43, "5-Oxa-cis-13PGF₁α," should read -- 5-Oxa-cis-13-PGF₁α, --;
Column 68, line 3, "₁₁,₁₅ -bis(tetrahydropyranyl)" should read -- 11,15-bis(tetrahydropyranyl) --;
Column 69, line 2, "Example b 8, part C" should read -- Example 8, part C --;
Column 70, lines 63-64, "but bromide," should read -- but using in place of 4-carboxybutyltriphenylphosphonium bromide, --;
Column 73, lines 28-29, "cis-Ch=CH-," should read -- cis-CH=CH-, --;
Column 74, lines 34-35, "M₁ is M₁₈ is Ω," should read
-- M₁ is OH CH₃, M₁₈ is Ω, --;
Column 76, line 25, "préparing sure" should read -- preparing pure --;
Column 77, line 42, "3.6-6," should read -- 3.6-4.6 --;
Column 78, line 57, "in place sodium" should read -- in place of sodium --;

Page 3 of 4 Pages

UNITED STATES PATENT OFFICE
CERTIFICATE OF CORRECTION

Patent No. 4,026,909  Dated 31 May 1977

Inventor(s) Ernest W. Yankee

It is certified that error appears in the above-identified patent and that said Letters Patent are hereby corrected as shown below:

Column 78, line 66, "15-epi-16,16-Dimethyl-13-$PGF_2\alpha$" should read -- 15-epi-16,16-Dimethyl-cis-13-$PGF_2\alpha$ --;

Column 79, line 10, "are observes" should read -- are observed --; line 32, "-[(3)-3-" should read -- -[(3S)-3- --; line 35, "3.7-5.1-6.1" should read -- 3.7-5.1, and 5.1-6.1 --;

Column 80, lines 40-41, "methyl ester. 30 of methylene chloride is then added rapidly. The resulting mixture" should read -- methyl ester. --; line 47, "is then slowly combined" should read -- is then added rapidly. The resulting mixture is then slowly combined --;

Column 81, line 67, "9nmixture" should read -- 9-epimeric mixture --;

Columns 85-90, headings "$R_3$  $R_4$  $R_5$  $R_3$  $\sim OR_6$  $R_3$  $R_2$" should read -- $R_3$  $R_4$  $R_5$  $R_6$  $-OR_6$  $R_1$  $R_2$ --;

Columns 85-86, "Name" for Example B-17, "18,19,20-trinow," should read -- 18,19,20-trinor,--;

Columns 87-88, "s" for Example B-35, should read -- 1 --

Columns 89-90, "Name" for Example B-42, "18,19,20-trinor, methyl" should read -- 18,19,20-trinor, methyl ester --;

Columns 97-98, "Name" for Example C-77, "tetrafluoro-7-phenyl," should read -- tetrafluoro-17-phenyl, --; "Name" for Example C-78, "15-methyl ester" should read -- 15-methyl ether --;

Columns 99-102, Formula for Table D, that part of the formula reading

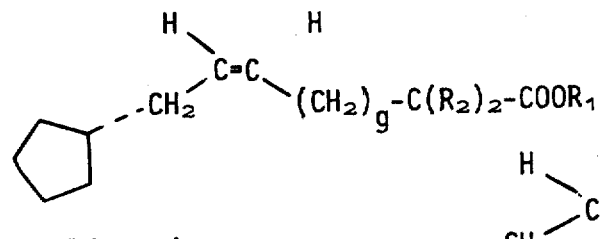

should read

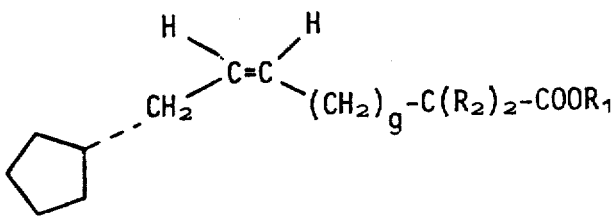

UNITED STATES PATENT OFFICE
CERTIFICATE OF CORRECTION

Patent No. 4,026,909  Dated 31 May 1977

Inventor(s) Ernest W. Yankee

It is certified that error appears in the above-identified patent and that said Letters Patent are hereby corrected as shown below:

Columns 107-108, "Name" for Example F-39, "(m-chlorophen-" should read -- (m-chlorophenoxy-18,19,20-trinor, methyl ester --;

Columns 111-112, "Name" for Example G-4, "15-ei-17-(m-trifluoromethylphenyl, methyl ester" should read -- 15-epi-17-(m-trifluoromethylphenyl), methyl ester --;

Columns 113-114, "Name" for Example G-38, "17-(p-ester" should read -- 17-(p-chlorophenyl), methyl ester --;

Columns 123-124, "Name" for Example K-19, "-17-" should read -- -17-(m-chlorophenyl), methyl ester --.

Signed and Sealed this

*Nineteenth* Day of *May 1981*

[SEAL]

*Attest:*

RENE D. TEGTMEYER

*Attesting Officer*  *Acting Commissioner of Patents and Trademarks*